US011603408B2

(12) United States Patent
Graham et al.

(10) Patent No.: US 11,603,408 B2
(45) Date of Patent: *Mar. 14, 2023

(54) METHODS FOR TREATING SKIN INFECTION BY ADMINISTERING AN IL-4R ANTAGONIST

(71) Applicants: Regeneran Pharmaceuticals, Inc., Tarrytown, NY (US); Sanofi Biotechnology, Paris (FR)

(72) Inventors: Neil Graham, Croton-on-Hudson, NY (US); Marius Ardeleanu, White Plains, NY (US); Allen Radin, New York, NY (US); Jennifer D. Hamilton, Hopewell Junction, NY (US); Ariel Teper, Hastings-on-Hudson, NY (US)

(73) Assignees: Regeneron Pharmaceuticals, Inc., Tarrytown, NY (US); Sanofi Biotechnology, Paris (FR)

(*) Notice: Subject to any disclaimer, the term of this patent is extended or adjusted under 35 U.S.C. 154(b) by 82 days.

This patent is subject to a terminal disclaimer.

(21) Appl. No.: 16/424,094

(22) Filed: May 28, 2019

(65) Prior Publication Data

US 2019/0367622 A1 Dec. 5, 2019

Related U.S. Application Data

(63) Continuation of application No. 14/632,988, filed on Feb. 26, 2015, now Pat. No. 10,370,449.

(60) Provisional application No. 61/946,237, filed on Feb. 28, 2014, provisional application No. 61/952,245, filed on Mar. 13, 2014, provisional application No. 61/986,371, filed on Apr. 30, 2014, provisional application No. 62/100,128, filed on Jan. 6, 2015.

(30) Foreign Application Priority Data

Sep. 24, 2014 (EP) ..................... 14306476

(51) Int. Cl.
*A61K 39/395* (2006.01)
*C07K 16/28* (2006.01)
*A61K 45/06* (2006.01)
*A61K 39/00* (2006.01)

(52) U.S. Cl.
CPC ...... *C07K 16/2866* (2013.01); *A61K 39/3955* (2013.01); *A61K 45/06* (2013.01); *A61K 2039/505* (2013.01); *A61K 2039/54* (2013.01); *C07K 2317/21* (2013.01); *C07K 2317/56* (2013.01); *C07K 2317/565* (2013.01); *C07K 2317/76* (2013.01)

(58) Field of Classification Search
CPC ............ A61K 39/3955; C07K 16/2866; A61P 17/00
See application file for complete search history.

(56) References Cited

U.S. PATENT DOCUMENTS

| | | |
|---|---|---|
| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson |
| 8,252,284 B2 | 8/2012 | Singh |
| 8,324,192 B2 | 12/2012 | Dohil |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Kim et al., Scientific Reports, 2019, vol. 9, Article No. 7772.*
Ong, P.Y., Expert Opin. Emerging Drugs, 2012, vol. 17(2):129-133.*
Radin et al., J. Allergy Clin. Immunol., 2013, vol. 131(2), Suppl., page AB158 (available online Jan. 26, 2013).*
Ring et al., J. Eur. Acad. Dermatol. Venereol., Aug. 2012, vol. 26(8):1045-1060.*
Regeneron 2011 Annual Report (Apr. 2011), 12 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.

(Continued)

*Primary Examiner* — Xiaozhen Xie
(74) *Attorney, Agent, or Firm* — Merchant & Gould P.C.

(57) ABSTRACT

The present invention provides methods for treating, preventing or ameliorating skin infections, including bacterial and viral infections. In certain embodiments, the invention provides methods to reduce skin infection in a patient with atopic dermatitis (AD). Also provided are methods for improving skin barrier function, and methods for reducing the risk of inflammation due to microbial infection in a patient in need thereof. The methods of the present invention comprise administering to a patient in need thereof a pharmaceutical composition comprising an interleukin-4 receptor (IL-4R) antagonist such as an anti-IL-4R antibody.

17 Claims, 36 Drawing Sheets

Specification includes a Sequence Listing.

(56) References Cited

U.S. PATENT DOCUMENTS

| | | | |
|---|---|---|---|
| 8,337,839 B2 | 12/2012 | Martin | |
| 8,338,135 B2 | 12/2012 | Stevens | |
| 8,497,528 B2 | 7/2013 | Lee | |
| 8,604,171 B2 | 12/2013 | Singh | |
| 8,637,239 B2 | 1/2014 | Furuta | |
| 8,735,095 B2 | 5/2014 | Martin et al. | |
| 8,945,559 B2 | 2/2015 | Dix | |
| 9,238,692 B2 | 1/2016 | Dix | |
| 9,290,574 B2 | 3/2016 | Kostic | |
| 9,574,004 B2 | 2/2017 | Ardeieanu | |
| 10,059,771 B2 | 8/2018 | Mannent | |
| 10,066,017 B2 | 9/2018 | Mannent | |
| 10,137,193 B2 | 11/2018 | Pirozzi | |
| 10,370,449 B2 | 8/2019 | Graham | |
| 10,392,439 B2 | 8/2019 | Stahl | |
| 10,435,473 B2 | 10/2019 | Dix | |
| 10,485,844 B2 | 11/2019 | Radin | |
| 10,669,341 B2 | 6/2020 | Stahl | |
| 10,676,530 B2 | 6/2020 | Stahl | |
| 10,730,948 B2 | 8/2020 | Kostic | |
| 11,034,768 B2 | 6/2021 | Amin | |
| 11,053,309 B2 | 7/2021 | Radin | |
| 2002/0002132 A1* | 1/2002 | Pluenneke | A61K 38/1793 424/141.1 |
| 2003/0103938 A1 | 6/2003 | Jinquan | |
| 2003/0113387 A1 | 6/2003 | Tsuchida | |
| 2003/0124121 A1 | 7/2003 | Pluenneke | |
| 2005/0031609 A1 | 2/2005 | Hultsch | |
| 2005/0074462 A1 | 4/2005 | Holmgren | |
| 2005/0118176 A1 | 6/2005 | Mosley | |
| 2005/0255532 A1 | 11/2005 | Ruben | |
| 2005/0282181 A1 | 12/2005 | Yan | |
| 2006/0013811 A1 | 1/2006 | Dina | |
| 2007/0041976 A1 | 2/2007 | Pluenneke | |
| 2007/0274996 A1 | 11/2007 | Carter | |
| 2008/0054606 A1 | 5/2008 | Eriksson | |
| 2008/0160035 A1 | 7/2008 | Stevens et al. | |
| 2009/0074793 A1 | 3/2009 | Martin | |
| 2009/0098142 A1 | 4/2009 | Kasaian | |
| 2009/0264392 A1 | 10/2009 | Warndahl | |
| 2010/0021476 A1 | 1/2010 | Stevens et al. | |
| 2010/0047254 A1 | 2/2010 | Martin | |
| 2010/0291107 A1 | 11/2010 | Stevens et al. | |
| 2011/0195500 A1 | 8/2011 | Rothenberg | |
| 2012/0004205 A1 | 1/2012 | Rothenberg | |
| 2012/0052072 A1 | 3/2012 | Martin | |
| 2012/0097565 A1 | 4/2012 | Dix | |
| 2012/0135010 A1 | 5/2012 | Stevens et al. | |
| 2012/0164080 A1 | 6/2012 | Hill | |
| 2012/0207815 A1 | 8/2012 | Benhamou | |
| 2013/0052190 A1 | 2/2013 | Collins | |
| 2013/0078675 A1 | 3/2013 | Martin | |
| 2013/0324435 A1 | 12/2013 | Rothenberg | |
| 2014/0072583 A1 | 3/2014 | Ardeleanu | |
| 2014/0187523 A1 | 7/2014 | Dohil | |
| 2014/0271681 A1 | 9/2014 | Martin | |
| 2014/0356372 A1 | 12/2014 | Stahl | |
| 2015/0017176 A1 | 1/2015 | Kostic | |
| 2015/0185228 A1 | 7/2015 | Reisacher | |
| 2015/0246973 A1 | 9/2015 | Graham | |
| 2016/0152718 A1 | 6/2016 | Kostic | |
| 2016/0185866 A1 | 6/2016 | Mannent | |
| 2017/0333557 A1 | 11/2017 | Ardeleanu | |
| 2018/0078603 A1 | 3/2018 | Radin | |
| 2018/0094069 A1 | 4/2018 | Stahl | |
| 2018/0094070 A1 | 4/2018 | Stahl | |
| 2018/0179288 A1 | 6/2018 | Martin et al. | |
| 2019/0040126 A1 | 2/2019 | Radin | |
| 2019/0169299 A1 | 6/2019 | Amin | |
| 2019/0183973 A1 | 6/2019 | Hamilton | |
| 2019/0345253 A1 | 11/2019 | Bansal | |
| 2020/0246416 A1 | 8/2020 | Radin | |
| 2020/0299393 A1 | 9/2020 | Stahl | |
| 2020/0332014 A1 | 10/2020 | Kostic | |
| 2020/0345843 A1 | 11/2020 | Asrat | |
| 2021/0038715 A1 | 2/2021 | Hamilton | |
| 2021/0040222 A1 | 2/2021 | Bansal | |
| 2021/0163611 A1 | 6/2021 | Martin | |
| 2021/0220470 A1 | 7/2021 | Bryce et al. | |
| 2021/0363237 A1 | 11/2021 | Radin | |
| 2021/0363264 A1 | 11/2021 | Hamilton | |
| 2022/0110999 A1 | 4/2022 | Radin | |
| 2022/0220211 A1 | 7/2022 | Orengo | |
| 2022/0298250 A1 | 9/2022 | Bansal | |

FOREIGN PATENT DOCUMENTS

| | | | |
|---|---|---|---|
| EP | 1113818 B1 | 5/2006 | |
| EP | 2022507 A1 | 2/2009 | |
| EP | 1527100 | 7/2009 | |
| JP | 05-246874 | 9/1993 | |
| JP | 2006-131623 | 5/2006 | |
| JP | 2016521713 | 7/2016 | |
| RU | 2162711 | 2/2001 | |
| RU | 2453303 C1 | 6/2012 | |
| RU | 2552929 C1 | 6/2015 | |
| WO | WO 1992/19259 | 11/1992 | |
| WO | WO 1994/14975 | 7/1994 | |
| WO | WO 2001/092340 | 12/2001 | |
| WO | WO 2003/048083 | 6/2003 | |
| WO | WO 2005/047331 | 5/2005 | |
| WO | WO 2005/085284 | 9/2005 | |
| WO | WO 2006/003407 | 1/2006 | |
| WO | WO 2006/072564 | 7/2006 | |
| WO | WO 2006/083390 | 8/2006 | |
| WO | WO 2008/054606 | 5/2008 | |
| WO | 2008/116149 | 9/2008 | |
| WO | WO 2009/124954 | 10/2009 | |
| WO | WO 2010/053751 | 5/2010 | |
| WO | WO 2010/065557 | 6/2010 | |
| WO | WO 2010/120524 | 10/2010 | |
| WO | WO 2011/026966 | 3/2011 | |
| WO | WO 2012/047954 | 4/2012 | |
| WO | WO-2012047954 A1 * | 4/2012 | A61P 27/14 |
| WO | WO 2012/094643 | 7/2012 | |
| WO | WO 2012/177945 | 12/2012 | |
| WO | WO 2013/051928 | 4/2013 | |
| WO | WO 2013/088109 | 6/2013 | |
| WO | 2013/116287 | 8/2013 | |
| WO | WO 2013/155010 | 10/2013 | |
| WO | WO 2014/031610 | 2/2014 | |
| WO | WO 2014/039461 | 3/2014 | |
| WO | WO 2014/059178 | 4/2014 | |
| WO | 2014/122144 | 8/2014 | |
| WO | WO 2014/197470 | 12/2014 | |
| WO | WO 2014/205365 | 12/2014 | |
| WO | WO 2015/006571 | 1/2015 | |
| WO | 2015/127229 | 8/2015 | |
| WO | WO 2016/077675 | 5/2016 | |
| WO | WO 2017/143270 | 8/2017 | |
| WO | 2018/035393 | 2/2018 | |
| WO | 2018/057776 | 3/2018 | |
| WO | WO 2018/045130 | 3/2018 | |
| WO | 2018/151836 | 8/2018 | |
| WO | 2018/201051 | 11/2018 | |
| WO | 2019/089473 | 5/2019 | |

OTHER PUBLICATIONS

ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.

Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.

ClinicalTrials.gov Identifier: NTC02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.

(56) References Cited

OTHER PUBLICATIONS

Dupixent (dupilumab) Injection, for Subcutaneous Use, Patient Information, Issued Mar. 2017, 34 pages.
Carr, Warner, "Topical Calcineurin Inhibitors for Atopic Dermatitis: Review and Treatment Recommendations", Pediatric Drugs, 2013, vol. 15, pp. 303-310.
Ayars, Andrew G. et al., "Pharmacologic Therapies in Pulmonology and Allergy", 2016 Med Clin N Am 100(4):851-868.
Mashkovsky, M.D., Moscow, 2001 Medicines, 14th edition, v1:8-9. (Cited in RU Application 2019109062 received on Dec. 24, 2020). Russian Office Action and Search Report in Application 2019109062, received Dec. 24, 2020, with English translation, 32 pages.
Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.
Phan, N.Q. et al., "Assessment of pruritis intensity: prospective study on validity and reliability of the visual analogue scale, numeric rating scale, and verbal rating scale in 471 patients with chronic pruritis", Acta. Derm. Venereol., 2012, 92: 502-507.
Marone et al., "The Intriguing Role of Interleukin 13 in the Pathophysiology of Asthma", Frontiers in Pharmacology, 2019, pp. 1-3.
Wegmann et al., "Targeting Cytokines in Asthma therapy: could IL-37 be a Solution?", Expert Review of Respiratory Medicine, 2017, vol. 11, No. 9, pp. 675-677.
Nicodeme et al., "Esophageal Distensibiiity as a Measure of Disease Severity in Patients with Eosinophilic Esophagitis", Clinical Gastroenterology and Hepatology, 2013, vol. 11, No. 9, pp. 1101-1107.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Huang, Evie et al.: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology, (Mar. 9, 2019), pp. 1-15.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, Apr. 29, 2019), page S4.
Database Embase [Online], Elsevier Science Publishers, Amsterdam,NL; (May 1, 2019), Cork M. J: "605 Efficacy and safety of dupilumab in adolescent patients with moderate-to-severe atopic dermatitis", XP002793331, Database accession No. EMB-002001809007 abstract, 3 pages.
Database Embase [Online], Elsevier Science Publishers, Amsterdam,NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract, 2 pages.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Blankestijn, Mark et al., "Could Duratumumab be used to treat severe allergy?", Journal of Allergy and Clinical Immunology, vol. 139, No. 5, Jan. 19, 2017, p. 1677-1678.e3.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.

Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Darsow, Ulf et al., "Pruritus and Atopic Dermatitis", Clinic Rev Allerg Immunol (2011) 41:237-244.
Buddenkotte, J. et al., "Pathophysiology and therapy of pruritis in allergic and atopic diseases", Allergy 65 (2010), 805-821.
Abonia et al. (2013) Journal of Allergy Clin Immunol "High prevalence of eosinophilic esophagitis in patients with inherited connective tissue disorders".
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.
Aceves et al. (2009) Immunol Allergy Clin N Am 29:197-211 "Relationships Between Eosinophilic Inflammation, Tissue Remodeling, and Fibrosis in Eosinophilic Esophagitis".
Akiyama, et al., A Study on Indoor Allergens Measured in Home Environments of Adult-Asthmatic Patients, Housing Research Foundation, Research Annual Report, 1997, No. 24, Study No. 9620, 1-10.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (2011) Gastroenterology 141:1593-1604 "An Antibody Against IL-5 Reduces Numbers of Esophageal Intraepithelial Eosinophils in Children with Eosinophilic Esophagitis".
Assa'ad, Amal, What is new in the Treatment of Eosinophilic Eosophagitis?Clinical and Translational Allergy 2011 (Suppl 1):S69, doi: 10.1186/2045-7022-1-S 1-S69.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balint and Larrick (1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (2008) The Journal of Clinical Investigation 118(11):3546-3556 "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (Jul. 10, 2014) New England Journal of Medicine 371(2): 130-139 "Dupilumab treatment in adults with moderate-to-severe atopic dermatitis".
Beyer et al. (2002) Journal of Allergy Clin Immunol 109(4):707-713 "Human milk-specific mucosal lymphocytes ofthe gastrointestinal tract display a $T_H2$ cytokine profile".
Bhardwaj and Ghaffari (2012) Ann Allergy Asthma Immunol 109:155-159 "Biomarkers for eosinophilic esophagitis: a review".
Bieber, T., et al., "Atopic dermatitis: a candidate for disease-modifying strategy," Allergy 67 (2012) 969-975.
Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".

(56) References Cited

OTHER PUBLICATIONS

Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17)31191-1.
British Society for Allergy And Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
BSACI News Report confirming BSACI conference date of Jul. 8-10, 2013, 2 pages.
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to snaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Clinical Trials, Study NCT00676884—"A Phase Study to Investigate the Effects of Repeated Administration of AeroDerm in Subjects with Atopic Dermatitis", Aeroderm first publication of clinical study protcol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Corren et al. (2010) American Journal of Respiratory and Critical Care Medicine 181 (8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Ummunology, (Sep. 2009) vol. 39, Supp.
Davies et al. (1996) Immunotechnol. 2(3):169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results ofthe HEROES Study", Oct. 14, 2016, retrieved from the Internet on Sep. 20, 2018 at: https://www.eventscribe.com/2016/ACG/QRcode.asp?Pres=178380, 3 pages.
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institiute, Imperial College London, UK, published Aug. 12, 2015, 12 pages.
European Notice of Opposition in Application 13765844.9, mailed Feb. 22, 2019, 34 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Garriga, A., "71st Annual Meeting of the American Academy of Dermatology (AAAD) . . . Miami Beach, FL, Mar. 1-5, 2013", Drugs ofthe Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gavett et al. (1997) The American Physiological Society 272(16):L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti—IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition ofthe IL-4/IL-13 Receptor System completely Abrogates Humoral Immune Response to Allergen and Development of Allergic Symptoms in Vivo".

(56) References Cited

OTHER PUBLICATIONS

Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Highlights of Prescribing Information, DUPIXENT {dupilumab} injection, for subcutaneous use Initial U.S. Approval: 2017, U.S. Food and Drug Administration (FDA), Revised Mar. 2017.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology—Head and Neck Surgery 137(4):555-561 "The Lund-Mackay staging system for chronic rhinosinusitis: How is it used and what does it predict?"
International Investigative Dermatology, Edinburgh, Conference Posters, May 8-11, 2013, 4 pages.
Ivashkiin, V. T., et al., "Eosinophillic esophagitis," a textbook for physicians, Moscow, "AISPI RAS" JSC, Feb. 14, 2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in pateints with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".

Kakinuma, Takashi et al. (2001) J. Allergy Clin. Immunol. 107(3):535-541 "Thymus and activation-regulated chemokine in atopic dertatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6): 1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5): 651-657 "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al. (2007) Clinical Reviews in Allergy & Immunology 33(3):167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp. Bioi. Med. 206(3):233-237 "In vivo biological effects of recombinant soluble interleukin-4 receptor".
Mannon et al. (2012) GUT 61(12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".

(56) References Cited

OTHER PUBLICATIONS

Mathias, et al., "IgE-mediated systemic anaphylaxs and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta (2002) 237-250.
Muller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".
Nguyen, Tran Hoai et al., "FutureForms of Immunotherapy and Immunomodulators in Allergic Disease", Immunol Allergy Clin N Am 31 (2011); 343-365.
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2): 129-133 "Editorial update on emerging treatments of atopic dermatitis".
Otani et al. (2013) Journal of Allergy and Clinical Immunology 131 (6):1576-1582 "Anti-IL-5 therapy reduces mast cell and IL-9 cell numbers in pediatric patients with eosinophilic esophagitits".
Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.

PCT IPRP from International Patent Application No. PCT/ US2013/055747 issued Feb. 24, 2015, 11 pages.
PCT ISR and WO for International Patent Application No. PCT/US2015/017834 dated May 20, 2015, 15 pages.
PCT ISR and WO from International Patent Application No. PCT/US2014/043440 dated Oct. 6, 2014.
PCT ISR for International Patent Application No. PCT/US2013/055747 mailed Feb. 13, 2014, 9 pages.
Pesek, Robert D. et al., "Emerging drugs for eosinophilic esophagitis", Expert Opinion on Emerging Drugs, vol. 23, No. 2, Apr. 3, 2018, 12 pages.
Peserico et al. (2008) British Journal of Dermatology 158:801-807 "Reduction of relapses of atopic dermatitis with methylprednisolone aceptonate cream twice weekly in addition to maintenance treatment with enrollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5—TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8):1045-1060 "Guidelines for treatement of atopic eczema (atopic dermatitis) Part 1".
Roitt et al. (2001) Mosby-Harcourt Publishers Limited, Immunology— Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, dated Oct. 6, 2017, with translation, 4 pages.
Saeki, Hidehisa, "Guidelines for Management of Atopic Dermatis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting ofthe American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.

(56) References Cited

OTHER PUBLICATIONS

Sanofi, "Positive Phase 2a Results of Dupilumab in Asthma in the New England Journal of Medicine," May 21, 2013, Regeneron Pharmaceuticals, Inc.

Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.

Sato et al. (1993) J. Immunol. 150(7):2717-2723 "Recombinant soluble murine IL-4 receptor can inhibit or enhance IgE responses in vivo".

Scavuzzo et al. (2005) Biomedicine & Pharmacotherapy 59(6):323-9 "Inflammatory mediators and eosinophilia in atopic and non-atopic patients with nasal polyposis".

Schmidt-Weber (2012) Chem Immunol Allergy 96:120-125 "Anti-IL-4 as a New Strategy in Allergy".

Schmitt et al. (2007) J. of Allergy and Clinical Immunology 120(6):1389-1398 "What are the best outcome measurements for atopic eczema? A systematic review".

Schneider et al. (2013) J. Allergy Clin Immunol 132(6):1368-1374 "A pilot study of omalizumab to facilitate rapid oral desensitization in high-risk peanut-allergic patients".

Sekiya et al. (2002) Allergy 57:173-177 "Increased levels of a TH2-type CC chemokine thymus and activation-regulated chemokine (TARC) in serum and induced sputumm of asthmatics".

Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.

Silverberg J.I., et al., P481, "Dupilumab treatment rapidly improves itch in patients with moderate-to-severe atopic dermatitis" An Allergy Asthma Immunol. 2017;119(suppl 5):S95.

Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.

Simpson, Eric L. et al., "Dupilumab therapy provides clinically meaningful improvement in patient-reported outcomes (PROs): A phase lib, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.

Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.

Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".

Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.

Stein et al. (2006) J Allergy Clin Immunol 118(6):1312-1319 "Anti-IL-5 (mepolizumab) therapy for eosinophilic esophagitis".

Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".

Stone et al. (2008) Clinical & Experimental Allergy 38(12):1858-1865 "Immunomodulatory therapy of eosinophil-associated gastro-intestinal diseases".

Strauman (2009) Immunol Allergy Clin N Am 29:11-18 "Clinical Evaluation of the Adult who has Eosinophilic Esophagitis".

Straumann (2005) J Allergy Clin Immunol 115(2):418-419 "Eosinophilic esophagitis: Escalating epidemiology?"

Straumann et al. (2001) J Allergy Clin Immunol 108(6):954-961 "Idiopathic eosinophilic esophagitis is associated with a $T_H2$-type allergic inflammatory response".

Straumann et al. (2009) Gut "Anti-interleukin-5 antibody treatment (mepolizumab) in active eosinophilic oesophagitis: a randomized, placebo-controlled, double-blind trial".

Tazawa et al. (2004) Arch Dermatol Res 295:459-464 "Relative importance of IL-4 and IL-13 in lesional skin of atopic dermatitis".

Tepper et al. (1990) Cell 52:457-467 "IL-4 Induces Allergic-like Inflammatory Disease and Alters T Cell Development in Transgenic Mice".

Terui, et al., "Learning from Fungus Allergy in Atopic Dermatitis Patients," Japan J. Med. Mycol, 2000, vol. 41, No. 3, 157-160.

Thaci, Diamant et al.: "Efficacy and Safety of Dupilumab in Adults with Moderate-to_Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015.

Tomkinson et al. (2001) J. Immunol 166:5792-5800 "A Murine IL-4 Receptor Antagonist that Inhibits IL-4-and IL-13-induced Responses Prevents Antigen-Induced Airway Eosinophilia and Airway Hyper-responsiveness".

Tsianakas, Athanasios et al., "Dupilumab: A Milestone in the Treatment of Atopic Dermatitis," The Lancet, The Lancet Publishing Group, GB vol. 387, No. 10013, Oct. 8, 2015.

Ul-Haq, Zaheer et al., "lnterleukin-4 receptor signaling and its binding mechanism: A therapeutic insight from inhibitors tool box", Cytokine & Growth Factor Review 32 (2016) 3-15.

Vajdos et al. (2002) Journal of Molecular Biology 320(2):415-428 "Comprehensive functional maps of the antigen-binding site of an anti-ErbB2 antibody obtained with shotgun scanning mutagenesis".

Vakharia, Paras P. et al., "Monoclonal Antibodies for Atopic Dermatitis: Progress and Potential", BioDrugs (2017) 31:409-422.

Veerappan et al. (2009) Clinical Gastroenterology and Hepatology 7:420-426 "Prevalence of Eosinophilic Esophagitis in an Adult Population Undergoing Upper Endoscopy: A Prospective Study".

Vestergaard et al. (2000) The Journal of Investigative Dermatology 115(4):640-646 "A $Th_2$ Chemokine, TARC, Produced by Keratinocytes May Recruit $CLA^+CCR4^+$ Lymphocytes into Lesional Atopic Dermatitis Skin".

Virchow et al. (1994) Lung 172:313-334 "Cellular and immunological markers of allergic and intrinsic bronchial asthma".

Walker et al. (1993) Clinical and Experimental Allergy 23:145-153 "Atopic dermatitis: correlation of peripheral blood T cell activation, eosinophilia and serum factors with clinical severity".

Wang and Liu (2008) Current Opinion in Immunology 20:697-702 "The IL-17 cytokine family and their role in allergic inflammation".

Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.

Wark et al. (2006) Advanced Drug Delivery Reviews 58:657-670 "Latest technologies for the enhancement of antibody affinity".

Watson et al. (2011) Allergy, Asthma & Clinical Immunology 7:S4 "Atopic dermatitis".

Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".

Weinbrand-Goichberg et al. (2013) Immunol Res "Eosinophilic esophagitis: an immune-mediated esophageal disease".

Wenzel et al. (2007) Lancet 370:1422-1431 "Effect of an interleukin-4 variant on late phase asthmatic response to allergen challenge in asthmatic patients: results of two phase 2a studies".

Wenzel et al. (2010) European Respiratory Society, Annual Congress 2010, "ERS—Programme" pp. 3980.

Wenzel et al. (2013) New England Journal of Medicine 368(26):2455-2466 "Dupilumab in Persistent Asthma with Elevated Eosinophil Levels".

Wershil (2009) Immunol Allergy Clin N Am 29:189-195 "Exploring the Role of Mast Cells in Eosinophilic Esophagitis".

Whalley et al. (2004) British Journal of Dermatology 150:274-283 "A new instrument for assessing quality of life in atopic dermatitis: international development of the Quality of Life Index for Atopic Dermatitis (QoLIAD)".

(56) References Cited

OTHER PUBLICATIONS

Wilhelm and Stockinger (2011) Frontiers in Immunology 2(68) "Innate lymphoid cells and type 2 (Th2) mediated immune responses-pathogenic or beneficial?"
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".
Zurawski et al. (1995) J. Bioi. Chem. Am. Society of Biolochemical Biologists 270(23):13869-13878 "The primary binding subunit of the human Interleukin-4 receptor is also a component of the Interleukin-13 receptor".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.
De Genst, Erwin et al., "Antibody repertoire development in camelids", Developmental and Comparative Immunology, 30 (2006); 187-198.
Ward, E. Sally et al., "Binding activities of a repertoire of single immunoglobin variable domains secreted from *Escherichia coli*", Nature, 1989, 341 :544-546.
Barthelemy, Pierre et al., "Comprehensive analysis of the factors contributing to the stability and solubility of autonomous human VH domains", Journal of Biological Chemistry, 2008, 283:3639-3654.
Choi, Yoonjoo et al., "Predicting antibody complementarity determining region structures without classification", Molecular Biosystems, 2011, 7:3327-334.
Griffiths, Andrew et al., "Human anti-self antibodies with high specificity from phage display libraries", The EMBO Journal, 1993, 12:725-734.
Klimka et al., "Human anti-CD30 recombinant antibodies by guided phage antibody selection using cell panning", British Journal of Cancer, 2000, 83:252-260.
Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.
Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Siegfried et al., "Use of dupilumab in pediatric atopic dermatitis: Access, dosing, and implications for managing severe atopic dermatitis", Pediatric Dermatology, vol. 36, No. 1, Jan. 2019, pp. 172-176.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Waccholz et al., "Detection of Allergen-Specific IgE Antibody Responses", 2005, Journal of Immunotoxicology, 1:3-4, 189-199.
Janeway, Jr. et al., Immunobiology, 3rd Edition, 1997, Garland Publishing Inc., pp. 11:1-11:22.
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Kussie, Paul, et al., "A Single Engineered Amino Acid Substitution Changes Antibody Fine Specificty", Journal of Immunology:152, pp. 146-152, 1994.
Boguniewicz, Mark et al., "Recent insights into atopic dermatitis and implications for management of infectious complications", Journal of Allergy and Clinical Immunology, Jan. 2010, 125(1):4-13.
Bergmann, M.M. et al., "Evaluation of Food Allergy in Patients With Atopic Dermatitis", J Allergy Clin Immunol, 1, pp. 22-28, Jan. 1, 2013.
Radin, A., et al., "First-in-Human study of REGN668/SAR231893 (IL-4Rα mAB): safety, tolerability and biomarker results of a randomized, double-blind, placebo-controlled, single ascending dose study in healthy volunteers", J Allergy Clin Immunology, 2013, 131(2) Suppl, p. AB158.
Navarini, A., et al., "Interrupting IL-6-receptor signaling improves atopic dermatitis but associates with bacterial superinfection", Nov. 2011 J Allergy Clin Immunol, Letters to the Editor, pp. 1128-1130.
De Keyser, Filip, "Choice of biologic therapy for patients with rheumatoid arthritis: the infection perspective", Current Rheumatology Reviews, 2011, vol. 7, No. 1, pp. 77-87.
Langley, R.G., et al., "Secukinumab in plaque psoriasis—results of two phase 3 trials", New England Journal of Medicine, Jul. 24, 2014, 371:4, pp. 326-338.
Linden, Carey et al., "Analysis of allergen specific IgE cut points to cat and dog in the Childhood Allergy Study", Annals of Allergy, Asthma & Immunology, 2011, 106.2: 153-158. e2.
Celakovska, J. et al., "Sensitization to aeroallergens in atopic dermatitis patients: association with concomitant allergic diseases", JEADV 2015; 29, 1500-1505.
Lucae, S. et al., "IgE responses to exogenous and endogenous allergens in atopic dermatitis patients under long-term systemic cyclosporine A treatment", Allergy 71 (2016); 115-118.
Kharkevich, D.A., "Pharmacology (Farmakologiya: A. Scholarly Manual)", 10th Ed., Moscow: GEOTAR-Media, 2010, pp. 73-74 and pp. 846-847, with English translation of cited pages, 12 pages total.
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Takashi Yoshike, "Treatment For Atopic Dermatitis", Juntendo Medical Journal, 1999, vol. 45, No. 3, pp. 352-360, 33 pages with English translation.
Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.
Nomura, Ichiro et al., "*Staphylococcus Aureus* and Atopic Dermatitis", (2000), IRYO vol. 54, No. 2, pp. 62-66, 18 pages with English translation.

(56) References Cited

OTHER PUBLICATIONS

Hamilton, Jennifer et al., "Dupilumab Normalizes the Eosinophilic Esophagitis Disease Transcriptome In Adult Patients With Eosinophilic Esophagitis", May 1, 2020, Abstract, retrieved from internet on Aug. 5, 2021 at: https://www.sciencedirect.com/science/article/pii/S0016508520327669?via%3Dihub, 1 page.

Reed, Craig, et al., "Patient-reported outcomes in esophageal diseases", Clinical Gastroenterology and Hepatology, Elsevier, Amsterdam, NL, vol. 16. no. 3, pp. 305-310.

Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.

Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.

Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.

Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.

Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.

Garraud, Olivier, et al., "Regulation of immunoglobulin production in hyper-IgE (Job's) syndrome", J. Allergy Clin. Immunol., Feb. 1999. (2 Pt. 1): 333-340.

Finkelman, Fred, et al., "Regulation of murine in vivo IgG and IgE responses by a monoclonal anti-IL-4 receptor antibody", Jun. 1991;3(6); 599-607.

Clinical Trials, Study NCT00436670, "Phase II Study to Evaluate the Efficacy of AMG 317", first posted Feb. 19, 2007, Amgen actual study completion date—Feb. 2009, 7 pages.

Mncent, M et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.

Russian Office Action and Search Report in Application 2020140639, dated Aug. 17, 2022, with English translation, 26 pages.

Blakely, Kim et al., "Dupilumab, a monoclonal antibody for atopic dermatitis: a review of current literature", Skin Therapy Letter, Mar.-Apr. 2016,vol. 21, No. 2, Dupilumab Clinical Trials in AD, 13 pages.

Clinical Trials, Study NCT01859988, phase 2b, "Study of Dupilumab Administered to Adult Patients With Moderate-to-Severe Atopic Dermatitis", study completion date—Sep. 2014, 10 pages.

D'erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c.1475-1478, 8 pages.

Grechkina, L.I. et al., "Characteristics for the physical development indices demonstrated by adolescents born in Magadan", Siberian Medical Journal, 2013, No. 3, Results and discussion, Table 1, obtained from: https://cyberleninka.ru/article/n/harakteristika-pokazateley-fizicheskogo-razvitiya-podrostkov-urozhentsev-magadana/viewer, with English translation, 9 pages.

Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.

Balabolkin, I. et al., "Modern concepts of pathogenesis and therapy of atopic dermatitis in children", Pharmateka, 2017, No. 1, p. 53-60, with English translation, 14 pages.

Kwiatek, Monika et al., "Mechanical properties of the esophagus in eosinophilic esophagitis" Gastroenterology, 2011, vol. 140, No. 1, pp. 82-90.

Abe, Yasuhiko, et al., "The Diagnosis of Eosinophilic Esophagitis", (English abstract), Gastroenterological Endoscopy, Sep. 2014, vol. 56, Issue 9, pp. 3378-3393.

"Dupilumab therapy in moderate-to-severe atopic dermatitis provides positive results in the first two phase III clinical trials", J Int Pharm Res, vol. 43, No. 4, Aug. 31, 2016, p. 785 (with English translation).

* cited by examiner

METHODS FOR TREATING SKIN INFECTION BY ADMINISTERING AN IL-4R ANTAGONIST

CROSS-REFERENCE TO RELATED APPLICATIONS

This application is a continuation of U.S. patent application Ser. No. 14/632,988, filed on Feb. 26, 2015, entitled, "Methods for Treating Skin Infection by Administering an IL-4R Antagonist," now U.S. Pat. No. 10,370,449, issued on Aug. 6, 2019, which claims the benefit under 35 U.S.C. § 119(e) of U.S. provisional application No. 61/946,237, filed on Feb. 28, 2014; 61/952,245, filed on Mar. 13, 2014; 61/986,371, filed on Apr. 30, 2014; 62/100,128, filed on Jan. 6, 2015, and under 35 U.S.C. § 119(b) of European application No. 14306476, filed on Sep. 24, 2014, the disclosures of each herein incorporated by reference in their entireties.

FIELD OF THE INVENTION

The present invention relates to the treatment and/or prevention of skin infection associated with IL-4R-related conditions. More specifically, the invention relates to the administration of interleukin-4 receptor (IL-4R) antagonists to reduce skin infection in a patient in need thereof.

BACKGROUND

Skin infections generally occur at the sites of skin damage produced by, for example, atopic dermatitis, burns, cracks in the skin, cuts, blisters, insect bites, surgical wounds, intravenous drug injection or sites of intravenous catheter insertion, or long-term usage of topical steroids. The skin infections may be localized or diffuse with severe inflammation of the epidermal, dermal and sub-cutaneous layers of the skin. They may be caused by various microbes including, but not limited to *Staphylococcus aureus, Streptococcus* spp., Herpes simplex virus, molluscum contagiosum virus, and fungi such as *Microsporum* spp. and *Trichophyton* spp.

Atopic dermatitis (AD) is a chronic/relapsing inflammatory skin disease characterized by intense pruritus (e.g., severe itch) and by scaly and dry eczematous lesions. AD is often associated with other atopic disorders such as allergic rhinitis and asthma. Patients with atopic dermatitis are susceptible to serious skin infections caused by bacteria and viruses including, but not limited to *S. aureus* and herpes simplex virus. *S. aureus* causes severe localized and diffuse (e.g., impetigo) skin infections. *S. aureus* colonization and infections of lesions significantly impacts AD disease activity and severity.

Typical treatments include topical lotions and moisturizers, antibiotics, anti-viral and anti-fungal agents. Most treatment options, however, offer only temporary, incomplete, symptom relief. Moreover, in many patients with moderate-to-severe AD, prolonged use of topical corticosteroids or calcineurin inhibitors may lead to increased risk of skin microbial infections. Thus, a need exists in the art for novel targeted therapies for the treatment and/or prevention of skin infections.

BRIEF SUMMARY OF THE INVENTION

According to certain aspects of the present invention, methods are provided for treating, preventing or ameliorating a skin infection in a subject. Also included are methods of reducing the susceptibility to a skin infection or reducing the risk of inflammation due to microbial infection in a subject. In certain embodiments, the invention provides for methods to improve skin barrier function and to reduce microbial colonization of the skin in a subject. The methods of the present invention comprise administering to a subject in need thereof a pharmaceutical composition comprising a therapeutically effective amount of an interleukin-4 receptor (IL-4R) antagonist. In certain embodiments, the pharmaceutical composition is administered subcutaneously at a dose of 75-600 mg.

In certain embodiments, the skin infection may be a bacterial infection or a viral infection. In certain embodiments, the skin infection may be caused by a microbe selected from the group consisting of *Staphylococcus aureus, Streptococcus* spp., *Pseudomonas aeruginosa, Bacteroides* spp., Herpes simplex virus, molluscum contagiosum virus, coxsackievirus, vaccinia virus, *Candida albicans, Microsporum* spp., *Trichophyton* spp., *Penicillium* spp., *Cladosporium* spp., *Alternaria* spp., and *Aspergillus* spp. In certain embodiments, the skin infection is selected from the group consisting of impetigo, cellulitis, infected dermatitis, eczema herpeticum, folliculitis, infected blister, mycosis, tinea versicolor, *Staphylococcus aureus* infection, and *Streptococcus* infection.

In certain embodiments, the skin infection is caused by *S. aureus*. In some embodiments, the *S. aureus* colonization of skin is reduced upon administration of a therapeutically effective amount of an IL-4R antagonist.

According to certain embodiments, the present invention provides methods for treating or preventing a skin infection or for reducing microbial colonization of the skin in a subject, wherein the methods comprise sequentially administering to the subject about 50 mg to about 600 mg of a pharmaceutical composition comprising an IL-4R antagonist as an initial dose followed by one or more secondary doses. In certain embodiments, the initial dose and the one or more secondary doses each comprise about 75 mg to about 300 mg of the IL-4R antagonist. In certain embodiments, the IL-4R antagonist is administered at an initial dose of 600 mg followed by one or more secondary doses wherein each secondary dose comprises 300 mg. According to this aspect of the invention, the pharmaceutical composition may be administered to the subject at a dosing frequency of, e.g., once a week, once in 2 weeks, once in 3 weeks or once in 4 weeks. In one embodiment, each secondary dose is administered 1 week after the immediately preceding dose. In one embodiment, the IL-4R antagonist is administered at an initial dose of 300 mg followed by 3-15 secondary doses wherein each secondary dose comprises 300 mg and is administered weekly.

In certain embodiments, the invention provides methods to treat or prevent skin infection in a subject wherein the skin infection is associated with an IL-4R-associated disease or disorder, for example, atopic dermatitis, asthma, or allergy. In one embodiment, the subject has moderate-to-severe atopic dermatitis.

In a related aspect, the invention provides methods for improving skin barrier function comprising administering a therapeutically effective amount of a pharmaceutical composition comprising an IL-4R antagonist to a subject in need thereof. In certain embodiments, the skin barrier function is improved in a skin lesion in a patient with atopic dermatitis. In certain embodiments, the improvement in skin barrier function upon administration of the anti-IL-4R antibody is selected from the group consisting of: (i) at least 10% increase from the baseline in Stratum Corneum Hydration (SCH) score; (ii) at least 20% decrease from the baseline in Trans-Epidermal Water Loss (TEWL) score; and (iii) a decrease in skin surface pH to acidic pH.

Exemplary IL-4R antagonists that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R antagonist is an antigen-binding protein (e.g., antibody or antigen-binding fragment thereof) that binds the IL-4Rα chain and blocks signaling by IL-4, IL-13, or both IL-4 and IL-13. In one embodiment, the antibody or antigen-binding fragment thereof that specifically binds IL-4R comprises complementarity determining regions (CDRs) in a heavy chain variable region (HCVR)/light chain variable region (LCVR) sequence pair of SEQ ID NOs: 1/2. In certain embodiments, the antibody or antigen-binding fragment thereof comprises a heavy chain CDR (HCDR1) having amino acid sequence of SEQ ID NO: 3, a HCDR2 having amino acid sequence of SEQ ID NO: 4, a HCDR3 having amino acid sequence of SEQ ID NO: 5, a light chain CDR (LCDR1) having amino acid sequence of SEQ ID NO: 6, a LCDR2 having amino acid sequence of SEQ ID NO: 7, and a LCDR3 having amino acid sequence of SEQ ID NO: 8. One such type of antigen-binding protein that can be used in the context of the methods of the present invention is an anti-IL-4Rα antibody such as dupilumab.

In some embodiments, the pharmaceutical composition is administered subcutaneously or intravenously to the patient.

In certain embodiments, the pharmaceutical composition is administered to the patient before, after or concurrent with a second therapeutic agent. In some embodiments, the second therapeutic agent is selected from the group consisting of an anti-bacterial agent, an anti-viral agent, an anti-fungal agent, another IL-4R inhibitor, an IgE inhibitor, a corticosteroid (e.g., topical corticosteroid), a non-steroidal anti-inflammatory drug (NSAID), and IFNγ.

In certain embodiments, the present invention provides use of an IL-4R antagonist of the invention in the manufacture of a medicament to treat or reduce or prevent a skin infection in a patient.

Other embodiments of the present invention will become apparent from a review of the ensuing detailed description.

DETAILED DESCRIPTION

Figure 1:
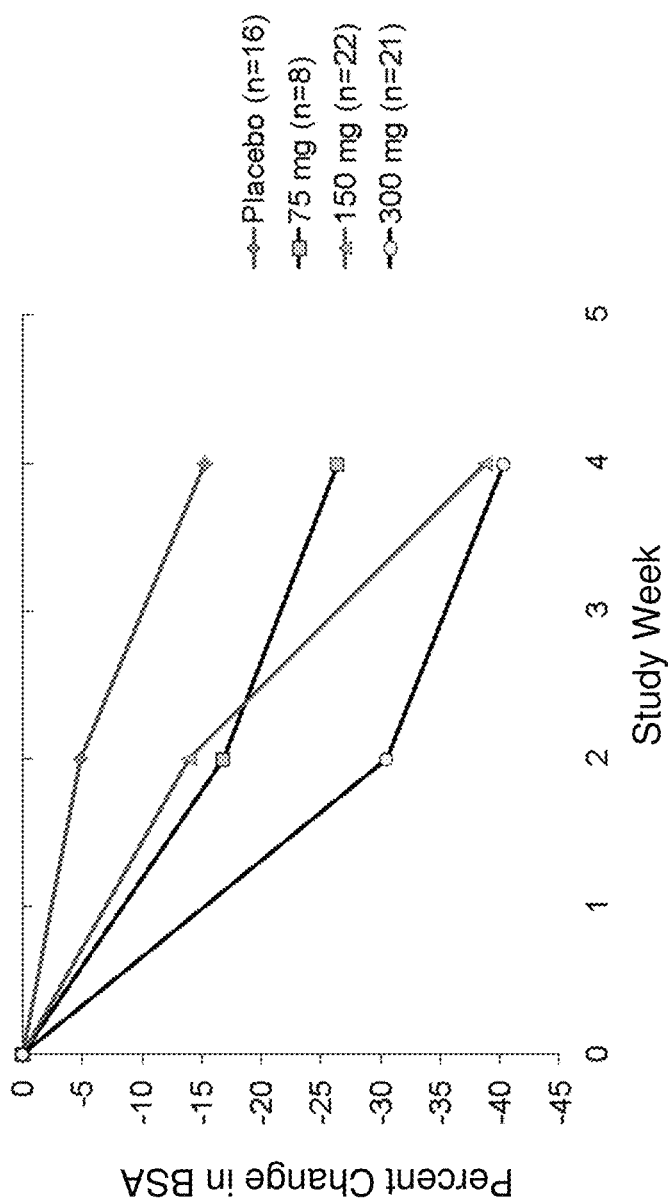
FIG. 1 shows percent change from baseline in BSA in patients administered 75 mg, 150 mg or 300 mg of anti-IL-4R antibody vs. placebo for the study in Example 1.
Figure 2:
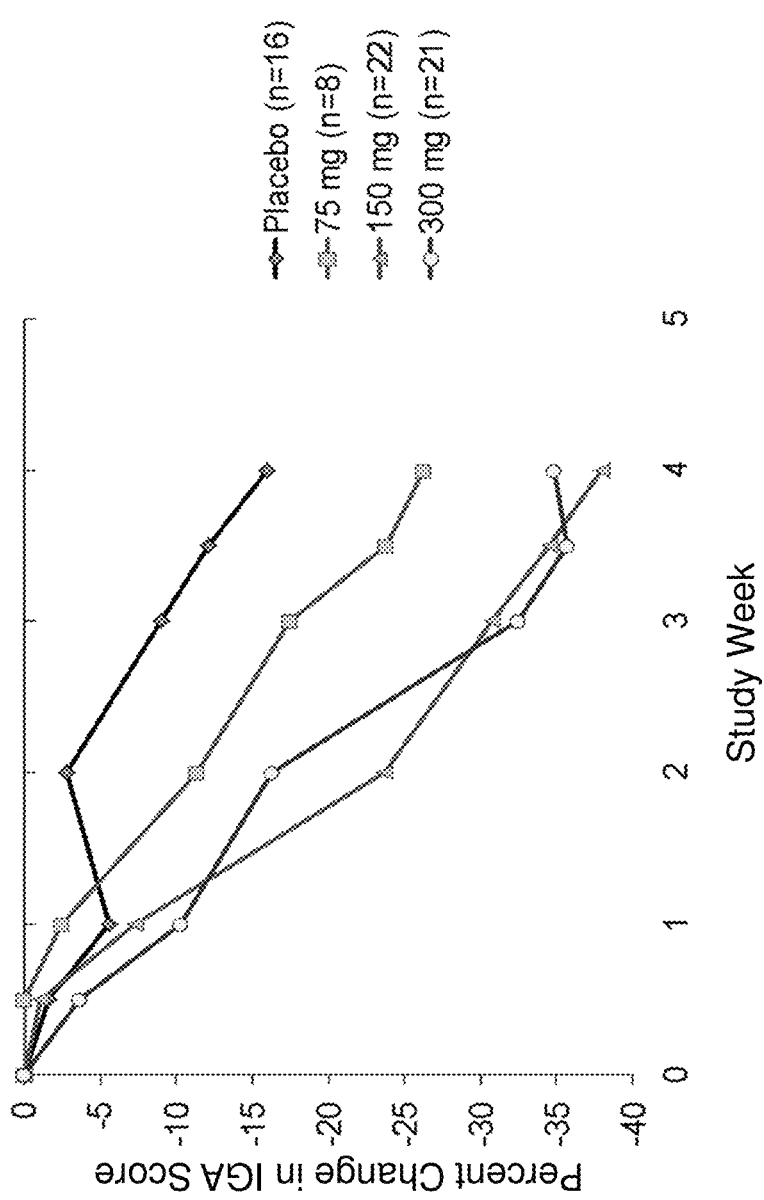
FIG. 2 shows percent change from baseline in IGA in patients administered 75 mg, 150 mg or 300 mg of anti-IL-4R antibody vs. placebo for the study in Example 1.
Figure 3:
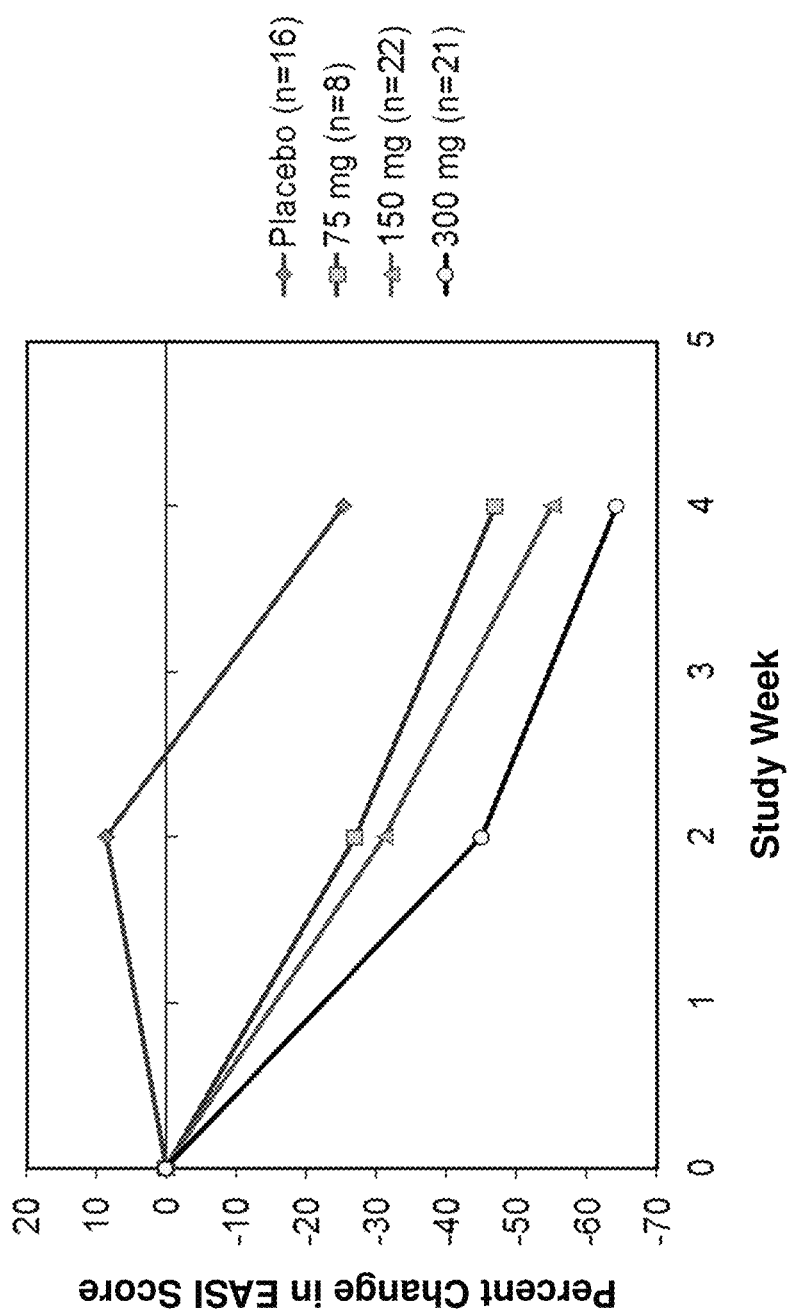
FIG. 3 shows percent change from baseline in EASI in patients administered 75 mg, 150 mg or 300 mg of anti-IL-4R antibody vs. placebo for the study in Example 1.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All publications mentioned herein are incorporated herein by reference to describe in their entirety.

Methods for Treating, Preventing or Ameliorating Skin Infections

The present invention includes methods that comprise administering to a subject in need thereof a therapeutic composition comprising an IL-4R antagonist. As used herein, the expression "a subject in need thereof" means a human or a non-human animal that exhibits one or more symptoms of a skin infection, and/or who has been diagnosed with a skin infection.

In the context of the invention, the term "subject" includes a subject with a skin infection wherein the skin infection is selected from the group consisting of impetigo, cellulitis, infected dermatitis, eczema herpeticum, folliculitis, infected blister, mycosis, tinea versicolor, *Staphylococcus aureus* infection, and *Streptococcus* infection.

In certain embodiments, the methods of the invention may be used to reduce inflammation, and/or pruritus due to a skin microbial infection.

In certain embodiments, the term "subject" includes subjects with an IL-4R-related disease or disorder, e.g., atopic dermatitis, asthma or allergy.

The present invention provides methods to reduce microbial colonization of the skin comprising administering a therapeutically effective amount of an IL-4R antagonist. As used herein, the term "subject" includes a subject infected with a microbe including, but not limited to *Staphylococcus aureus*, *Streptococcus* spp., *Pseudomonas aeruginosa*, *Bacteroides* spp., Herpes simplex virus, coxsackievirus, molluscum contagiosum virus, vaccinia virus, *Candida albicans*, *Microsporum* spp., *Trichophyton* spp., *Penicillium* spp., *Cladosporium* spp., *Alternaria* spp., and *Aspergillus* spp. In certain embodiments, the invention provides for methods to reduce colonization of *S. aureus* on the skin of patients with atopic dermatitis. In some embodiments, the microbial colonization is reduced by at least 10%, at least 15%, at least 20%, at least 25%, at least 30%, at least 35%, at least 40%, at least 45%, at least 50%, at least 55%, at least 60%, at least 65%, at least 70%, or at least 75% as compared to the baseline, upon administration of the IL-4R antagonist.

Microbial colonization may be measured with tests and procedures known in the art, e.g., by PCR, microbial culture, microscopy and staining or immunofluorescence. In certain embodiments, microbial colonization may be measured by the presence of microbial protein biomarkers known in the art, e.g., microbial toxin such as staph toxic shock syndrome toxin-1. Methods for detecting and/or quantifying such biomarkers are known in the art.

In certain embodiments, the term "subject" includes a subject co-infected with one or more microbes, e.g., a subject co-infected with herpes simplex virus and *S. aureus*.

The present invention includes methods for reducing susceptibility to a skin infection in a subject. As used herein, the term "subject" refers to subjects with increased susceptibility to a skin infection or at greater risk of developing a skin infection, e.g., subjects with atopic dermatitis. In this aspect, the term "subject" includes subjects with severe atopic dermatitis, greater allergen sensitization, and subjects with asthma or food allergy. The term "subject" also includes subjects with elevated levels of serum total and allergen-specific IgE, or serum chemokines (e.g., CCL17 or CCL27).

Methods for Improving Skin Barrier Function

The present invention includes methods for improving skin barrier function in a subject comprising administering a therapeutically effective amount of an IL-4R antagonist to the subject in need thereof. The "skin barrier function" refers to the protective function of the skin due to the structural permeability barrier of the stratum corneum layer and the secretion of anti-microbial peptides. The permeability barrier as well as the anti-microbial defense collapse or fail when the integrity of the skin is breached due to a skin infection or due to a disease such as atopic dermatitis. As used herein, the term "subject" may include subjects with a reduced skin barrier function or subjects who, prior to treatment, exhibit (or have exhibited) one or more parameters of skin barrier function. For example, the term "subject", as used herein, includes subjects with diminished production of skin anti-microbial peptides.

Examples of parameters of skin barrier function include: (a) stratum corneum hydration (SCH), (b) transepidermal water loss (TEWL), (c) skin surface pH, and (d) skin roughness profilometry (Eberlein-Konig et al 2000, Acta Derm. Venereol. 80: 188-191). SCH and TEWL may be measured by corneometry and evaporimetry methods known in the art (e.g., Vergananini et al 2010, J. Dermatol. Treatment, 21: 126-129).

To determine whether skin barrier function parameter has "improved," the parameter is quantified at baseline and at one or more time points after administration of the pharmaceutical composition of the present invention. For example, a parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the parameter.

Stratum corneum hydration (SCH): measurements of SCH are performed with a corneometer that registers electrical capacitance of the skin surface as a measurement of skin hydration. The higher the capacitance, the more hydrated the skin. According to certain embodiments of the present invention, administration of an IL-4R antagonist to a patient results in an increase in SCH score. In certain embodiments, the increase in SCH score is at least 10%, at least 20%, at least 30%, at least 40%, at least 50%, at least 60%, or at least 70% as compared to the baseline.

Transepidermal water loss (TEWL): TEWL is recorded using evaporimetry. The higher the measurement, the greater the loss of water from the skin. According to certain embodiments of the present invention, administration of an IL-4R antagonist to a patient results in a decrease in TEWL score. In certain embodiments, the decrease is at least 5%, at least 15%, at least 25%, at least 35%, at least 45%, at least 55%, at least 65%, or at least 75% as compared to the baseline.

Skin surface pH: Skin surface pH is measured with a pH meter. Skin surface pH increases due to several kinds of skin inflammation, including due to infection. According to certain embodiments of the present invention, administration of an IL-4R antagonist to a patient results in a decrease in skin surface pH to acidic pH. In certain embodiments, administration of the IL-4R antagonist to a patient results in a decrease in pH to pH 6.0, pH 5.9, pH 5.8, pH 5.7, pH 5.6, pH 5.5, pH 5.4, pH 5.3, pH 5.2, pH 5.1, pH 5.0, pH 4.9, pH 4.8, pH 4.7, pH 4.6, or pH 4.5.

Skin roughness: Skin roughness is measured using a profilometer. Profiles of the skin roughness are obtained as electrical signs. Skin roughness is increased in conditions of skin infection and atopic dermatitis. According to certain embodiments of the present invention, administration of an IL-4R antagonist to a patient results in a decrease in skin roughness.

In certain embodiments, the term "subject" includes subjects with a protein or gene or gene probe ("biomarker") associated with skin barrier function that may be differentially expressed due to reduced skin barrier function. For example, genes that are up-regulated in a subject with skin infection may include genes for markers of epidermal proliferation such as K16, Ki67; and genes that are down-regulated may include genes for terminal differentiation proteins such as filaggrin, loricrin or involucrin. In certain embodiments, the term "subject" refers to a patient with a disease or disorder such as atopic dermatitis. In particular embodiments, the term may include subjects with severe, allergen-driven (or extrinsic) AD disease.

According to certain aspects of the invention, methods for treating a skin infection or for improving skin barrier function are provided which comprise: (a) selecting a subject who exhibits a level of at least one parameter or a biomarker prior to or at the time of treatment which signifies the disease state; and (b) administering to the subject a pharmaceutical composition comprising a therapeutically effective amount of an IL-4R antagonist. The level of the biomarker is determined or quantified by acquiring a sample from the patient for a biomarker assay known in the art. In certain other embodiments, a patient is selected by acquiring information relating to an elevated level of a biomarker from the patient.

Interleukin-4 Receptor Antagonists

The methods of the present invention comprise administering to a subject in need thereof a therapeutic composition comprising an interleukin-4 receptor (IL-4R) antagonist. As used herein, an "IL-4R antagonist" (also referred to herein as an "IL-4R inhibitor," an "IL-4Rα antagonist," an "IL-4R blocker," an "IL-4Rα blocker," etc.) is any agent that binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 9. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor.

Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

According to certain exemplary embodiments of the present invention, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; $V_H$-$C_H$2-$C_H$3; (vii) $V_H$-$C_L$; $V_L$-$C_H$1; (ix) $V_L$-$C_H$2; (v) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab[2] bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In some embodiments, the anti-IL-4R antibody or antigen-binding fragment thereof comprises an HCVR comprising SEQ ID NO: 1 and an LCVR comprising SEQ ID NO: 2. According to certain exemplary embodiments, the methods of the present invention comprise the use of the anti-IL-4Rα antibody comprising HCDR1-HCDR2-HCDR3-LCDR1-LCDR2-LCDR3 amino acid sequences of SEQ ID NOs: 3-4-5-6-7-8 (referred to and known in the art as "dupilumab"), or a bioequivalent thereof.

In certain embodiments, the methods of the present invention comprise the use of an anti-IL-4R antibody, wherein the antibody comprises a heavy chain comprising the amino acid sequence of SEQ ID NO: 10. In some embodiments, the anti-IL-4R antibody comprises a light chain comprising the amino acid sequence of SEQ ID NO: 11. An exemplary antibody comprising a heavy chain comprising the amino acid sequence of SEQ ID NO: 10 and a light chain comprising the amino acid sequence of SEQ ID NO: 11 is the fully human anti-IL-4R antibody known as dupilumab. According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Rα antibodies that can be used in the context of the methods of the present invention include, e.g., the antibody referred to and known in the art as AMG317 (Corren et al., 2010, *Am J Respir Crit Care Med.,* 181(8): 788-796), or any of the anti-IL-4Rα antibodies as set forth in U.S. Pat. Nos. 7,186,809, 7,605,237, 7,608,693, or U.S. Pat. No. 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods that comprise administering an IL-4R antagonist to a patient, wherein the IL-4R antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in US Patent Application Publication No. 2012/0097565.

Dosage

The amount of IL-4R antagonist (e.g., anti-IL-4R antibody) administered to a subject according to the methods of the present invention is, generally, a therapeutically effective amount. As used herein, the phrase "therapeutically effective amount" means an amount of IL-4R antagonist that results in one or more of: (a) reduced microbial colonization, including reduced colonization of *S. aureus* on the skin; (b) improved skin barrier function; (c) reduced risk of skin inflammation due to microbial infection; and/or (d) reduced susceptibility to a skin microbial infection. A "therapeutically effective amount" also includes an amount of IL-4R antagonist that inhibits, prevents, lessens, or delays the progression of a skin infection in a subject. In certain embodiments, the phrase "therapeutically effective amount" means an amount of IL-4R antagonist that results in a detectable improvement in one or more symptoms or indicia, including reduced number of flares or exacerbations in a subject with atopic dermatitis.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 75 mg, 150 mg, or 300 mg of an anti-IL-4R antibody is administered to a subject.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods of the present invention, according to certain embodiments, comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. The term "in combination with" also includes sequential or concomitant administration of IL-4R antagonist and a second therapeutic agent.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" or with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., an antibacterial agent (including topical and systemic antibiotics, broad-spectrum and narrow-spectrum antibiotics), an antiviral agent (e.g., acyclovir, or foscarnet), an anti-fungal agent (e.g., fluconazole and econazole nitrate), another IL-4R antagonist, an IgE antagonist, interferon-gamma (IFNγ) antibiotics, topical antiseptic lotion, or any other emollient therapy or combinations thereof.

The methods of the invention comprise administering an IL-4R antagonist in combination with a second therapeutic agent for additive or synergistic activity to reduce the risk of skin infections, e.g., in a patient with AD.

Administration Regimens

The present invention includes methods comprising administering to a subject a pharmaceutical composition comprising an IL-4R antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-4R antibody, once a week dosing at an amount of about 75 mg, 150 mg, or 300 mg, can be employed.

According to certain embodiments of the present invention, multiple doses of an IL-4R antagonist may be administered to a subject over a defined time course. The methods according to this aspect of the invention comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof is 1.5×, 2×, 2.5×, 3×, 3.5×, 4×, or 5× the second amount of the antibody or antigen-binding fragment thereof. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a patient with skin infection at a loading dose of about 300 mg or about 600 mg followed by one or more maintenance doses of about 75 mg to about 300 mg. In one embodiment, the initial dose and the one or more secondary doses each include 50 mg to 600 mg of the IL-4R antagonist, e.g., 100 mg to 400 mg of the IL-4R antagonist, e.g., 100 mg, 150 mg, 200 mg, 250 mg, 300 mg, 400 mg or 500 mg of the IL-4R antagonist.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

The methods according to this aspect of the invention may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 6 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an IL-4R antagonist and a second therapeutic agent, to a patient to treat a skin infection. In some embodiments, the present methods comprise administering one or more doses of an IL-4R antagonist followed by one or more doses of a second therapeutic agent. For example, one or more doses of about 75 mg to about 300 mg of the IL-4R antagonist may be administered after which one or more doses of a second therapeutic agent (e.g., an antibiotic or any other therapeutic agent, as described elsewhere herein) may be administered to treat, alleviate, reduce or ameliorate inflammation due to a skin microbial infection. In some embodiments, the IL-4R antagonist is administered at one or more doses resulting in improved skin barrier function followed by the administration of a second therapeutic agent to reduce pathogenic microbial flora on the skin. Alternative embodiments of the invention pertain to concomitant administration of an IL-4R antagonist and a second therapeutic agent. For example, one or more doses of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary IL-4R antagonist used in the following Examples is the human anti-IL-4R antibody referred to in the art as dupilumab, wherein the antibody comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8 (also referred to herein as "mAb1").

Example 1: Treatment of Patients with Moderate-to-Severe Atopic Dermatitis with Anti-IL-4R Antibody: Analysis of Pooled Phase 1b Studies AD efficacy parameters were measured and pooled for analysis from two separate clinical trials in patients with moderate-to-severe AD. "Study A" was a 12-week, double-blind, randomized, placebo-controlled, sequential ascending dose study to assess the safety and tolerability of administered anti-IL-4R antibody (mAb1) in patients with atopic dermatitis. The treatment period was 4 weeks with patients being followed for 8 weeks after the end of the treatment period. Patients were randomized in a 4:1 ratio to receive mAb1 or placebo in each of the three ascending dose cohorts (75 mg, 150 mg, or 300 mg). The study consisted of a screening period (day −14 to day −3), a treatment period (day 1 through day 29), and a follow-up period (day 29 through day 85). During the treatment period, patients were seen in the clinic once weekly for safety, laboratory and clinical effect assessments on days 1, 4, 8, 15, 22, 25 and 29

(week 4). Patients received a dose of mAb1 or placebo on days 1, 8, 15 and 22. The end of the treatment period study was on day 29 (week 4). Patients were monitored at the study site for 6 hours after the injection (of mAb1 or placebo) on day 1, and for 3 hours after the injection on days 8, 15 and 22. During the follow-up period, patients were seen in the clinic for follow-up assessments at days 36, 43, 50, 57, 64, 71, and 85 (end of study visit).

"Study B" was a 12-week, double-blind, randomized, placebo-controlled, sequential ascending, repeated-dose study in patients with moderate-to-severe AD. AD subjects were administered 150 mg or 300 mg of mAb1, or placebo on days 1, 8, 15 and 22 of the study (four weekly doses). All administrations for both studies were subcutaneous.

The patient inclusion criteria for the studies were: (1) should be male or female 18 years; (2) have chronic atopic dermatitis for 3 years; (3) have EASI≥12; (4) IGA≥3; (5)≥15% BSA of AD involvement (in the US) or ≥10% BSA of AD involvement (ex-US); and (6) history of inadequate response to stable regimen of topical corticosteroids (TCS) or calcineurin inhibitors.

The patient exclusion criteria for the study were: (1) WBC<3.5×$10^3$/μl; (2) platelets<125×$10^3$/μl; (3) neutrophils<1.75×$10^3$/μl; (4) AST/ALT>1.5×ULN; (5) positive for hepatitis B or hepatitis C; and (6) treatment with TCS or calcineurin inhibitors within 1 week of baseline.

The primary endpoint of the studies was to monitor incidence of treatment-emergent adverse events (TEAEs) from baseline through week 12. The exploratory endpoints for efficacy variables were: (i) % achieving an IGA of 0 or 1 through week 4; (ii) % improvement in BSA and EASI from baseline; and (iii) change from baseline in NRS scale.

The exploratory efficacy variables measured in this study included: (1) proportion of patients who achieved an investigator's global assessment (IGA) score of 0 or 1 through week 4 and each study visit; (2) change and percent change in body surface area involvement of atopic dermatitis (BSA), eczema area and severity index (EASI), SCORAD, and 5-D pruritus scale from baseline to each visit; (3) weekly change from baseline in pruritus numeric rating scale (NRS); (4) change from baseline in circulating eosinophils, TARC, eotaxin-3, and total IgE through week 4; (5) change from baseline in circulating eosinophils, TARC, eotaxin-3, and total IgE through week 12; and (6) change from baseline in eosinophils, TARC, eotaxin-3, Phadiatop™ results, and total IgE associated with response through week 4.

Baseline for efficacy variable is defined as the last non-missing value on or before the date of randomization. For the patient who has no value on or before his/her randomization date the last non-missing value on or before the date of first dose injection will be used as baseline.

Investigator's Global Assessment (IGA): The IGA is an assessment scale used in clinical studies to determine severity of AD and clinical response to treatment based on a 6-point scale ranging from 0 (clear) to 5 (very severe). The IGA score was assessed at every clinic visit.

Body Surface Area Involvement of Atopic Dermatitis (BSA): BSA affected by AD was assessed for each major section of the body (head, trunk, upper extremities, and lower extremities) and was reported as the total of percentage from each body sections. Patients were assessed for BSA at the following visits: screening, day 1/baseline (pre-dose), and days 15, 29, 36, 43, 57, 71, and 85 (end of study) or early termination.

Eczema Area and Severity Index (EASI): The EASI is a validated measure used in clinical practice and clinical trials to assess the severity and extent of AD (Hanifin et al 2001, Exp. Dermatol. 10: 11-18). The EASI score calculation is based upon the Physician's Assessment of Individual Signs [erythema (E), induration/papulation (I), excoriation (X), and lichenification (L)], where each sign is scored as 0=Absent, 1=Mild, 2=Moderate, or 3=Severe, and also upon the Area Score [based on the % (BSA) affected] where 0=0% BSA, 1=1-9% BSA, 2=10-29% BSA, 3=30-49% BSA, 4=50-69% BSA, 5=70-89% BSA, 6=90-100% BSA.

For each of major section of the body (head, upper extremities, trunk and lower extremities), EASI score=(E+I+X+L)×Area Score. The total EASI score is the weighted total of the section EASI using the weights 10%=head, 20%=upper extremities, 30%=trunk, 40%=lower extremities. The minimum possible EASI score is 0 and the maximum possible EASI score is 72 where a higher score indicates increased severity of atopic dermatitis. Achieving an EASI 50 (50% or greater improvement in EASI score is considered by dermatology investigators to a clinically significant level of improvement to use as an endpoint.

Patients underwent EASI score assessment at the following visits: screening, day 1/baseline (pre-dose), and days 15, 29, 36, 43, 57, 71, and 85 (end of study) or early termination.

SCORAD: The SCORAD is a validated tool used in clinical research and clinical practice that was developed to standardize the evaluation of the extent and severity of AD (Dermatology 1993, 186: 23-31). The extent of AD is assessed as a percentage of each defined body area and reported as the sum of all areas, with a maximum score of 100% (assigned as "A" in the overall SCORAD calculation). The severity of 6 specific symptoms (erythema, oedema/papulation, excoriations, lichenification, oozing/crusts and dryness) of AD is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the patient or relative on a visual analogue scale (VAS), where 0 is no itch (or sleeplessness) and 10 is the worst imaginable itch (or sleeplessness), with a maximum possible score of 20. This parameter is assigned as "C" in the overall SCORAD calculation. The SCORAD score is calculated as A/5+7B/2+C. The maximum SCORAD score is 103.

Patients underwent SCORAD assessment at the following visits: screening, day 1/baseline (pre-dose), and days 15, 29, 36, 43, 57, 71, and 85 (end of study) or early termination.

5-D Pruritus Scale: The 5-D Pruritus Scale is a 5-question tool used in clinical trials to assess 5 dimensions of background itch: degree, duration, direction, disability, and distribution (Elman et. al. 2010, Brit. J. Dermatol. 162: 587-593). Patients rate their symptoms over the preceding 2-week period as "present" or on a 1 to 5 scale, with 5 being the most affected for each question in degree, duration, direction and disability. Single-item domain scores (duration, degree and direction) are equal to the value indicated below the response choice (range 1-5).

The disability domain includes four items that assess the impact of itching on daily activities: sleep, leisure/social activities, housework/errands and work/school. The score for the disability domain is achieved by taking the highest score on any of the four items.

For the distribution domain, the number of affected body parts is tallied (potential sum 0-16) and the sum is sorted into five scoring bins: sum of 0-2=score of 1, sum of 3-5=score of 2, sum of 6-10=score of 3, sum of 11-13=score of 4, and sum of 14-16=score of 5.

The scores of each of the five domains are achieved separately and then summed together to obtain a total 5-D score. 5-D scores can potentially range between 5 (no pruritus) and 25 (most severe pruritus).

Patients underwent 5-D pruritus assessment at the following visits: screening, day 1/baseline (pre-dose), and days 15, 29, 43, 57, 71, and 85 (end of study) or early termination.

Pruritus Numeric Rating Scale (NRS): The Pruritus NRS is a single-question assessment tool that was used to assess the patient's worst itch as a result of AD in the previous 12 hours. Patients call in to the IVRS twice daily from the evening of the screening visit and be asked the following question, "on a scale of 0-10, with 0 being 'no itch' and 10 being the 'worst itch imaginable', how would you rate your worst degree of itch experienced during the previous 12 hours?" Patients are instructed on using the IVRS to record their Pruritus NRS score at the screening visit and are queried for compliance at each following clinic visit. Patients complete the rating scale twice daily through the last study visit.

The baseline NRS is defined as the average of the reported NRSs during right after the screening visit and right before the baseline visit. For post-baseline NRS, The mean weekly NRS is calculated as the average of the reported daily NRS within the week (prorated mean).

The IGA, BSA, EASI and SCORAD scores were assessed at every clinic visit. Patients underwent 5-D pruritus assessment at the following visits: screening, day 1/baseline (pre-dose), and days 15, 29, 43, 57, 71, and 85 (end of study) or early termination. Patients used the IVRS to record their Pruritus NRS score twice daily through the last study visit.

Baseline for efficacy variable is defined as the last non-missing value on or before the date of randomization. For the patient who has no value on or before his/her randomization date the last non-missing value on or before the date of first dose injection will be used as baseline.

The baseline demographics for the patient population are presented below in Table 1.

TABLE 1

| | Baseline Demographics | | | | |
|---|---|---|---|---|---|
| | Placebo (N = 16) | 75 mg (N = 8) | 150 mg (N = 22) | 300 mg (N = 21) | All Doses (N = 51) |
| Mean age, years (SD) | 37.4 (17.16) | 35.8 (12.51) | 42.5 (11.37) | 45.4 (15.92) | 42.6 (13.73) |
| Race, n (%) | | | | | |
| Caucasian | 13 (81.3%) | 4 (50.0%) | 19 (86.4%) | 16 (76.2%) | 39 (76.5%) |
| Non-Caucasian | 3 (18.7%) | 4 (50.0%) | 3 (13.6%) | 5 (23.8%) | 12 (23.5%) |
| Gender, n (%) | | | | | |
| Male | 11 (68.8%) | 6 (75.0%) | 12 (54.5%) | 10 (47.6%) | 28 (54.9%) |
| Female | 5 (31.3%) | 2 (25.0%) | 10 (45.5%) | 11 (52.4%) | 23 (45.1%) |
| Mean BMI, kg/m$^3$ (SD) | 25.69 (5.993) | 26.41 (4.489) | 25.68 (3.991) | 27.71 (8.667) | 26.63 (6.361) |

The mean baseline disease characteristics are given in Table 2.

TABLE 2

| | Mean Baseline Disease Characteristics | | | | |
|---|---|---|---|---|---|
| | Placebo (N = 16) | 75 mg (N = 8) | 150 mg (N = 22) | 300 mg (N = 21) | All Doses (N = 51) |
| Duration of chronic AD, years | 31.8 (18.67) | 24.5 (16.95) | 32.1 (15.44) | 30.7 (16.95) | 30.4 (16.19) |
| EASI score | 22.8 (12.02) | 36.9 911.75) | 30.0 (17.00) | 27.4 (11.21) | 30.0 (14.19) |
| IGA score | 3.6 (0.72) | 4.1 (0.35) | 3.9 (0.68) | 3.5 (0.51) | 3.8 (0.62) |
| % BSA of AD | 40.3 (25.77) | 64.4 917.03) | 49.8 (28.75) | 48.2 (22.26) | 51.4 (24.87) |
| 5-D pruritus scale | 16.9 (3.94) | 21.5 (3.55) | 19.0 (2.94) | 18.7 (3.64) | 19.3 (3.41) |
| Pruritus NRS score | 5.8 (1.75) | 7.0 (1.78) | 6.0 (1.82) | 5.7 (1.51) | 6.0 (1.72) |

The exploratory efficacy results obtained from the pooled studies are summarized in Tables 3-11 and in FIGS. 1-8.

TABLE 3

Summary of subjects achieving IGA ≤ 1 at Day 29 and all study visits

Number and % subjects with IGA ≤ 1

| | Placebo (N = 16) | 75 mg (N = 8) | 150 mg (N = 22) | 300 mg (N = 21) | All Doses Combined (N = 51) |
|---|---|---|---|---|---|
| Week 4, Day 29 | 1 (6.3%) | 0 | 4 (18.2%) | 2 (9.5%) | 6 (11.8%) |
| Day 4 | 0 | 0 | 0 | 0 | 0 |
| Week 1, Day 8 | 0 | 0 | 0 | 0 | 0 |
| Week 2, Day 15 | 0 | 0 | 0 | 1 (4.8%) | 1 (2.0%) |
| Week 3, Day 22 | 0 | 0 | 0 | 2 (9.5%) | 2 (3.9%) |
| Week 3, Day 25 | 1 (6.3%) | 0 | 1 (4.5%) | 4 (19.0%) | 5 (9.8%) |
| Week 5, Day 36 | 1 | 0 | 4 (18.2%) | 2 (9.5%) | 6 (11.8%) |
| Week 6, Day 43 | 2 (12.5%) | 0 | 5 (22.7%) | 3 (14.3%) | 8 (15.7%) |
| Week 7, Day 50 | 2 (12.5%) | 0 | 4 (18.2%) | 3 (14.3%) | 7 (13.7%) |
| Week 8, Day 57 | 2 (12.5%0 | 0 | 3 (13.6%) | 5 (23.8%) | 8 (15.7%) |
| Week 9, Day 64 | 1 (6.3%) | 0 | 3 (13.6%) | 4 (19.0%) | 7 (13.7%) |
| Week 10, Day 71 | 1 (6.3%) | 0 | 1 (4.5%) | 5 (23.8%) | 6 (11.8%) |
| Week 12, Day 85 | 1 (6.3%) | 0 | 0 | 3 (14.3%) | 3 (5.9%) |

TABLE 4

Summary of Percentage and Absolute Change in BSA Score from Baseline - all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline BSA Score | 40.3 (25.77) | 64.4 (17.03) | 49.8 (28.75) | 48.2 (22.26) | 51.4 (24.87) |
| Day 15 BSA Score | 37.6 (26.61) | 52.3 (12.54) | 40.9 (25.66) | 34.4 (22.66) | 40.0 (23.23) |
| % Change from Baseline to Day 15 | −4.8 (14.80) | −16.8 (15.17) | −13.9 (21.77) | −30.5 (27.09) | −21.4 (24.27) |
| Absolute change from Baseline to Day 15 | −1.7 (5.37) | −12.1 (11.58) | −7.0 (15.07) | −13.9 (14.73) | −10.7 (14.51) |
| Day 29 BSA Score | 31.1 (29.69) | 46.3 (12.42) | 31.1 (28.78) | 31.5 925.33) | 33.8 (25.47) |
| % Change from Baseline to Day 29 | −15.3 (31.02) | −26.4 (16.41) | −38.8 (37.00) | −40.3 (33.78) | −37.4 (32.88) |
| Absolute change from Baseline to Day 29 | −2.1 (10.93) | −18.1 (13.14) | −18.2 (24.61) | −16.7 (16.05) | −17.5 (19.31) |
| Day 36 BSA Score | 25.1 (26.81) | 41.2 (15.59) | 24.9 (24.15) | 26.0 (22.67) | 28.0 (22.70) |
| % Change from Baseline to Day 36 | −13.3 (39.22) | −33.7 (21.53) | −48.6 (32.13) | −44.2 (34.61) | −44.4 (31.41) |
| Absolute change from Baseline to Day 36 | −1.8 (10.33) | −22.4 (15.26) | −24.3 (25.07) | −18.0 (17.82) | −21.6 (20.85) |
| Day 43 BSA Score | 29.9 (27.04) | 48.4 (21.56) | 24.8 (26.36) | 26.2 (21.03) | 29.1 (24.42) |
| % Change from Baseline to Day 43 | −11.0 (39.52) | −29.2 (24.87) | −43.3 (42.81) | −47.2 (30.07) | −42.7 (35.05) |
| Absolute change from Baseline to Day 43 | −2.0 (10.74) | −19.0 (15.63) | −22.2 (29.35) | −19.8 (14.41) | −20.7 (21.52) |
| Day 57 BSA Score | 27.2 (31.12) | 57.5 (23.40) | 31.2 (28.60) | 28.3 (20.11) | 33.7 (26.24) |
| % Change from Baseline to Day 57 | −33.6 (32.95) | −18.7 (23.06) | −37.4 (42.74) | −41.9 (29.38) | −36.6 (35.90) |
| Absolute change from Baseline to Day 57 | −8.3 (16.62) | −12.4 (16.36) | −20.0 (28.38) | −17.6 (13.86) | −18.0 (21.99) |
| Day 71 BSA Score | 27.4 (28.13) | 58.4 (19.79) | 30.7 (24.56) | 23.2 (19.85) | 31.1 (24.32) |
| % Change from Baseline to Day 71 | −29.0 (36.38) | −13.2 (11.92) | −35.7 (37.54) | −52.0 (35.43) | −39.9 (36.13) |
| Absolute change from Baseline to Day 71 | −7.5 (17.71) | −8.5 (8.10) | −18.4 (23.12) | −25.2 (18.53) | −20.1 (20.14) |
| Day 85 BSA Score | 25.1 (27.73) | 58.0 (19.52) | 30.7 (28.38) | 23.6 (17.95) | 30.7 (25.04) |
| % Change from Baseline to Day 85 | −33.4 (32.68) | −16.9 (16.63) | −37.8 (43.59) | −49.0 (37.34) | −40.4 (39.14) |
| Absolute change from Baseline to Day 85 | −8.4 (14.45) | −11.9 (11.45) | −20.6 (29.67) | −22.7 (15.74) | −20.5 (22.31) |

TABLE 5

Summary of Percentage and Absolute Change in EASI Score from Baseline - all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline EASI Score | 22.8 (12.02) | 36.9 (11.75) | 30.0 (17.00) | 27.4 (11.21) | 30.0 (14.19) |
| Day 15 EASI Score | 25.4 (20.13) | 26.2 (7.72) | 19.8 (15.05) | 15.4 (8.57) | 19.0 (12.06) |
| % Change from Baseline to Day 15 | 8.7 (66.05) | −26.9 (19.29) | −31.1 (27.24) | −45.1 (19.90) | −36.3 (24.02) |
| Absolute change from Baseline to Day 15 | 2.8 (14.11) | −10.7 (9.83) | −9.7 (12.02) | −12.0 (6.93) | −10.8 (9.67) |
| Day 29 EASI Score | 17.2 (15.11) | 17.7 (6.05) | 13.1 (11.89) | 11.3 (11.84) | 13.1 (11.17) |
| % Change from Baseline to Day 29 | −25.4 (34.98) | −47.0 (21.93) | −55.0 (30.36) | −64.3 (25.83) | −57.7 (27.45) |
| Absolute change from Baseline to Day 29 | −3.6 (7.25) | −19.2 (15.11) | −16.6 (14.58) | −16.1 (7.69) | −16.8 (11.97) |
| Day 36 EASI Score | 13.2 (11.97) | 16.3 (7.74) | 9.4 (10.27) | 10.5 (8.69) | 11.0 (9.42) |

TABLE 5-continued

Summary of Percentage and Absolute Change in EASI Score from Baseline - all values represented as Mean (SD)

|  | Placebo | mAb1 75 mg | mAb1 150 mg | mAb1 300 mg | All Doses Combined |
|---|---|---|---|---|---|
| % Change from Baseline to Day 36 | −28.4 (41.10) | −51.5 (25.53) | −69.6 (22.46) | −61.9 (22.69) | −63.6 (23.41) |
| Absolute change from Baseline to Day 36 | −3.9 (7.94) | −21.5 (17.30) | −20.5 (14.98) | −16.1 (8.23) | −19.0 (13.13) |
| Day 43 EASI Score | 12.9 97.13) | 19.8 (10.41) | 9.6 (11.01) | 9.3 (8.29) | 11.1 (10.32) |
| % Change from Baseline to Day 43 | −33.8 (28.94) | −39.4 (31.87) | −64.2 (33.89) | −66.4 (22.39) | −61.2 (29.98) |
| Absolute change from Baseline to Day 43 | −6.2 (4.71) | −17.0 (19.33) | −19.7 (16.63) | −16.8 (7.84) | −18.0 (13.76) |
| Day 57 EASI Score | 13.0 (11.95) | 27.0 (16.46) | 12.2 (12.88) | 10.4 (9.40) | 13.5 (13.11) |
| % Change from Baseline to Day 57 | −28.7 (62.63) | −24.5 (47.21) | −57.3 (33.38) | −61.1 (24.91) | −54.3 (33.99) |
| Absolute change from Baseline to Day 57 | −5.4 (11.79) | −11.9 (22.95) | −18.4 (17.88) | −15.8 (9.69) | −16.5 (15.81) |
| Day 71 EASI Score | 11.8 (9.22) | 28.3 (13.06) | 13.0 (10.86) | 8.5 (9.21) | 13.1 (12.06) |
| % Change from Baseline to Day 71 | −45.8 (31.06) | −14.5 (41.14) | −54.9 (32.01) | −71.3 (24.14) | −56.8 (34.68) |
| Absolute change from Baseline to Day 71 | −9.6 (8.23) | −9.4 (22.16) | −16.9 (15.41) | −19.1 (9.88) | −16.9 (14.32) |
| Day 85 EASI Score | 9.8 (4.87) | 27.1 (11.99) | 14.2 (14.30) | 10.5 (9.26) | 14.0 (12.77) |
| % Change from Baseline to Day 85 | −44.8 (30.60) | −28.3 (29.69) | −51.3 (37.58) | −63.0 (25.55) | −53.9 (32.86) |
| Absolute change from Baseline to Day 85 | −9.3 (8.01) | −13.4 (18.94) | −16.6 (17.67) | −15.4 (7.57) | −15.7 (13.81) |

TABLE 6

Summary of Percentage and Absolute Change in 5-D Pruritus Scale from Baseline - all values represented as Mean (SD)

|  | Placebo | mAb1 75 mg | mAb1 150 mg | mAb1 300 mg | All Doses Combined |
|---|---|---|---|---|---|
| No. Patients | 16 | 8 | 22 | 21 | 51 |
| Baseline 5-D Pruritus Scale | 16.9 (3.94) | 21.5 (3.55) | 19.0 (2.94) | 18.7 (3.64) | 19.3 (3.41) |
| Day 15 5-D Pruritus Scale | 15.0 (4.66) | 14.0 (3.55) | 14.0 (4.46) | 12.5 (4.08) | 13.4 (4.15) |
| % Change from Baseline to Day 15 | −5.6 (29.83) | −34.3 (15.43) | −26.6 (19.26) | −32.4 (17.60) | −30.3 (17.95) |
| Absolute change from Baseline to Day 15 | −1.4 (5.55) | −7.5 (3.82) | −5.0 (3.97) | −6.1 (3.93) | −5.9 (3.94) |
| Day 29 5-D Pruritus Scale | 14.8 93.77) | 14.1 (3.31) | 13.1 (5.03) | 11.0 (4.86) | 12.3 (4.79) |
| % Change from Baseline to Day 29 | −3.9 (20.07) | −33.0 (17.25) | −30.8 (23.71) | −40.8 (21.83) | −35.6 (22.02) |
| Absolute change from Baseline to Day 29 | −0.8 (3.41) | −7.4 (4.47) | −5.9 (4.84) | −7.7 (4.78) | −6.9 (4.73) |
| Day 43 5-D Pruritus Scale | 13.8 (3.71) | 16.5 (4.54) | 12.1 (4.64) | 10.7 (4.83) | 12.3 (5.04) |
| % Change from Baseline to Day 43 | −10.4 (31.60) | −21.4 (25.01) | −35.0 (22.07) | −40.8 (23.87) | −35.0 (23.86) |
| Absolute change from Baseline to Day 43 | −2.3 (5.25) | −5.0 (5.66) | −6.6 (4.45) | −7.6 (5.04) | −6.8 (4.90) |
| Day 57 5-D Pruritus Scale | 12.3 (3.35) | 19.9 (3.98) | 13.9 94.75) | 11.6 (5.18) | 14.0 (5.46) |
| % Change from Baseline to Day 57 | −19.0 (25.37) | −9.0 (20.15) | −27.2 (21.28) | −37.2 (21.68) | −28.1 (22.85) |
| Absolute change from Baseline to Day 57 | −3.4 (4.43) | −2.3 (4.46) | −5.1 (4.03) | −6.8 (4.61) | −5.3 (4.49) |
| Day 71 5-D Pruritus Scale | 13.5 (4.03) | 19.4 (3.51) | 15.3 (4.78) | 12.9 (5.61) | 14.7 (5.36) |
| % Change from Baseline to Day 71 | −11.6 (25.71) | −8.3 (14.91) | −18.9 (19.50) | −31.7 (24.53) | −23.3 (22.58) |
| Absolute change from Baseline to Day 71 | −2.0 (4.12) | −2.0 (3.39) | −3.4 (3.56) | −5.8 (4.70) | −4.3 (4.24) |
| Day 85 5-D Pruritus Scale | 14.1 (4.48) | 18.6 (1.34) | 15.2 (3.99) | 14.6 (5.26) | 15.3 (4.53) |
| % Change from Baseline to Day 85 | −5.4 (32.44) | −10.0 (22.58) | −18.5 (21.29) | −21.9 (23.41) | −19.0 (22.18) |
| Absolute change from Baseline to Day 85 | −1.2 (5.09) | −2.8 (4.92) | −3.7 (4.04) | −4.1 (4.52) | −3.7 (4.27) |

TABLE 7

Summary of Percentage and Absolute Change in Average Weekly NRS Score from Baseline - all values represented as Mean (SD)

|  | Placebo | mAb1 75 mg | mAb1 150 mg | mAb1 300 mg | All Doses Combined |
|---|---|---|---|---|---|
| No. Patients | 10 | 8 | 22 | 21 | 51 |
| Baseline NRS Score | 5.8 (1.75) | 7.0 (1.78) | 6.0 (1.82) | 5.7 (1.51) | 6.0 (1.72) |
| Week 1 NRS Score | 5.1 (1.73) | 5.2 (2.50) | 5.2 (1.91) | 4.3 (1.52) | 4.8 (1.88) |
| % Change from Baseline to Week 1 | −11.9 (23.13) | −27.3 (20.25) | −12.7 (18.26) | −21.6 (26.03) | −18.8 (22.42) |
| Absolute change from Baseline to Week 1 | −0.8 (1.40) | −1.7 (1.22) | −0.8 (1.30) | −1.4 (1.59) | −1.2 (1.44) |
| Week 2 NRS Score | 4.7 (2.00) | 4.0 (2.36) | 4.5 (2.38) | 3.7 (1.59) | 4.1 (2.07) |
| % Change from Baseline to Week 2 | −14.8 (36.13) | −44.6 (21.90) | −26.9 (29.96) | −33.3 (26.69) | −32.4 (27.63) |
| Absolute change from Baseline to Week 2 | −1.0 (2.16) | −3.0 (1.350) | −1.5 (1.76) | −2.0 (1.71) | −1.9 (1.73) |
| Week 3 NRS Score | 5.0 (2.29) | 3.9 (2.12) | 4.0 (2.12) | 3.3 (1.30) | 3.7 (1.81) |
| % Change from Baseline to Week 3 | −10.2 (33.75) | −45.6 (21.67) | −35.4 (23.84) | −39.4 (25.92) | −38.8 (24.17) |
| Absolute change from Baseline to Week 3 | −0.7 (2.01) | −3.1 (1.30) | −2.0 (1.49) | −2.4 (1.65) | −2.3 (1.55) |
| Week 4 NRS Score | 4.1 (2.03) | 4.1 (1.95) | 3.9 (2.38) | 3.1 (1.84) | 3.6 (2.10) |
| % Change from Baseline to Week 4 | −18.6 (40.12) | −42.3 (22.62) | −36.7 (29.33) | −45.4 (32.89) | −41.3 (29.63) |

TABLE 7-continued

Summary of Percentage and Absolute Change in Average Weekly
NRS Score from Baseline - all values represented as Mean (SD)

| | | mAb1 | | | |
| --- | --- | --- | --- | --- | --- |
| | Placebo | 75 mg | 150 mg | 300 mg | All Doses Combined |
| Absolute change from Baseline to Week 4 | −1.2 (2.29) | −2.9 (1.38) | −2.1 (1.85) | −2.6 (1.77) | −2.4 (1.74) |
| Week 5 NRS Score | 4.2 (2.29) | 4.1 (2.03) | 3.5 (2.36) | 3.0 (1.80) | 3.4 (2.09) |
| % Change from Baseline to Week 5 | −18.9 (43.93) | −41.9 (24.53) | −43.4 (30.89) | −44.2 (32.74) | −43.5 (30.09) |
| Absolute change from Baseline to Week 5 | −1.2 (2.43) | −2.9 (1.55) | −2.5 (1.97) | −2.5 (1.92) | −2.6 (1.85) |
| Week 6 NRS Score | 4.0 (2.40) | 4.1 (2.22) | 3.7 (2.38) | 3.0 (1.84) | 3.5 (2.14) |
| % Change from Baseline to Week 6 | −24.9 (42.63) | −42.7 (24.23) | −40.0 (30.52) | −46.9 (28.41) | −43.3 (28.31) |
| Absolute change from Baseline to Week 6 | −1.4 (2.36) | −2.8 (1.44) | −2.2 (1.86) | −2.6 (1.68) | −2.5 (1.71) |
| Week 7 NRS Score | 3.4 (2.59) | 4.4 (2.39) | 3.7 (2.56) | 2.8 (1.78) | 3.4 (2.26) |
| % Change from Baseline to Week 7 | −35.5 (42.70) | −41.3 (21.96) | −40.3 (33.56) | −49.9 (30.73) | −44.5 (30.73) |
| Absolute change from Baseline to Week 7 | −1.9 (2.33) | −2.8 (1.10) | −2.2 (1.90) | −2.8 (1.83) | −2.5 (1.77) |
| Week 8 NRS Score | 3.5 (2.61) | 5.4 (2.40) | 3.7 (2.24) | 3.0 (1.98) | 3.7 (2.24) |
| % Change from Baseline to Week 8 | −33.9 (38.63) | −27.8 (21.17) | −38.2 (33.09) | −45.6 (32.23) | −39.8 (31.29) |
| Absolute change from Baseline to Week 8 | −1.8 (2.19) | −1.9 (1.19) | −2.2 (1.80) | −2.6 (1.99) | −2.3 (1.80) |
| Week 9 NRS Score | 3.6 (2.26) | 5.5 (2.44) | 4.1 (2.10) | 3.0 (2.27) | 3.9 (2.32) |
| % Change from Baseline to Week 9 | −32.8 (35.28) | −26.1 (17.08) | −31.5 (32.14) | −46.2 (36.56) | −36.9 (32.95) |
| Absolute change from Baseline to Week 9 | −1.7 (2.01) | −1.7 (1.02) | −1.8 (1.59) | −2.5 (2.10) | −2.1 (1.77) |
| Week 10 NRS Score | 3.7 (2.51) | 5.3 (2.33) | 4.6 (2.18) | 3.2 (1.99) | 4.1 (2.21) |
| % Change from Baseline to Week 10 | −30.3 (41.78) | −21.7 (24.33) | −24.6 (28.77) | −43.4 (31.24) | −32.5 (30.36) |
| Absolute change from Baseline to Week 10 | −1.6 (2.31) | −1.4 (1.51) | −1.3 (1.37) | −2.4 (1.70) | −1.8 (1.59) |
| Week 11 NRS Score | 2.8 (2.03) | 5.8 (2.11) | 5.0 (2.19) | 3.2 (1.81) | 4.4 (2.23) |
| % Change from Baseline to Week 11 | −40.2 (40.04) | −13.1 (26.33) | −14.2 (36.88) | −41.2 (31.87) | −25.1 (35.60) |
| Absolute change from Baseline to Week 11 | −2.0 (2.26) | −0.9 (1.61) | −0.8 (1.72) | −2.2 (1.64) | −1.4 (1.76) |
| Week 12 NRS Score | 3.5 (1.48) | 5.2 (2.37) | 4.8 (2.47) | 3.5 (2.37) | 4.4 (2.44) |
| % Change from Baseline to Week 12 | −28.9 (29.54) | −25.4 (25.39) | −17.9 (33.42) | −35.5 (33.02) | −25.4 (32.53) |
| Absolute change from Baseline to Week 12 | −1.5 (1.66) | −1.7 (1.50) | −1.0 (1.77) | −1.7 (1.73) | −1.3 (1.71) |

TABLE 8

Summary of Percentage and Absolute Change in IGA Score from Baseline - all values represented as Mean (SD)

| | | mAb1 | | | |
| --- | --- | --- | --- | --- | --- |
| | Placebo | 75 mg | 150 mg | 300 mg | All Doses Combined |
| No. Patients | 16 | 8 | 22 | 21 | 51 |
| Baseline IGA Score | 3.6 (0.72) | 4.1 (0.35) | 3.9 (0.68) | 3.5 (0.51) | 3.8 (0.62) |
| Day 4 IGA Score | 3.6 (0.73) | 4.1 (0.35) | 3.9 (0.71) | 3.3 (0.48) | 3.7 (0.65) |
| % Change from Baseline to Day 4 | −1.6 (6.25) | 0.0 (0.00) | −1.1 (5.33) | −3.6 (8.96) | −2.0 (6.79) |
| Absolute change from Baseline to Day 4 | −0.1 (0.25) | 0.0 (0.00) | 0.0 (0.21) | −0.1 (0.36) | −0.1 (0.27) |
| Day 8 IGA Score | 3.3 (0.90) | 4.0 (0.00) | 3.6 (0.85) | 3.1 (0.54) | 3.5 (0.73) |
| % Change from Baseline to Day 8 | −5.6 (21.28) | −2.5 (7.07) | −7.3 (12.55) | −10.3 (13.67) | −7.8 (12.46) |
| Absolute change from Baseline to Day 8 | −0.2 (0.68) | −0.1 (0.35) | −0.3 (0.46) | −0.4 (0.50) | −0.3 (0.46) |
| Day 15 IGA Score | 3.4 (0.99) | 3.6 (0.52) | 3.0 (0.97) | 2.9 (0.70) | 3.1 (0.83) |
| % Change from Baseline to Day 15 | −2.8 (28.98) | −11.3 (16.20) | −23.7 (16.69) | −16.3 (18.16) | −18.5 (17.55) |
| Absolute change from Baseline to Day 15 | −0.1 (0.92) | −0.5 (0.76) | −0.9 (0.64) | −0.6 (0.60) | −0.7 (0.65) |
| Day 22 IGA Score | 3.1 (0.67) | 3.4 (0.52) | 2.7 (0.73) | 2.3 (0.80) | 2.7 (0.80) |
| % Change from Baseline to Day 22 | −9.0 (19.61) | −17.5 (15.35) | −30.8 (12.76) | −32.5 (23.99) | −29.4 (19.17) |
| Absolute change from Baseline to Day 22 | −0.3 (0.65) | −0.8 (0.710) | −1.2 (0.52) | −1.1 (0.79) | −1.1 (0.68) |
| Day 25 IGA Score | 3.0 (0.89) | 3.1 (0.35) | 2.5 (0.87) | 2.2 (0.89) | 2.5 (0.86) |
| % Change from Baseline to Day 25 | −12.1 (29.43) | −23.8 (10.94) | −34.5 (18.64) | −35.7 (25.16) | −33.2 (21.05) |
| Absolute change from Baseline to Day 25 | −0.5 (0.93) | −1.0 (0.53) | −1.4 (0.790) | −1.2 (0.83) | −1.2 (0.77) |
| Day 29 IGA Score | 2.9 (1.08) | 3.0 (0.53) | 2.4 (0.99) | 2.3 (0.85) | 2.4 (0.89) |
| % Change from Baseline to Day 29 | −16.0 (24.48) | −26.3 (16.20) | −38.0 (24.02) | −34.9 (21.18) | −34.8 (21.68) |
| Absolute change from Baseline to Day 29 | −0.5 (0.80) | −1.1 (0.83) | −1.5 (1.00) | −1.2 (0.68) | −1.3 (0.85) |
| Day 36 IGA Score | 2.9 (1.20) | 3.0 (0.58) | 2.2 (0.76) | 2.4 (0.50) | 2.4 (0.70) |
| % Change from Baseline to Day 36 | −16.7 (26.35) | −26.4 (17.49) | −44.1 (19.38) | −33.3 (9.13) | −37.1 (16.97) |
| Absolute change from Baseline to Day 36 | −0.5 (0.85) | −1.1 (0.90) | −1.7 (0.81) | −1.2 (0.40) | −1.4 (0.74) |
| Day 43 IGA Score | 2.8 (1.06) | 3.3 (0.76) | 2.3 (1.02) | 2.2 (0.83) | 2.4 (0.97) |
| % Change from Baseline to Day 43 | −21.1 (26.91) | −19.3 (21.88) | −40.8 (28.04) | −39.0 (19.85) | −36.6 (24.53) |
| Absolute change from Baseline to Day 43 | −0.8 (0.97) | −0.9 (1.07) | −1.6 (1.04) | −1.3 (0.58) | 1.4 (0.89) |
| Day 50 IGA Score | 2.7 (1.19) | 3.3 (0.82) | 2.4 (1.07) | 2.1 (0.80) | 2.4 (1.00) |
| % Change from Baseline to Day 50 | −18.9 (30.98) | −18.3 (23.80) | −37.2 (25.87) | −40.7 (21.93) | −36.0 (24.57) |
| Absolute change from Baseline to Day 50 | −0.6 (1.12) | −0.8 (1.17) | −1.5 (1.07) | −1.4 (0.70) | −1.3 (0.95) |
| Day 57 IGA Score | 2.8 (1.20) | 3.2 (0.75) | 2.5 (1.03) | 2.2 (0.97) | 2.5 (1.00) |
| % Change from Baseline to Day 57 | −17.6 (33.45) | −22.5 (22.08) | −34.8 (25.21) | −36.3 (24.99) | −33.7 (24.60) |
| Absolute change from Baseline to Day 57 | −0.6 (1.01) | −1.0 (1.10) | −1.4 (1.07) | −1.2 (0.83) | −1.3 (0.97) |
| Day 64 IGA Score | 2.7 (0.79) | 3.5 (1.05) | 2.7 (1.08) | 2.1 (0.81) | 2.6 (1.06) |
| % Change from Baseline to Day 64 | −18.9 (21.44) | −14.2 (29.23) | −30.9 (26.08) | −38.5 (20.61) | −31.5 (25.22) |

TABLE 8-continued

Summary of Percentage and Absolute Change in IGA Score from Baseline - all values represented as Mean (SD)

|  | Placebo | mAb1 | | | |
| --- | --- | --- | --- | --- | --- |
|  |  | 75 mg | 150 mg | 300 mg | All Doses Combined |
| Absolute change from Baseline to Day 64 | −0.6 (0.67) | −0.7 (1.37) | −1.2 (1.06) | −1.3 (0.70) | −1.2 (0.98) |
| Day 71 IGA Score | 2.6 (0.81) | 3.4 (0.89) | 2.8 (0.86) | 2.1 (1.15) | 2.5 (1.10) |
| % Change from Baseline to Day 71 | −22.0 (20.84) | −17.0 (26.36) | −25.5 (27.32) | −41.7 (31.65) | −32.0 (30.18) |
| Absolute change from Baseline to Day 71 | −0.7 (0.65) | −0.8 (1.300) | −1.1 (1.18) | −1.5 (1.10) | −1.2 (1.15) |
| Day 85 IGA Score | 2.6 (1.17) | 3.2 (0.84) | 2.8 (0.99) | 2.6 (0.96) | 2.8 (0.96) |
| % Change from Baseline to Day 85 | −20.8 (36.69) | −22.0 (24.65) | −25.6 (31.31) | −24.6 (28.66) | −24.7 (28.77) |
| Absolute change from Baseline to Day 85 | −0.7 (1.16) | −1.0 (1.22) | −1.1 (1.23) | −0.8 (0.90) | −1.0 (1.07) |

TABLE 9

Number (%) of subjects achieving EASI-50 at Day 29 and every study visit - LOCF

| | Number and % subjects with EASI50 | | | | |
| --- | --- | --- | --- | --- | --- |
| | Placebo (N = 16) | 75 mg (N = 8) | 150 mg (N = 22) | 300 mg (N = 21) | All Doses Combined (N = 51) |
| Week 4, Day 29 | 3 (18.8%) | 3 (37.5%) | 12 (54.5%) | 15 (71.4%) | 30 (58.8%) |
| Week 2, Day 15 | 0 | 0 | 6 (27.3%) | 11 (52.4%) | 17 (33.3%) |
| Week 5, Day 36 | 3 (18.8%) | 5 (62.5%) | 16 (72.7%) | 15 (71.4%) | 36 (70.6%) |
| Week 6, Day 43 | 3 (18.8%) | 2 (25.0%) | 14 (63.6%) | 16 (76.2%) | 32 (62.7%) |
| Week 8, Day 57 | 5 (31.3%) | 2 (25.0%) | 12 (54.5%) | 13 (61.9%) | 27 (52.9%) |
| Week 10, Day 71 | 6 (37.5%) | 1 (12.5%) | 13 (59.1%) | 16 (76.2%) | 30 (58.8%) |
| Week 12, Day 85 | 3 (18.8%) | 1 (12.5%) | 12 (54.5%) | 17 (81.0%) | 30 (58.8%) |

TABLE 10

Number (%) of subjects achieving EASI-25 at Day 29 and every study visit - LOCF

| Number and % subjects with EASI25 | Placebo (N = 16) | 75 mg (N = 8) | 150 mg (N = 22) | 300 mg (N = 21) | All Doses Combined (N = 51) |
| --- | --- | --- | --- | --- | --- |
| Week 4, Day 29 | 4 (25.0%) | 7 (87.5%) | 16 (72.7%) | 18 (85.7%) | 41 (80.4%) |
| Week 2, Day 15 | 3 (18.8%) | 5 (62.5%) | 13 (59.1%) | 16 (76.2%) | 34 (66.7%) |
| Week 5, Day 36 | 6 (37.5%) | 7 (87.5%) | 19 (86.4%) | 18 (85.7%) | 44 (86.3%) |
| Week 6, Day 43 | 7 (43.8%) | 5 (62.5%) | 19 (86.4%) | 18 (85.7%) | 42 (82.4%) |
| Week 8, Day 57 | 8 (50.0%) | 4 (40.0%) | 16 (72.7%) | 17 (81.0%) | 37 (72.5%) |
| Week 10, Day 71 | 8 (50.0%) | 3 (37.5%) | 17 (77.3%) | 19 (90.5%) | 39 (76.5%) |
| Week 12, Day 85 | 9 (56.3%) | 3 (37.5%) | 16 (72.7%) | 20 (95.2%) | 39 (76.5%) |

TABLE 11

Number (%) of subjects achieving EASI-75 at Day 29 and every study visit - LOCF

Figure 4:
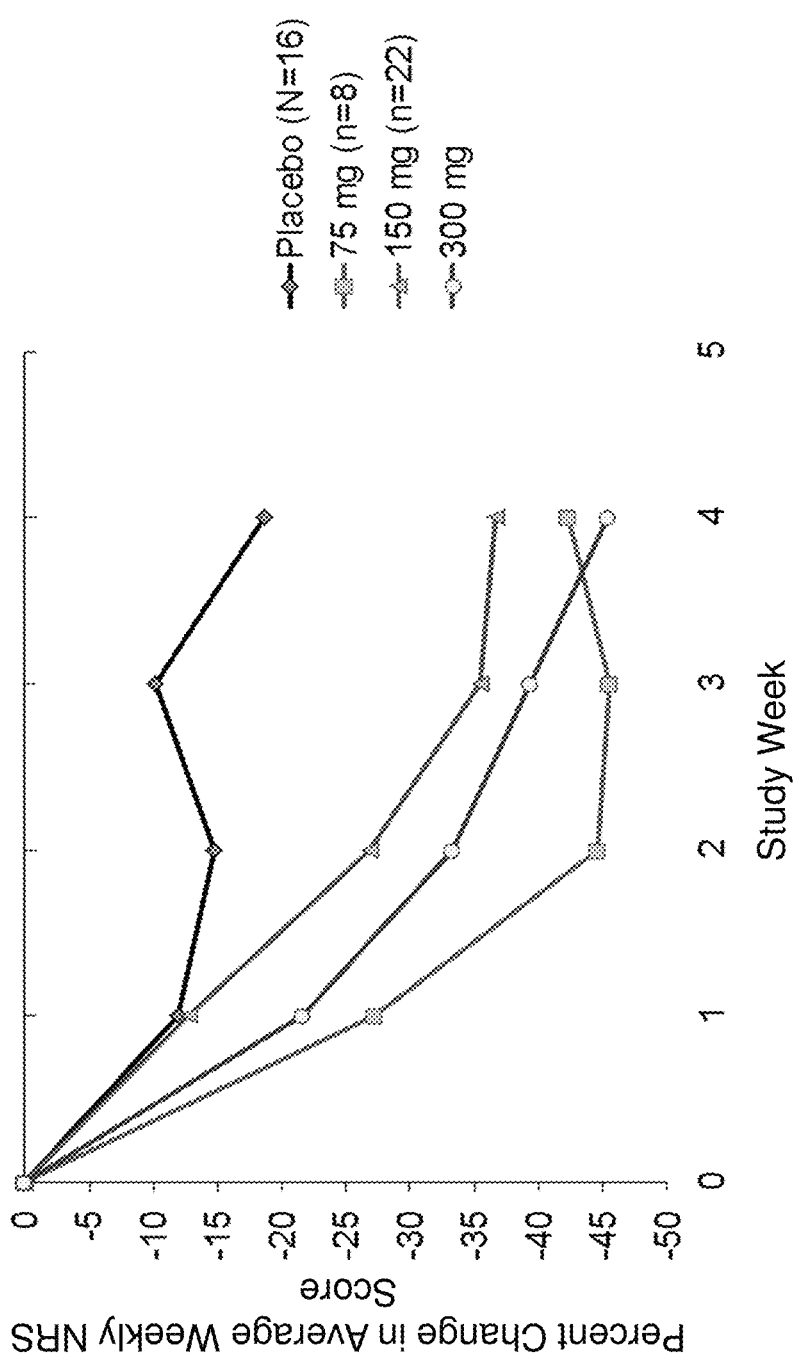
FIG. 4 shows percent change from baseline in Pruritus NRS in patients administered 75 mg, 150 mg or 300 mg of anti-IL-4R antibody vs. placebo for the study in Example 1.
Figure 5:
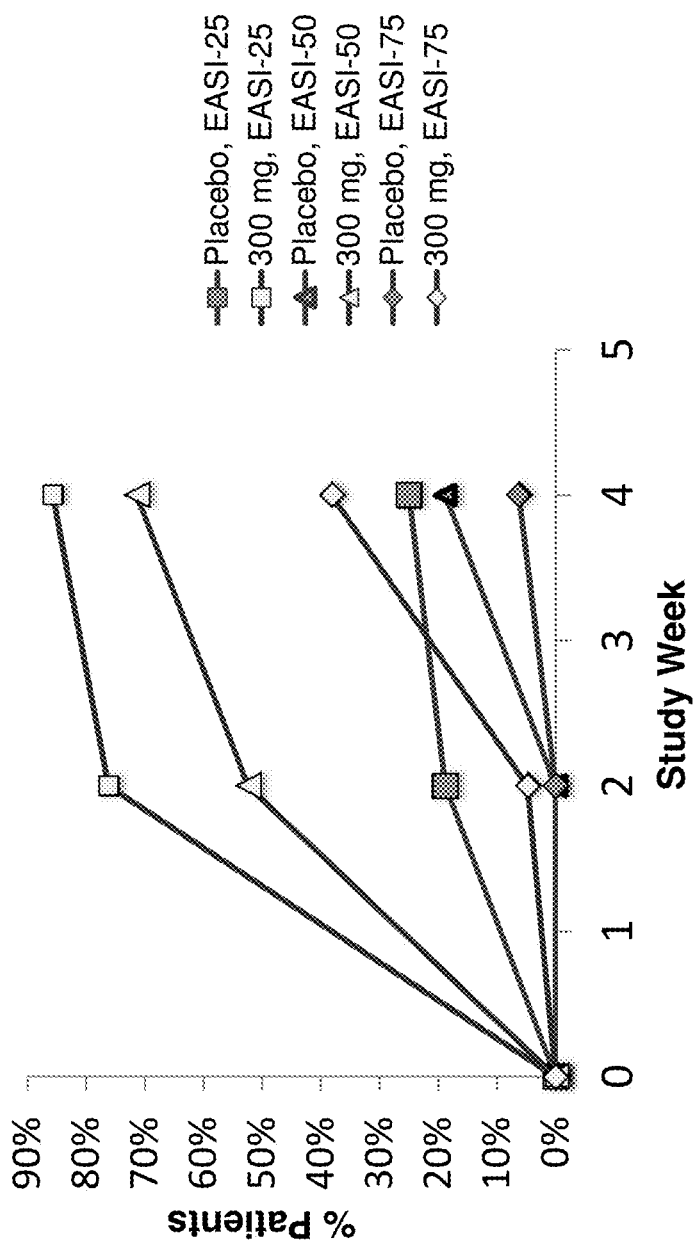
FIG. 5 shows EASI response time course in patients with moderate-to-severe AD to 300 mg anti-IL-4R antibody for the study in Example 1.
Figure 6:
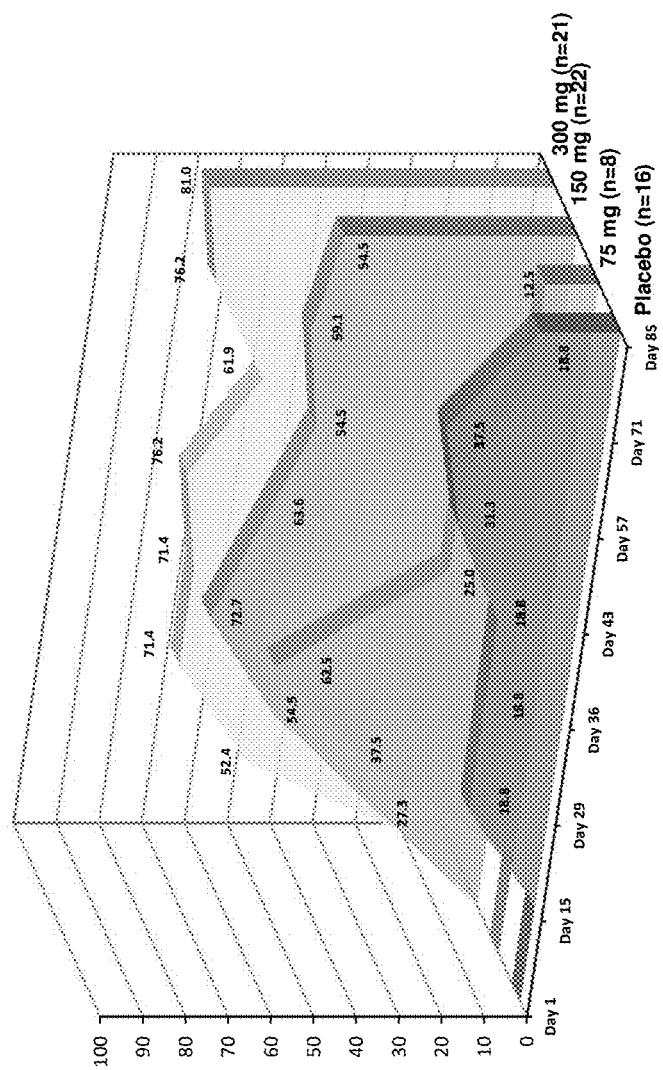
FIG. 6 shows the percent responders in the EASI score administered with 75 mg, 150 mg or 300 mg anti-IL-4R antibody vs. placebo for the study in Example 1.
Figure 7:
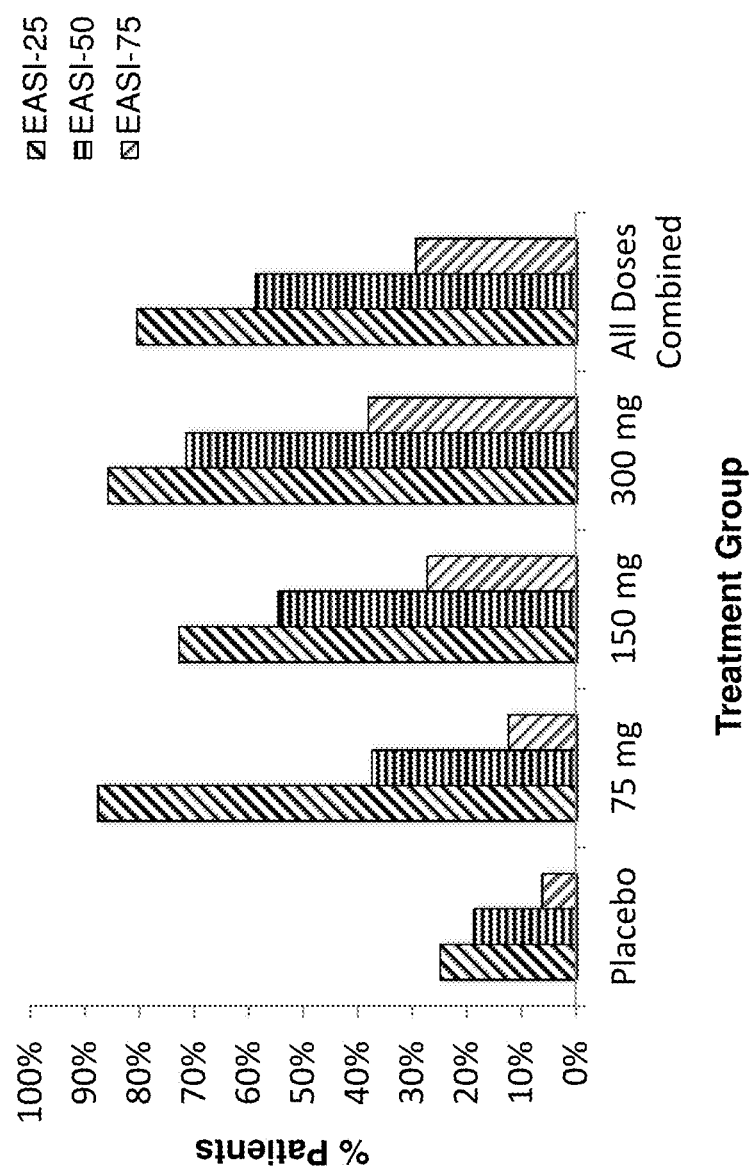
FIG. 7 shows EASI responses at week 4 (day 29) to anti-IL-4R antibody administered at 75 mg, 150 mg or 300 mg doses vs. placebo for the study in Example 1.

| Number and % subjects with EASI75 | Placebo (N = 16) | 75 mg (N = 8) | 150 mg (N = 22) | 300 mg (N = 21) | All Doses Combined (N = 51) |
| --- | --- | --- | --- | --- | --- |
| Week 4, Day 29 | 1 (6.3%) | 1 (12.5%) | 6 (27.3%) | 8 (38.1%) | 15 (29.4%) |
| Week 2, Day 15 | 0 | 0 | 1 (4.5%) | 1 (4.8%) | 2 (3.9%) |
| Week 5, Day 36 | 1 (6.3%) | 1 (12.5%) | 9 (40.9%) | 7 (33.3%) | 17 (33.3%) |
| Week 6, Day 43 | 1 (6.3%) | 1 (12.5%) | 8 (36.4%) | 6 (28.6%) | 15 (29.4%) |
| Week 8, Day 57 | 2 (12.5%) | 1 (12.5%) | 9 (40.9%) | 6 (28.6%) | 16 (31.4%) |
| Week 10, Day 71 | 2 (12.5%) | 1 (12.5%) | 6 (27.3%) | 11 (52.4%) | 18 (35.5%) |
| Week 12, Day 85 | 2 (12.5%) | 1 (12.5%) | 6 (27.3%) | 7 (33.3%) | 14 (27.5%) | mAb1 was well-tolerated and effective in adults with moderate-to-severe AD. mAb1 administration significantly improved AD disease activity and severity. At 4 weeks, 150 mg and 300 mg mAb1 achieved significant improvements vs. placebo for change from baseline in % BSA (p<0.05) (FIG. 1), IGA (p<0.001) (FIG. 2), EASI (p<0.001) (FIG. 3), and pruritus NRS (p<0.01, 300 mg) (FIG. 4). More patients had 50% reduction in EASI score with 150 mg mAb1 (54.5%) and with 300 mg (71.4%) vs. placebo (18.8%; p<0.05 for both) (FIGS. 5 and 6). More patients achieved EASI-25, EASI-50, and EASI-75 with mAb1 over placebo at week 4 (FIG. 7).

Figure 8:
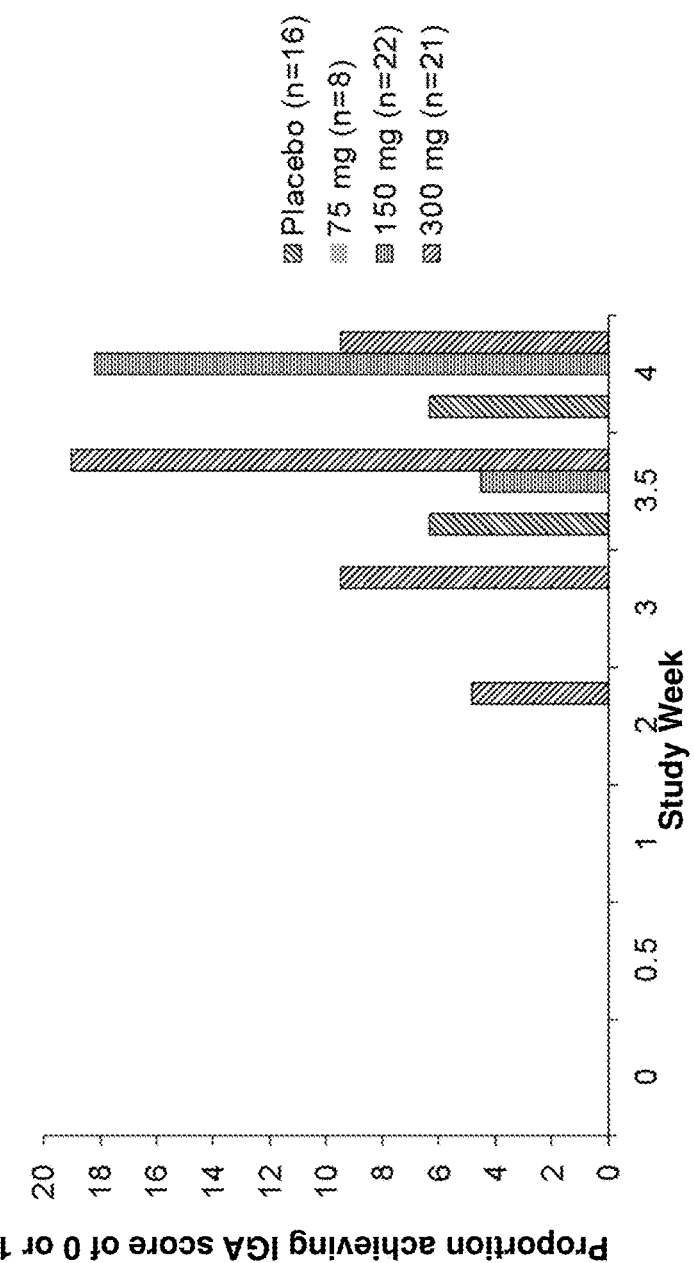
FIG. 8 shows proportion of patients achieving IGA≤1 for the study in Example 1.
Figure 9:
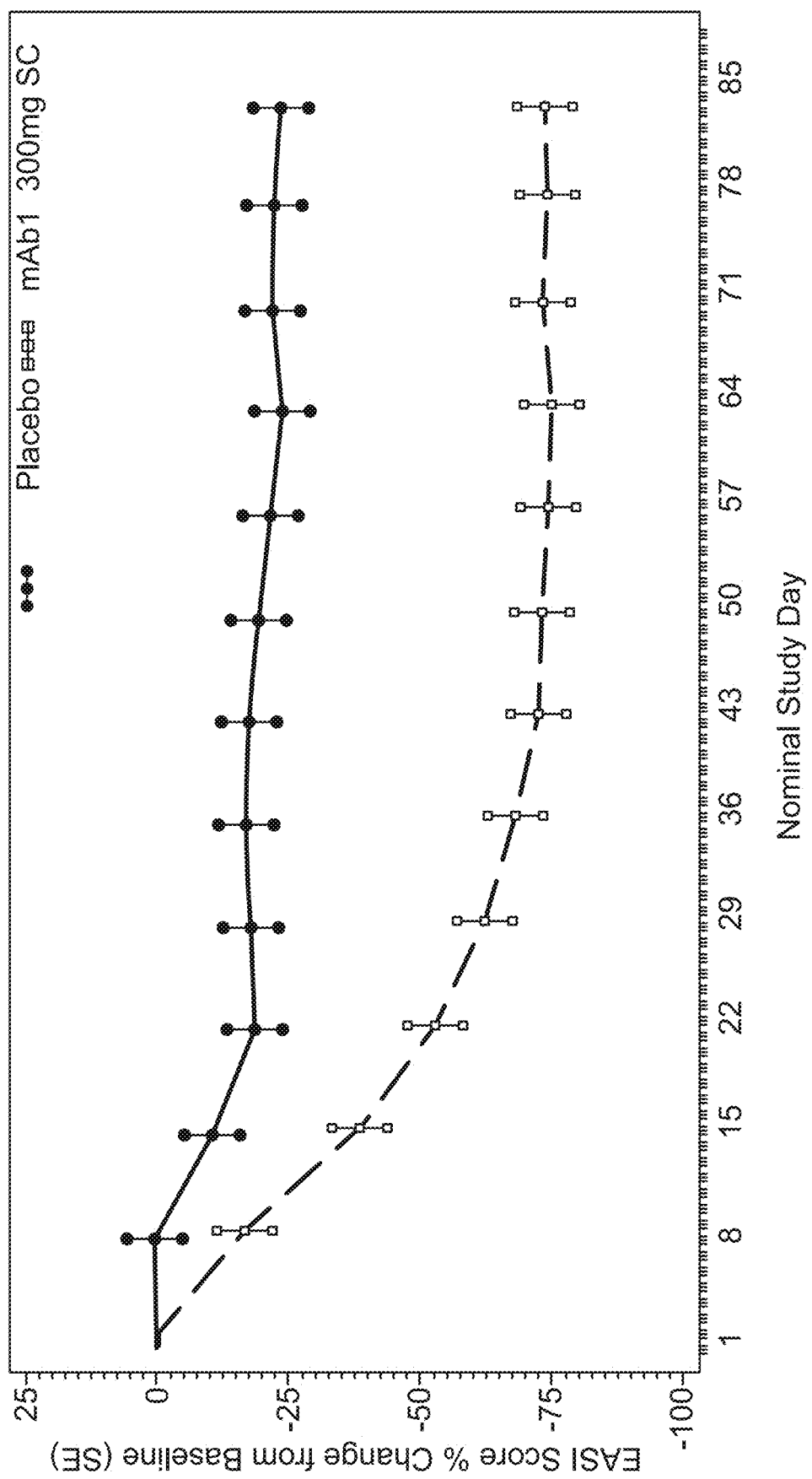
FIG. 9 shows mean EASI score percent change from baseline to the last observation carried forward (LOCF) for the study in Example 2.
Figure 10:
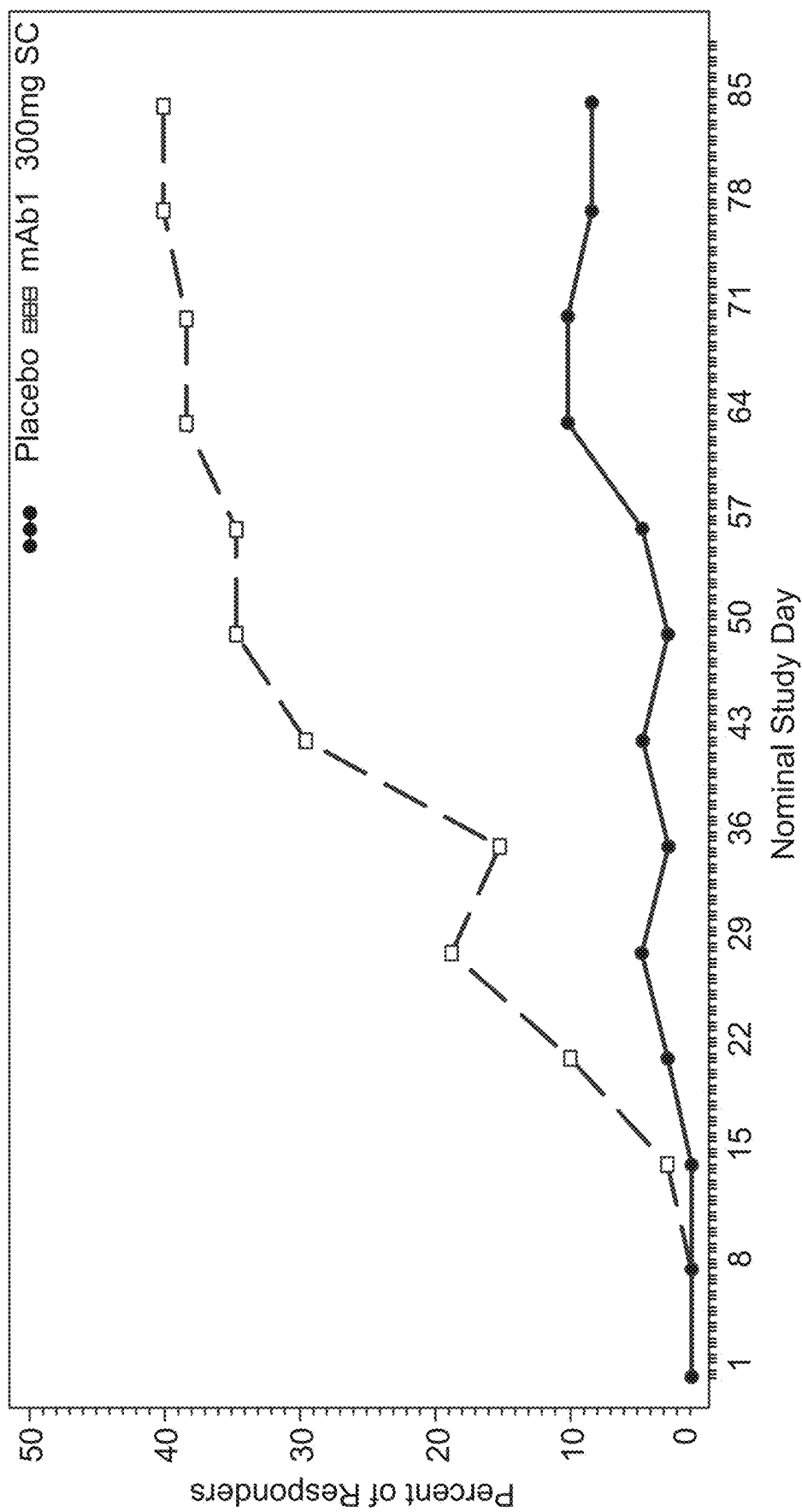
FIG. 10 shows IGA score responder rate 9 score of 0 or 1) up to LOCF for the study in Example 2.
Figure 11:
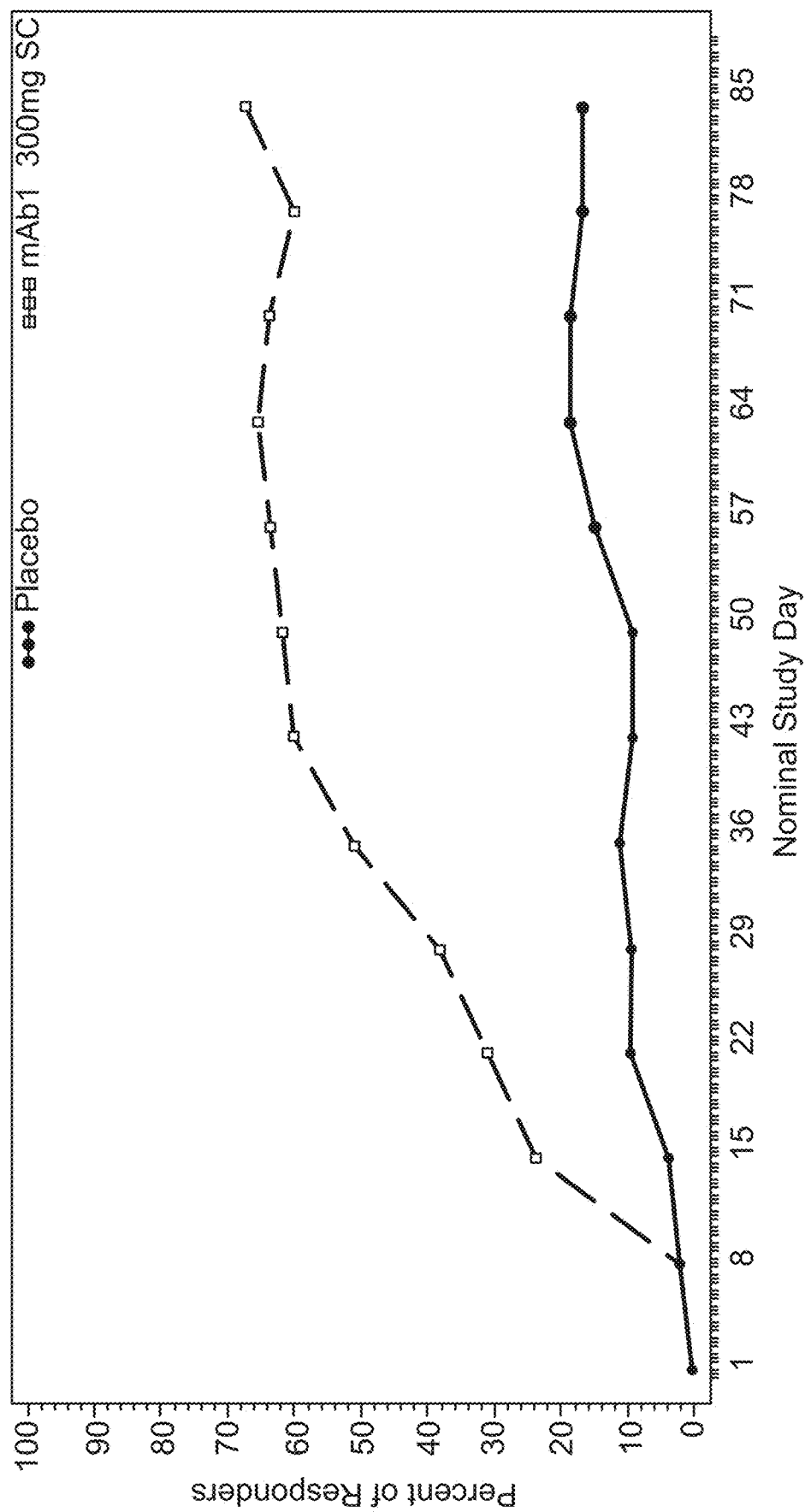
FIG. 11 shows IGA score responder rate (reduction in score of 2 or more) up to LOCF for the study in Example 2.
Figure 12:
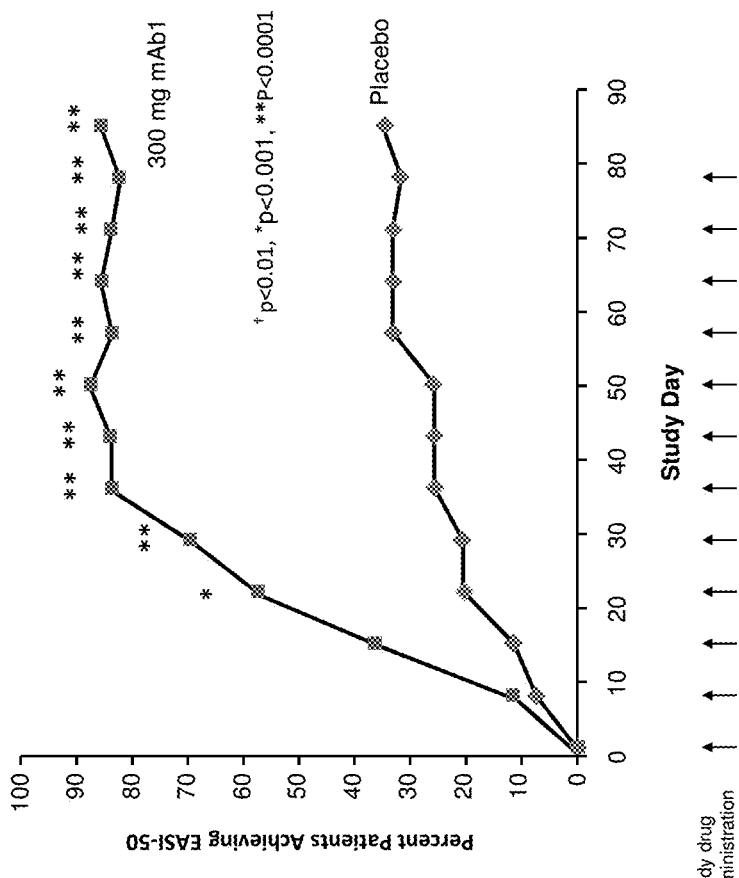
FIG. 12 shows EASI score responder rate (50% score reduction from baseline) up to LOCF for the study in Example 2.
Figure 13:
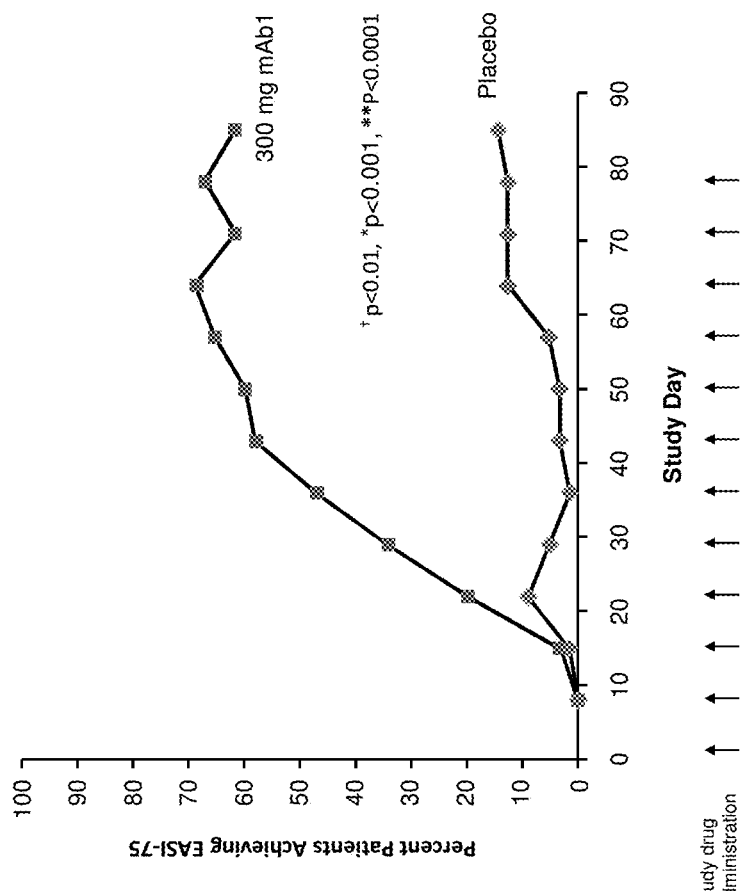
FIG. 13 shows EASI score responder rate (75% score reduction from baseline) up to LOCF for the study in Example 2.
Figure 14:
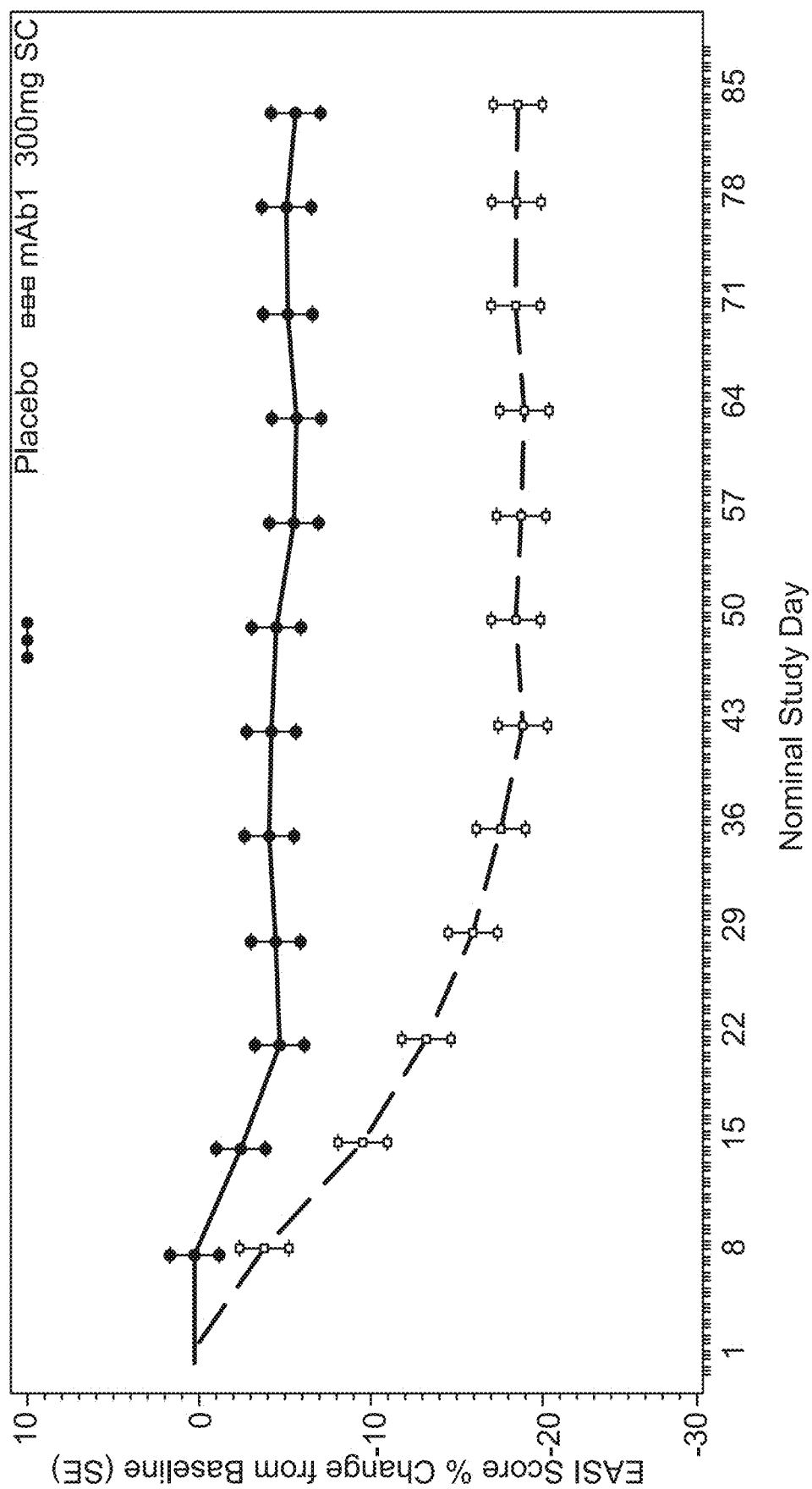
FIG. 14 shows mean EASI score change from baseline up to LOCF for the study in Example 2.

For 300 mg mAb1, significant improvement was seen within 2 weeks in % BSA (p<0.02), IGA (p<0.05), and EASI (p<0.0001). Improvements for BSA, IGA and EASI (p<0.05 vs. placebo) were maintained for 8 weeks. The proportion of patients with IGA 0 or 1 at week 4 was higher than placebo, but not statistically significant (FIG. 8).

The most common treatment-emergent adverse events (AEs) with mAb1 administration were nasopharyngitis (19.6% vs. 12.5% for placebo) and headache (11.8% vs. 6.3% for placebo).

Example 2: Repeat-Dose Clinical Trial of Subcutaneously Administered Anti-IL-4R Antibody (mAb1) in Adult Patients with Moderate-to-Severe Atopic Dermatitis A. Study Design This study was a 28-week randomized, double-blind, placebo-controlled study of the anti-IL-4R mAb, referred herein as "mAb1", administered subcutaneously in patients with moderate-to-severe atopic dermatitis. The treatment period was 12 weeks in duration with the patients followed for a further 16 weeks after end of the treatment.

109 patients were included and randomized in the ratio of 1:1 for the study (54 in placebo and 55 for 300 mg of the antibody). 43 patients (30 in placebo and 13 in 300 mg group) withdrew from the study. Randomization was stratified according to IgE levels (IgE<150 kU/L vs.≥150 kU/L at the screening visit) to test the efficacy of mAb1 in patients with extrinsic or intrinsic form of AD. Patients who met eligibility criteria underwent day 1/baseline assessments, randomization, and then received 300 mg of mAb1 or placebo SC. Each weekly dose of study drug was given as one 2-mL injection, or was split into two 1-mL injections. Patients returned for weekly clinic visits and received an injection of study drug on days 8, 15, 22, 29, 36, 43, 50, 57, 64, 71, and 78. Patients were closely monitored at the study site for a minimum of 2 hours after each dose of study drug. The end of the treatment period was day 85. Follow-up visits occurred on days 92, 99, 106, 113, 120, 127, 134, 141, 148, 155, 162, 169, 176, 183, 190, and the end of study visit on day 197.

Inclusion criteria for the study were as follows: (1) Male or female 18 years or older; (2) Chronic AD, diagnosed by the Eichenfield revised criteria of Hannifin and Rajka, that has been present for at least 3 years before the screening visit; (3) EASI score≥16 at the screening and baseline visits; (4) IGA score≥3 at the screening and baseline visits; (5)≥10% BSA of AD involvement at the screening and baseline visits; (6) history of inadequate response to a stable 1 month) regimen of topical corticosteroids or calcineurin inhibitors as treatment for AD within the last 3 months before the screening visit; (7) Patients must have applied a stable dose of an additive-free, basic bland emollient twice-daily for at least 7 days before the baseline visit; and (8) Willingness, commitment, and ability to return for all clinic visits and complete all study-related procedures and willing and able to sign the informed consent form (ICF).

Exclusion criteria for the study were as follows: (1) Prior treatment with mAb1; (2) Presence of any of the following laboratory abnormalities at the screening visit: white blood cell count <3.5×10$^3$/μL; platelet count <125×10$^3$/μL; neutrophil count <1.75×10$^3$/μL; aspartate aminotransferase (AST)/alanine aminotransferase (ALT)>1.5× the ULN; and CPK>2× the ULN; (3) Positive or indeterminate results at the screening visit for hepatitis B surface antigen, hepatitis B core antibody or hepatitis C antibody; (4) Onset of a new exercise routine or major change to a previous exercise routine within 4 weeks prior to screening (visit 1). Subjects had to be willing to maintain a similar level of exercise for the duration of the study and to refrain from unusually strenuous exercise for the duration of the trial; (5) Treatment with an investigational drug within 8 weeks or within 5 half-lives, if known, whichever is longer, before the baseline visit; (6) Treatment with a live (attenuated) vaccine within 12 weeks before the baseline visit; (7) Treatment with allergen immunotherapy within 6 months before the baseline visit; (8) Treatment with leukotriene inhibitors within 4 weeks before the baseline visit; (9) Treatment with systemic corticosteroids within 4 weeks before the baseline visit; (10) Treatment with topical corticosteroids, tacrolimus, and/or pimecrolimus within 1 week before the baseline visit; (11) Systemic treatment for AD with an immunosuppressive/immunomodulating substance, e.g. Cyclosporine, mycophenolate-mofetil, IFN-γ, phototherapy, (narrow band uvB, uvB, uvA1, psoralen+uvA), azathioprine, methotrexate, or biologics, within 4 weeks before the baseline visit; (12) three or more bleach baths during any week within the 4 weeks before the baseline visit; (13) Treatment of AD with a medical device (e.g. Atopiclair®, MimyX®, Epicerum®, Cerave®, etc.) within 1 week before the baseline visit; (14) Chronic or acute infection requiring treatment with oral or IV antibiotics, antivirals, anti-parasitics, anti-protozoals, or anti-fungals within 4 weeks before the screening visit, or superficial skin infections within 1 week before the screening visit; (15) Known history of HIV infection; (16) History of hypersensitivity reaction to doxycycline or related compounds; (17) History of clinical parasite infection, other than vaginal trichomoniasis; (18) History of malignancy within 5 years before the baseline visit, with the following exceptions; patients with a history of completely treated carcinoma in situ of cervix, and non-metastatic squamous or basal cell carcinoma of the skin are allowed; (19) Planned surgical procedure during the length of the patient's participation in the study; (20) Use of a tanning booth/parlor within 4 weeks before the screening visit; (21) Significant concomitant illness or history of significant illness such as psychiatric, cardiac, renal, neurological, endocrinological, metabolic or lymphatic disease, or any other illness or condition that would have adversely affected the subject's participation in this study; (22) Pregnant or breast-feeding women; and/or (23) Unwilling to use adequate birth control. Adequate birth control is defined as agreement to consistently practice an effective and accepted method of contraception throughout the duration of the study and for 16 weeks after last dose of study drug. For females, adequate birth control methods are defined as: hormonal contraceptives, intrauterine device (IUD), or double barrier contraception (i.e., condom+diaphragm, condom or diaphragm+spermicidal gel or foam). For males, adequate birth control methods are defined as: double barrier contraception (i.e., condom+diaphragm, condom or diaphragm+spermicidal gel or foam). For females, menopause is defined as 24 months without menses; if in question, a follicle-stimulating hormone of 25 U/mL must be documented. Hysterectomy, bilateral oophorectomy, or bilateral tubal ligation must be documented, as applicable.

B. Efficacy Variables

The primary endpoint was the percent change in EASI score from baseline to week 12. The secondary endpoints measured in this study included: (1) proportion of patients who achieved an investigator's global assessment (IGA) score of 0 or 1 at week 12; (2) proportion of patients who achieved ≥50% overall improvement in EASI score (also called EASI 50) from baseline to week 12; (3) change in EASI score from baseline to week 12; (4) change and percent change in IGA score, body surface area involvement of atopic dermatitis (BSA), eczema area and severity index (EASI), SCORAD, Pruritus NRS and 5-D pruritus scale from baseline to week 12; (5) Incidence of TEAEs from baseline through week 28; (6) change from baseline in eosinophils, TARC, Phadiatop™ results, and total IgE associated with response; (7) change in QoLIAD from baseline to week 12; (8) proportion of patients who achieve reduction of IGA score of ≥2 from baseline to week 12; (9) proportion of patients who achieve reduction of IGA score of ≥3 from baseline to week 12; and (10) PD response of circulating eosinophils, TARC and total IgE.

Baseline for efficacy variable is defined as the last non-missing value on or before the date of randomization. For the patient who has no value on or before his/her randomization date the last non-missing value on or before the date of first dose injection will be used as baseline.

Investigation Procedures

The efficacy variables IGA, BSA, EASI, SCORAD, 5-D Pruritus scale, and Pruritus NRS rating have been described elsewhere herein (see Example 1).

The IGA, BSA, EASI and SCORAD scores were assessed at every clinic visit. Patients underwent 5-D pruritus assessment at the following visits: screening, day 1/baseline (pre-dose), and days 15, 29, 43, 57, 71, 85, 99, 113, 127, 141, 155, 169, 183 and 197 (end of study) or early termination. Patients used the IVRS to record their Pruritus NRS score twice daily through the last study visit.

Quality of Life Index for Atopic Dermatitis (QoLIAD): The QoLIAD is a 25-item, validated questionnaire used in clinical practice and clinical trials to assess the impact of AD disease symptoms and treatment on QoL (Whalley et al 2004, Br. J. Dermatol. 150: 274-283; Meads et al 2005, Value Health 8: 331-332). The format is a simple yes/no response to 25 items with a scoring system of 0 to 25; a high score is indicative of a poor QoL. The analysis is sensitive to change with a 2-3 point difference considered as clinically meaningful. The questionnaire was administered to a subset of patients at screening and day 1/baseline (pre-dose), and days 29, 57, 85, and 197 (end of study) or early termination. The differences between treatments were compared using an analysis of covariance model (ANCOVA) with relative baseline as a covariate.

C. Investigational Treatment mAb1 drug product was supplied as a lyophilized powder in a 5 ml glass vial for SC administration. When delivered SC, the mAb1 drug product was reconstituted with 2.5 ml of sterile water for injection, yielding a solution containing 150 mg/mL of mAb1. The dose level of mAb1 tested was 300 mg for SC administration. mAb1 or placebo was administered as 1 (2 mL) or 2 (1 mL) SC injections in the clinic on day 1/baseline and days 8, 15, 22, 29, 36, 43, 50, 57, 64, 71, and 78. Although it was preferred that each weekly dose of study drug be given as one 2-mL injection, each weekly dose could be split into two 1-mL injections. Subcutaneous injection sites were alternated between the following sites: back of arms, abdomen (except the navel or waist area), and upper thighs. Administration to the extremities was not allowed due to the possibility of different absorption and bioavailability. If administration of multiple injections were required on the same day, each injection was delivered at a different injection site (e.g., 1 injection administered in the right lower quadrant of the abdomen and the other in the left lower quadrant of the abdomen). Subcutaneous injection sites were alternated so that the same sites were not injected for 2 consecutive weeks.

Placebo matching mAb1 was prepared in the same formulation as mAb1, but without addition of antibody.

Patients were monitored at the study site for a minimum of 2 hours after each dose of study drug.

In addition, patients were required to apply stable doses of an additive-free, basic bland emollient twice daily for at least 7 days before the baseline visit and throughout study participation. Patients reported compliance with background treatment during the study using the IVRS or IWRS. The system prompted patients to answer the following question about emollient use: "Did you use a moisturizer approved by the study doctor on the affected areas of your skin?"

D. Safety Assessment

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

In addition, laboratory safety variables, vital sign variables, 12-lead electrocardiography (ECG) variables, and physical examination variables were measured throughout the study.

The clinical laboratory data consists of hematology, blood chemistry and urinalysis. Blood samples for hematology testing were collected at every study visit; blood samples for serum chemistry testing and urine samples for urinalysis were collected to measure overall patient health at screening, day 1/baseline (pre-dose), day 15, day 29, day 43, day 57, day 71, day 85, day 99, day 113, day 141, day 169, and day 197 (end-of study) or early termination if subject is discontinued from the study.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 8, 15, 22, 29, 36, 43, 50, 57, 64, 71, 78, 85, 99, 113, 141, 169 and 197 (end of study) or early termination. Vital signs were taken at 1 and 2 hours post-injection following the study drug dose on days 1, 8, 15, 22, 29, 36, 43, 50, 57, 64, 71 and 78.

12-Lead ECG parameters include: Ventricular HR, PR interval, QRS interval, corrected QT interval (QTcF=QT/[$RR^{0.33}$] and QTcB=QT[$RR^{0.5}$]) ECG status: normal, abnormal not clinical significant or abnormal clinical significant. A standard 12-lead ECG was performed at screening, day 141, and day 197 (end of study) or early termination.

Research samples (serum/RNA/plasma) were collected at screening and day 1/baseline (pre-dose), and days 8, 15, 22, 29, 57, 85, and 197 (end of study) or early termination, and at unscheduled visits.

A thorough and complete physical examination was performed at screening, day 85, and day 197 (end of study) or early termination.

E. Data Analysis

1. Analyses of Exploratory Efficacy Variables

All categorical variables were analyzed using the Fisher's Exact test with nominal p-value and confidence intervals reported. All continuous variables were analyzed by the ANalysis of COVAriance (ANCOVA) using baseline IgE stratum (<150 kU/L vs. 150 kU/L at the screening visit). Unless otherwise specified, assessments of changes from baseline and construction of confidence intervals for continuous measures were based on an ANCOVA model that includes treatment as the main factor and baseline value as covariates. Point estimate and 95% CI of the difference in adjusted mean change from baseline between two treatment groups are provided. Missing values will be imputed by the last observation carried forward (LOCF) approach. In the event that the model assumptions are not warranted, the Rank-based analysis of covariates will be used.

2. Analysis of Safety Data

The safety analysis is based on the reported AEs, clinical laboratory evaluations, vital signs, and 12-lead ECG. Thresholds for Potentially Clinically Significant Values (PCSV) in laboratory variables, vital signs and ECG are defined in SAP. The time interval to detect any event or abnormality is between the infusion of study medication and end of study. Data collected outside this interval are excluded from the calculation of descriptive statistics and identification of abnormalities for laboratory evaluations, vital signs and ECG.

F. Safety: Results mAb1 was generally well-tolerated with a favorable safety profile. No clinically significant laboratory test results (blood chemistry, hematology, or urinalysis) were reported during the study. No trends were seen in mean/median baseline in any laboratory parameter. There were no significant trends in mean or median changes from baseline in temperature or pulse throughout the study. No clinically significant abnormalities were seen on physical examination results, ECGs or vital signs.

The overall adverse event (AE) profile was characteristic of a healthy population. No deaths were reported. There were 8 patients with SAEs, of which 1 was in mAb1 group (facial bones fracture) and 7 were in the placebo group (angina pectoris, cellulitis, eczema herpeticum, skin bacterial infection, renal failure, asthmatic crisis, lung disorder and atopic dermatitis). There were 8 patients with TEAE resulting in discontinuation from study drug, of which 1 was in the mAb1 group and 7 in the placebo group. There were 87 patients with at least one TEAE (n=43 [78.2%] in mAb1 vs. 44 [81.5%] in placebo group). The most frequent TEAEs were nasopharyngitis infections in subjects dosed with mAb1 (n=22 [40%] vs. 10 [18.5%] for placebo). Other TEAEs in the treatment group included eye infections, nervous system disorders, and general disorders and administration site conditions. The TEAEs over 28 weeks are summarized in Table 12.

TABLE 12

Treatment Emergent Adverse Events over 28 weeks

|  | Placebo (n = 54) | mAb1 300 mg (n = 55) |
|---|---|---|
| Total number of adverse events (AEs) | 159 | 163 |
| Total number of AEs related to study drug | 45 | 49 |
| Total number of serious AEs | 11 | 1 |
| Deaths | 0 | 0 |
| Number (%) of patients discontinued from study: | | |
| Due to AE | 3 (5.6) | 1 (1.8) |
| Due to lack of efficacy | 23 (42.6) | 7 (12.7) |
| Infections and Infestations | 31 (57.4) | 31 (56.4) |
| Most common AEs (≥10%) | | |
| Nasopharyngitis | 10 (18.5) | 22 (40.0) |
| Headache | 7 (13.0) | 9 (16.4) |
| Conjunctivitis | 2 (3.7) | 7 (12.7) |

There were notably fewer skin infections associated with mAb1 treatment (5.5%) compared with placebo (24.1%). The number and type of skin infections observed in patients on mAb1 versus placebo are shown in Table 13.

TABLE 13

Skin infections in patients on mAb1 vs. placebo

|  | Placebo (n = 54) | mAb1 300 mg (n = 55) |
|---|---|---|
| Total number of skin infections, no. of patients (%) | 13 (24.1%) | 3 (5.5%) |
| Impetigo | 3 | 1 |
| Skin bacterial infection | 3 | 0 |
| Eczema herpeticum | 2 | 0 |
| Skin infection | 2 | 0 |
| Anorectal dermatitis | 1 | 0 |
| Cellulitis | 1 | 0 |
| Infected dermatitis | 1 | 0 |
| Folliculitis | 1 | 0 |
| Infected blister | 0 | 1 |
| Pustular rash | 0 | 1 |

Subcutaneous administration of mAb1 to adult patients with moderate-to-severe AD was generally safe and well-tolerated.

G. Efficacy: Results

The baseline and exploratory efficacy results obtained from the study are summarized in FIGS. 9-28 and Tables 14-24. As noted above, patients were treated with 300 mg subcutaneous mAb1 once a week for 12 weeks, or with placebo.

TABLE 14

Summary of Baseline Characteristics - all values represented as Mean (SD)

|  | Placebo | mAb1 300 mg | All Subjects Combined |
|---|---|---|---|
| No. Patients | 54 | 55 | 109 |
| Age (years) Mean (SD) | 39.4 (12.29) | 33.7 (10.41) | 36.5 (11.69) |

TABLE 14-continued

Summary of Baseline Characteristics - all values represented as Mean (SD)

|  | Placebo | mAb1 300 mg | All Subjects Combined |
|---|---|---|---|
| Ethnicity n (%) | | | |
| Hispanic or Latino | 1 (1.9%) | 3 (5.5%) | 4 (3.7%) |
| Not Hispanic or Latino | 53 (98.1%) | 52 (94.5%) | 105 (96.3%) |
| Gender n (%) | | | |
| Male | 27 (50.0%) | 31 (56.4%) | 58 (53.2%) |
| Female | 27 (50.0%) | 24 (43.6%) | 51 (46.8%) |
| Height (cm) Mean (SD) | 171.2 (9.89) | 173.4 (9.88) | 172.3 (9.90) |
| Weight (kg) Mean (SD) | 72.41 (17.539) | 78.13 (17.416) | 75.30 (17.632) |
| BMI (kg/m$^2$) Mean (SD) | 24.51 (4.639) | 25.89 (4.837) | 25.20 (4.768) |
| Chronic Atopic Dermatitis Diagnosis Age | 14.4 (18.35) | 6.6 (10.53) | 10.5 (15.37) |
| BSA | 50.8 (24.14) | 46.8 (24.55) | 48.8 (24.32) |
| EASI Score | 30.8 (13.63) | 28.4 (13.57) | 29.6 (13.59) |
| IGA Score | 4.0 (0.69) | 3.9 (0.67) | 3.9 (0.68) |
| NRS Score | 5.8 (1.93) | 6.1 (1.34) | 5.9 (1.66) |
| SCORAD Score | 69.1 (13.38) | 66.7 (13.82) | 67.9 (13.59) |
| Pruritus 5-D Scale | 18.7 (3.50) | 18.4 (3.04) | 18.5 (3.26) |

TABLE 15

Summary of Baseline characteristics of the QoLIAD subset

|  | Placebo | mAb1 300 mg |
|---|---|---|
| No. Patients | 32 | 32 |
| Age (years) Mean (SD) | 40.7 (11.6) | 37.3 (10.5) |
| Male, n (%) | 17 (53.1) | 19 (59.4) |
| White, n (%) | 32 (100) | 32 (100) |
| BMI (kg/m$^2$) Mean (SD) | 23.6 (4.1) | 25.6 (5.0) |
| Duration of AD, years, mean (SD) | 27.3 (12.3) | 29.8 (13.2) |
| EASI Score, mean (SD) | 27.3 (13.7) | 26.4 (13.7) |
| 5-D Pruritus score, mean (SD) | 18.5 (3.5) | 18.0 (3.0) |
| Pruritus NRS Score, mean (SD) | 5.5 (1.8) | 5.7 (1.4) |
| QoLIAD, mean (SD) | 13.3 (7.6) | 11.3 (6.2) |

TABLE 16

Summary of Percentage and Absolute Change in EASI Score from Baseline to Week 12 and Each Visit during Follow-up period - all values represented as Mean (SD)

|  | Placebo | 300 mg mAb1 |
|---|---|---|
| No. Patients | 54 | 55 |
| Baseline EASI Score | 30.8 (13.63) | 28.4 (13.57) |
| Day 85 EASI Score | 24.4 (19.01) | 8.5 (12.15) |
| % Change from Baseline to Day 85 | −23.3 (49.26) | −74.0 (26.94) |
| Absolute change from Baseline to Day 85 | −6.4 (14.85) | −19.9 (11.52) |
| Day 99 EASI Score | 24.2 (19.15) | 8.4 (11.86) |
| % Change from Baseline to Day 99 | −23.2 (49.42) | −73.5 (27.21) |
| Absolute change from Baseline to Day 99 | −6.6 (15.20) | −20.0 (12.24) |
| Day 113 EASI Score | 24.1 (18.80) | 9.1 (12.13) |
| % Change from Baseline to Day 113 | −23.4 (47.75) | −71.4 (27.03) |
| Absolute change from Baseline to Day 113 | −6.7 (14.96) | −19.4 (11.42) |
| Day 127 EASI Score | 24.5 (18.91) | 9.2 (12.41) |
| % Change from Baseline to Day 127 | −22.1 (47.11) | −71.2 (27.39) |
| Absolute change from Baseline to Day 127 | −6.3 (14.98) | −19.2 (11.15) |
| Day 141 EASI Score | 23.8 (18.47) | 9.4 (12.18) |
| % Change from Baseline to Day 141 | −23.9 (47.01) | −70.8 (26.91) |
| Absolute change from Baseline to Day 141 | −7.0 (14.77) | −19.0 (10.86) |
| Day 155 EASI Score | 24.0 (18.27) | 9.9 (12.40) |
| % Change from Baseline to Day 155 | −23.0 (46.22) | −68.8 (27.35) |
| Absolute change from Baseline to Day 155 | −6.7 (14.49) | −18.5 (10.74) |
| Day 169 EASI Score | 23.5 (18.22) | 11.0 (12.76) |
| % Change from Baseline to Day 169 | −24.2 (46.66) | −64.4 (29.19) |
| Absolute change from Baseline to Day 169 | −7.3 (14.93) | −17.5 (10.82) |
| Day 183 EASI Score | 23.5 (18.57) | 10.8 (13.00) |
| % Change from Baseline to Day 183 | −24.6 (47.35) | −65.0 (29.21) |
| Absolute change from Baseline to Day 183 | −7.3 (15.12) | −17.6 (10.93) |
| Day 197 EASI Score | 23.4 (18.59) | 11.0 (13.13) |
| % Change from Baseline to Day 197 | −25.0 (48.57) | −64.0 (30.80) |
| Absolute change from Baseline to Day 197 | −7.4 (15.23) | −17.4 (11.88) |

TABLE 17

Summary of Percentage and Absolute Change in IGA Score from Baseline to Week 12 and Each Visit during Follow-up period - all values represented as Mean (SD)

|  | Placebo | 300 mg mAb1 |
|---|---|---|
| No. Patients | 54 | 55 |
| Baseline IGA Score | 4.0 (0.69) | 3.9 (0.67) |
| Day 85 IGA Score | 3.4 (1.19) | 2.0 (1.15) |
| % Change from Baseline to Day 85 | −14.7 (27.37) | −49.5 (25.94) |
| Absolute change from Baseline to Day 85 | −0.6 (1.07) | −1.9 (0.98) |
| Day 99 IGA Score | 3.4 (1.16) | 2.1 (1.17) |
| % Change from Baseline to Day 99 | −14.0 (27.03) | −45.8 (26.98) |
| Absolute change from Baseline to Day 99 | −0.6 (1.06) | −1.7 (1.06) |
| Day 113 IGA Score | 3.3 (1.20) | 2.2 (1.08) |
| % Change from Baseline to Day 113 | −15.9 (27.82) | −43.1 (25.53) |
| Absolute change from Baseline to Day 113 | −0.6 (1.12) | −1.7 (1.06) |
| Day 127 IGA Score | 3.4 (1.16) | 2.2 (1.16) |
| % Change from Baseline to Day 127 | −14.5 (26.66) | −44.1 (27.06) |
| Absolute change from Baseline to Day 127 | −0.6 (1.07) | −1.7 (1.07) |
| Day 141 IGA Score | 3.4 (1.15) | 2.2 (1.12) |
| % Change from Baseline to Day 141 | −15.0 (26.52) | −42.8 (26.01) |
| Absolute change from Baseline to Day 141 | −0.6 (1.05) | −1.6 (1.01) |
| Day 155 IGA Score | 3.4 (1.14) | 2.3 (1.08) |
| % Change from Baseline to Day 155 | −14.2 (25.89) | −41.5 (25.20) |
| Absolute change from Baseline to Day 155 | −0.6 (1.02) | −1.6 (1.01) |
| Day 169 IGA Score | 3.3 (1.17) | 2.5 (1.07) |
| % Change from Baseline to Day 169 | −15.9 (26.96) | −36.0 (25.87) |
| Absolute change from Baseline to Day 169 | −0.6 (1.08) | −1.4 (1.03) |
| Day 183 IGA Score | 3.3 (1.18) | 2.4 (1.10) |
| % Change from Baseline to Day 183 | −16.3 (27.33) | −37.2 (26.93) |
| Absolute change from Baseline to Day 183 | −0.7 (1.10) | −1.5 (1.09) |
| Day 197 IGA Score | 3.3 (1.29) | 2.3 (1.09) |
| % Change from Baseline to Day 197 | −16.5 (30.18) | −39.0 (27.42) |
| Absolute change from Baseline to Day 197 | −0.7 (1.20) | −1.5 (1.10) |

TABLE 18

Summary of Absolute Change in BSA Score from Baseline to Week 12 and Each Visit during Follow-up period - all values represented as Mean (SD)

| | Placebo | 300 mg mAb1 |
|---|---|---|
| No. Patients | 54 | 55 |
| Baseline BSA Score | 50.8 (24.13) | 46.8 (24.55) |
| Day 85 BSA Score | 41.8 (30.44) | 19.4 (23.43) |
| Absolute change from Baseline to Day 85 | −9.0 (21.07) | −27.4 (22.81) |
| Day 99 BSA Score | 41.7 (30.85) | 19.9 (22.85) |
| Absolute change from Baseline to Day 99 | −9.2 (21.85) | −26.9 (22.74) |
| Day 113 BSA Score | 41.3 (30.52) | 20.8 (23.16) |
| Absolute change from Baseline to Day 113 | −9.5 (21.34) | −26.0 (21.90) |
| Day 127 BSA Score | 42.1 (30.41) | 21.4 (23.48) |
| Absolute change from Baseline to Day 127 | −8.7 (20.72) | −25.4 (21.29) |
| Day 141 BSA Score | 41.5 (29.85) | 21.3 (22.88) |
| Absolute change from Baseline to Day 141 | −9.4 (20.57) | −25.5 (21.50) |
| Day 155 BSA Score | 41.5 (29.61) | 22.1 (23.05) |
| Absolute change from Baseline to Day 155 | −9.3 (20.26) | −24.6 (21.55) |
| Day 169 BSA Score | 41.2 (29.28) | 24.6 (24.15) |
| Absolute change from Baseline to Day 169 | −9.6 (20.35) | −22.2 (21.50) |
| Day 183 BSA Score | 41.0 (30.28) | 24.1 (24.15) |
| Absolute change from Baseline to Day 183 | −9.9 (21.35) | −22.7 (22.86) |
| Day 197 BSA Score | 40.5 (29.95) | 24.9 (25.70) |
| Absolute change from Baseline to Day 197 | −10.4 (21.40) | −21.9 (24.11) |

TABLE 19

Summary of Absolute Change in SCORAD Score from Baseline to Week 12 and Each Visit during Follow-up period - all values represented as Mean (SD)

| | Placebo | 300 mg mAb1 |
|---|---|---|
| No. Patients | 54 | 55 |
| Baseline SCORAD Score | 69.1 (13.38) | 66.7 (13.82) |
| Day 85 SCORAD Score | 59.3 (23.44) | 31.7 (22.08) |
| Absolute change from Baseline to Day 85 | −9.8 (20.53) | −35.0 (19.43) |
| Day 99 SCORAD Score | 58.8 (23.35) | 32.5 (20.99) |
| Absolute change from Baseline to Day 99 | −10.3 (21.33) | −34.3 (18.94) |
| Day 113 SCORAD Score | 59.1 (22.30) | 34.0 (2051) |
| Absolute change from Baseline to Day 113 | −10.0 (20.89) | −32.7 (18.48) |
| Day 127 SCORAD Score | 59.9 (22.36) | 34.0 (21.25) |
| Absolute change from Baseline to Day 127 | 09.2 (20.59) | −32.7 (18.23) |
| Day 141 SCORAD Score | 59.0 (21.85) | 33.9 (20.51) |
| Absolute change from Baseline to Day 141 | −10.1 (20.12) | −32.8 (17.97) |
| Day 155 SCORAD Score | 59.0 (22.50) | 35.1 (20.16) |
| Absolute change from Baseline to Day 155 | −10.0 (20.17) | −31.6 (17.99) |
| Day 169 SCORAD Score | 58.5 (22.33) | 37.1 (20.82) |
| Absolute change from Baseline to Day 169 | −10.6 (20.90) | −29.6 (19.15) |
| Day 183 SCORAD Score | 58.7 (22.47) | 37.5 (20.89) |
| Absolute change from Baseline to Day 183 | −10.4 (20.86) | −29.2 (19.50) |
| Day 197 SCORAD Score | 57.8 (23.82) | 38.8 (22.04) |
| Absolute change from Baseline to Day 197 | −11.3 (22.05) | −27.9 (21.70) |

TABLE 20

Summary of Absolute Change in 5-D Pruritus Scale from Baseline to Week 12 and Each Week during Follow-up period - all values represented as Mean (SD)

| | Placebo | 300 mg mAb1 |
|---|---|---|
| No. Patients | 54 | 55 |
| Baseline 5-D Pruritus Score | 18.7 (3.50) | 18.4 (3.04) |
| Day 85 5-D Pruritus Score | 16.9 (5.33) | 11.0 (4.22) |
| Absolute change from Baseline to Day 85 | −1.9 (4.28) | −7.4 (4.33) |
| Day 99 5-D Pruritus Score | 16.7 (5.28) | 11.3 (3.96) |
| Absolute change from Baseline to Day 99 | −2.0 (4.63) | −7.0 (4.41) |
| Day 113 5-D Pruritus Score | 16.5 (5.57) | 11.7 (4.05) |
| Absolute change from Baseline to Day 113 | −2.2 (4.91) | −6.7 (4.21) |
| Day 127 5-D Pruritus Score | 16.7 (5.44) | 11.5 (4.07) |
| Absolute change from Baseline to Day 127 | −2.0 (4.72) | −6.9 (4.24) |
| Day 141 5-D Pruritus Score | 16.4 (5.67) | 11.8 (4.19) |
| Absolute change from Baseline to Day 141 | −2.3 (5.12) | −6.6 (4.56) |
| Day 155 5-D Pruritus Score | 16.6 (5.53) | 12.0 (4.21) |
| Absolute change from Baseline to Day 155 | −2.1 (4.90) | −6.4 (4.49) |
| Day 169 5-D Pruritus Score | 16.8 (5.35) | 12.7 (4.20) |
| Absolute change from Baseline to Day 169 | −1.9 (4.78) | −5.7 (4.58) |
| Day 183 5-D Pruritus Score | 16.6 (5.59) | 12.8 (4.56) |
| Absolute change from Baseline to Day 183 | −2.1 (5.02) | −5.6 (4.90) |
| Day 197 5-D Pruritus Score | 16.6 (5.50) | 13.1 (4.85) |
| Absolute change from Baseline to Day 197 | −2.1 (5.12) | −5.3 (5.06) |

TABLE 21

Summary of Absolute Change in Average NRS Score from Baseline to Week 12 and Each Week during Follow-up period - all values represented as Mean (SD)

| | Placebo | 300 mg mAb1 |
|---|---|---|
| No. Patients | 54 | 55 |
| Baseline NRS Score | 5.8 (1.93) | 6.1 (1.34) |
| Day 85 NRS Score | 4.9 (2.53) | 2.6 (1.67) |
| Absolute change from Baseline to Day 85 | −0.9 (2.07) | −3.5 (2.00) |
| Day 92 NRS Score | 4.8 (2.57) | 2.8 (1.68) |
| Absolute change from Baseline to Day 92 | −1.0 (2.07) | −3.4 (2.12) |
| Day 99 NRS Score | 4.7 (2.54) | 2.7 (1.72) |
| Absolute change from Baseline to Day 99 | −1.0 (2.06) | −3.4 (2.17) |
| Day 106 NRS Score | 4.8 (2.59) | 2.7 (1.63) |
| Absolute change from Baseline to Day 106 | −1.0 (2.15) | −3.4 (2.08) |
| Day 113 NRS Score | 4.9 (2.69) | 2.7 (1.63) |
| Absolute change from Baseline to Day 113 | −0.9 (2.21) | −3.4 (2.00) |
| Day 120 NRS Score | 4.8 (2.61) | 2.7 (1.68) |
| Absolute change from Baseline to Day 120 | −1.0 (2.18) | −3.4 (2.07) |
| Day 127 NRS Score | 4.8 (2.68) | 2.8 (1.79) |
| Absolute change from Baseline to Day 127 | −1.0 (2.24) | −3.3 (2.20) |
| Day 134 NRS Score | 4.7 (2.75) | 2.8 (1.78) |
| Absolute change from Baseline to Day 134 | −1.1 (2.24) | −3.3 (2.18) |
| Day 141 NRS Score | 4.7 (2.73) | 2.9 (1.89) |
| Absolute change from Baseline to Day 141 | −1.1 (2.26) | −3.2 (2.28) |
| Day 148 NRS Score | 4.7 (2.75) | 2.9 (1.89) |
| Absolute change from Baseline to Day 148 | −1.1 (2.28) | −3.2 (2.28) |
| Day 155 NRS Score | 4.7 (2.75) | 2.9 (1.86) |
| Absolute change from Baseline to Day 155 | −1.1 (2.30) | −3.2 (2.19) |
| Day 162 NRS Score | 4.7 (2.75) | 3.0 (1.93) |
| Absolute change from Baseline to Day 162 | −1.1 (2.29) | −3.1 (2.28) |
| Day 169 NRS Score | 4.7 (2.75) | 3.2 (1.99) |
| Absolute change from Baseline to Day 169 | −1.1 (2.28) | −3.0 (2.43) |
| Day 176 NRS Score | 4.7 (2.74) | 3.2 (2.01) |
| Absolute change from Baseline to Day 176 | −1.1 (2.27) | −3.0 (2.49) |
| Day 183 NRS Score | 4.7 (2.75) | 3.1 (1.97) |
| Absolute change from Baseline to Day 183 | −1.1 (2.28) | −3.0 (2.41) |

TABLE 21-continued

Summary of Absolute Change in Average NRS Score from Baseline to Week 12 and Each Week during Follow-up period - all values represented as Mean (SD)

|  | Placebo | 300 mg mAb1 |
|---|---|---|
| Day 190 NRS Score | 4.7 (2.78) | 3.1 (1.91) |
| Absolute change from Baseline to Day 190 | −1.1 (2.31) | −3.1 (2.25) |
| Day 197 NRS Score | 4.7 (2.75) | 3.1 (1.95) |
| Absolute change from Baseline to Day 197 | −1.1 (2.28) | −3.0 (2.28) |

TABLE 22

Summary of Subjects achieving an IGA score of 0 or 1 to Week 12 and each visit during Follow-up period

| Number and proportion of subjects achieving an IGA score of 0 or 1 | Placebo (N = 54) | 300 mg mAb1 (N = 55) |
|---|---|---|
| Week 12, Day 85 | 4 (7.4%) | 22 (40.0%) |
| Week 14, Day 99 | 4 (7.4%) | 22 (40.0%) |
| Week 16, Day 113 | 5 (9.3%) | 18 (32.7%) |
| Week 18, Day 127 | 3 (5.6%) | 20 (36.4%) |
| Week 20, Day 141 | 4 (7.4%) | 17 (30.9%) |
| Week 22, Day 155 | 3 (5.6%) | 17 (30.9%) |
| Week 24, Day 169 | 3 (5.6%) | 13 (23.6%) |
| Week 26, Day 183 | 3 (5.6%) | 15 (27.3%) |
| Week 28, Day 197 | 6 (11.1%) | 16 (29.1%) |

TABLE 23

Summary of Subjects achieving an EASI 50 Week 12 and each visit during Follow-up period

| Number and proportion of subjects achieving an EASI score percent decrease of 50% | Placebo (N = 54) | 300 mg mAb1 (N = 55) |
|---|---|---|
| Week 12, Day 85 | 19 (35.2%) | 47 (85.5%) |
| Week 14, Day 99 | 19 (35.2%) | 46 (83.6%) |
| Week 16, Day 113 | 18 (33.3%) | 46 (83.6%) |
| Week 18, Day 127 | 18 (33.3%) | 45 (81.8%) |
| Week 20, Day 141 | 18 (33.3%) | 46 (83.6%) |
| Week 22, Day 155 | 16 (29.6%) | 43 (78.2%) |
| Week 24, Day 169 | 18 (33.3%) | 40 (72.7%) |
| Week 26, Day 183 | 19 (35.2%) | 41 (74.5%) |
| Week 28, Day 197 | 23 (42.6%) | 40 (72.7%) |

TABLE 24

QoLIAD correlations at baseline

|  | All (n = 64) | Placebo (n = 32) | mAb1 (n = 32) |
|---|---|---|---|
| EASI score and QoLIAD |  |  |  |
| Pearson coefficient | 0.3119 | 0.3009 | 0.3262 |
| P-value | 0.0121 | 0.0942 | 0.0684 |
| Pruritus NRS and QoLIAD |  |  |  |
| Pearson coefficient | 0.2533 | 0.2305 | 0.3362 |
| P-value | 0.0434 | 0.2044 | 0.0599 |
| Pruritus 5-D and QoLIAD |  |  |  |
| Pearson coefficient | 0.3847 | 0.3235 | 0.4588 |
| P-value | 0.0017 | 0.0709 | 0.0083 |

H. Conclusions

Figure 15:
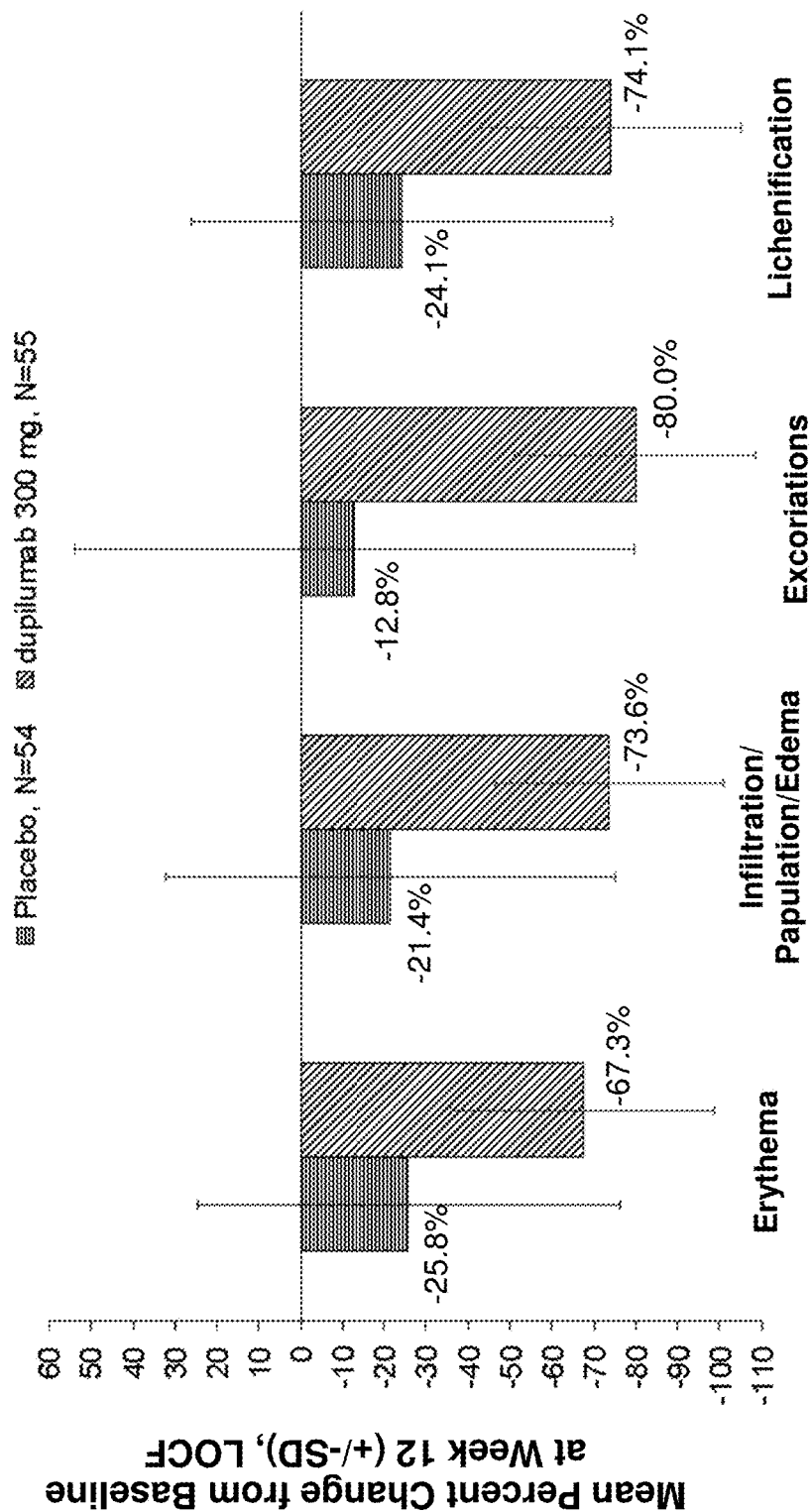
FIG. 15 shows the mean percent change in EASI subcomponents from baseline at week 12 for the study in Example 2.
Figure 16:
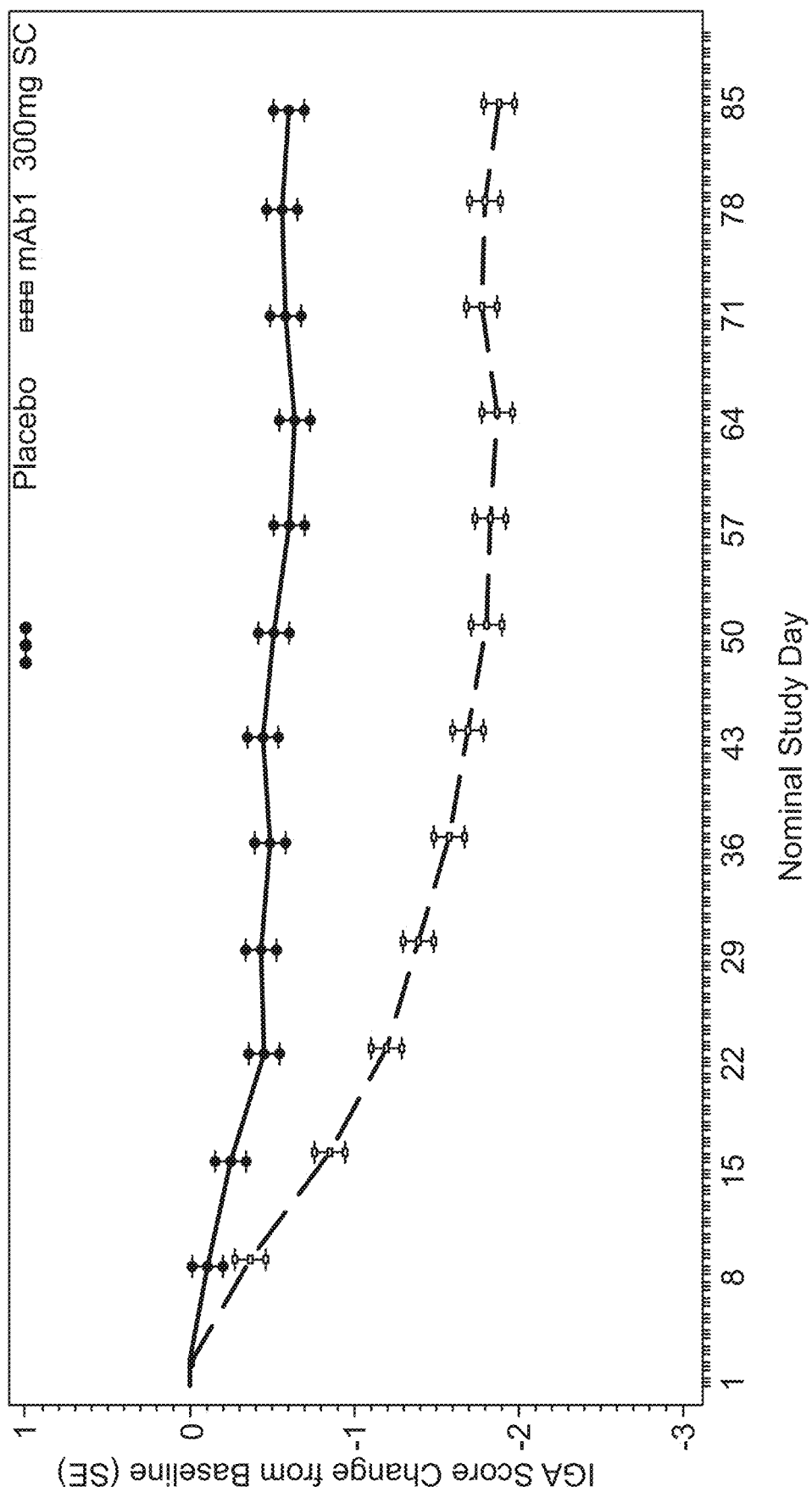
FIG. 16 shows mean IGA score change from baseline up to LOCF for the study in Example 2.
Figure 17:
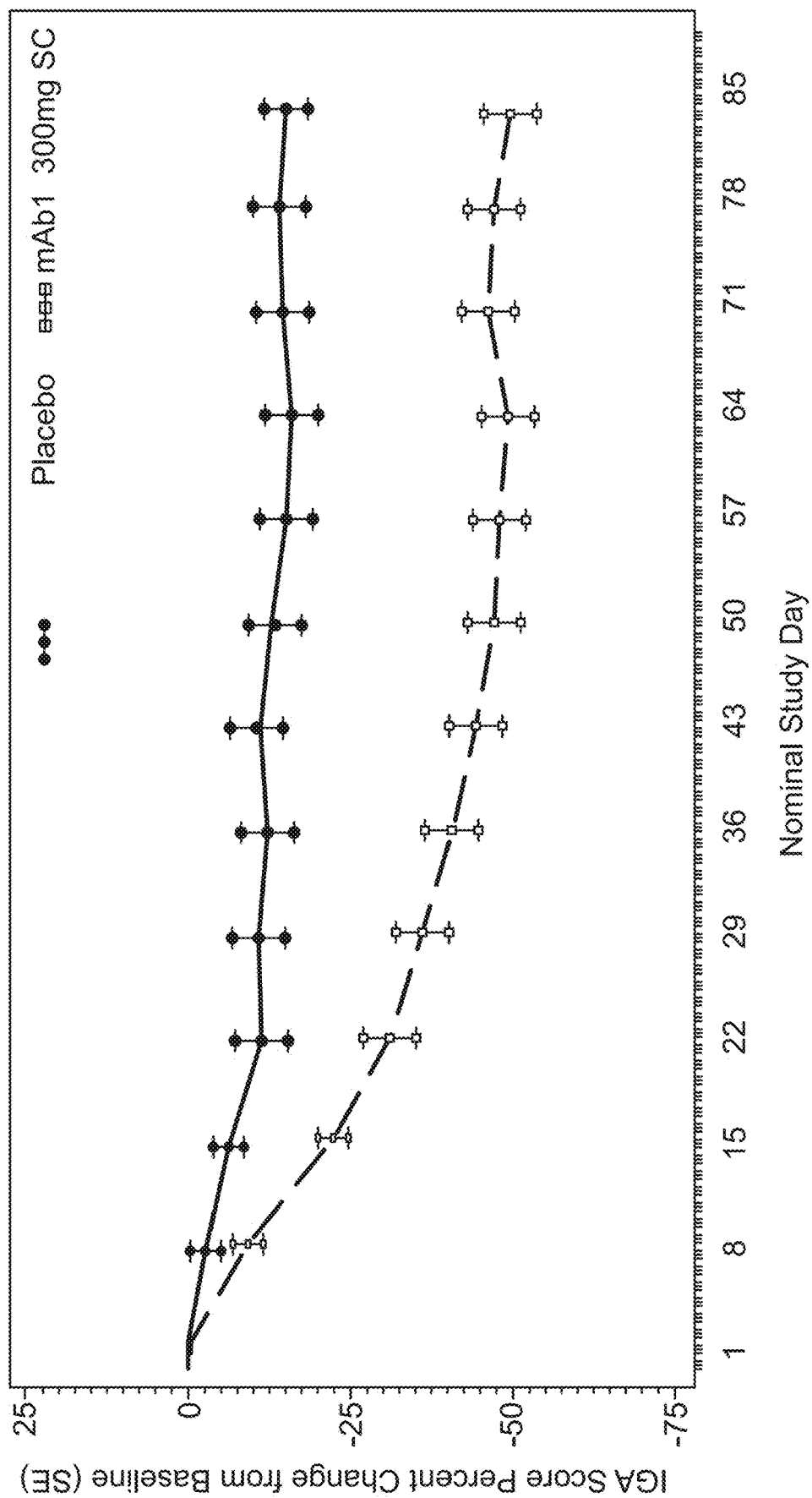
FIG. 17 shows mean IGA score percent change from baseline up to LOCF for the study in Example 2.
Figure 18:
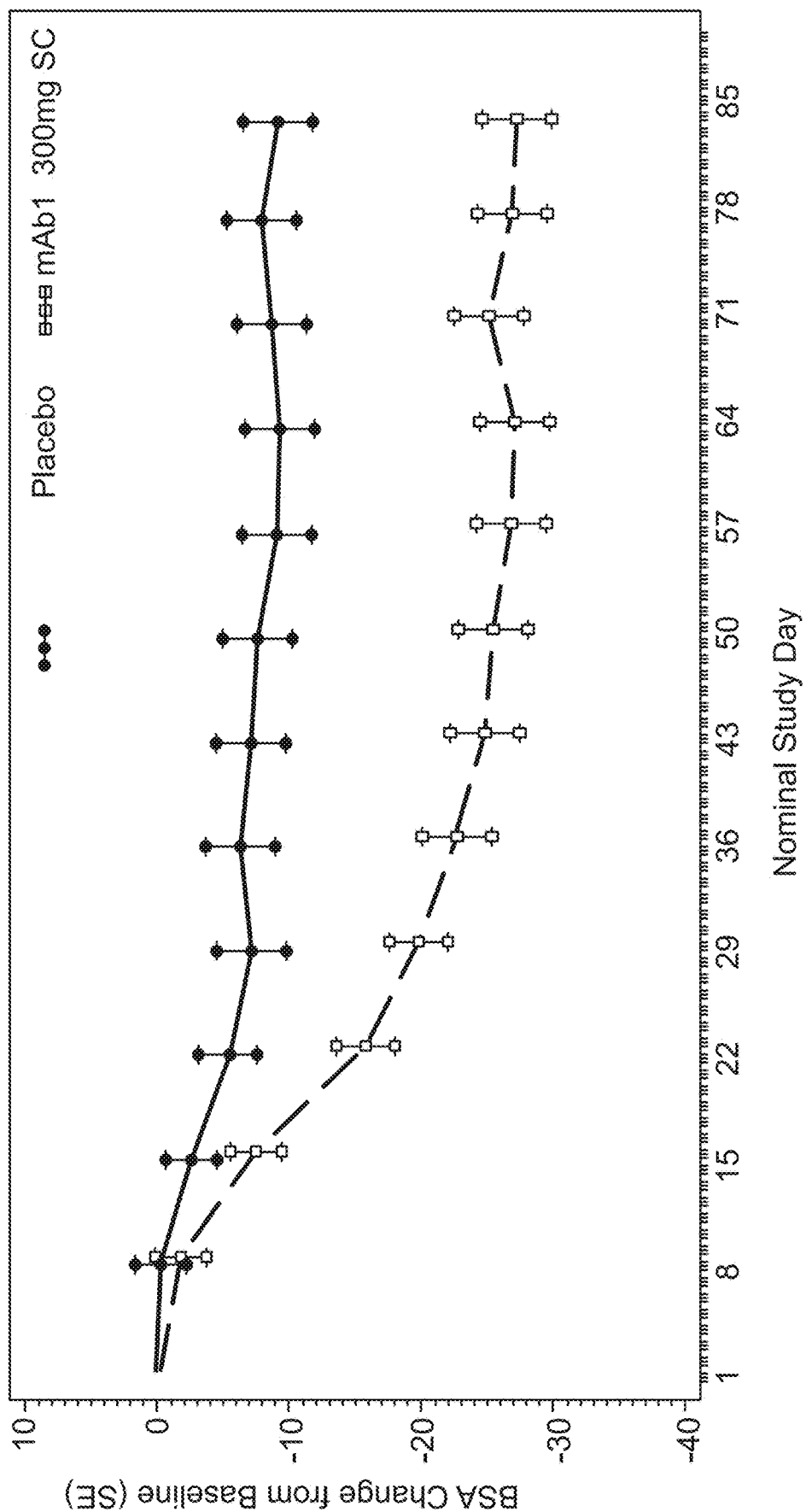
FIG. 18 shows mean BSA change from baseline up to LOCF for the study in Example 2.
Figure 19:
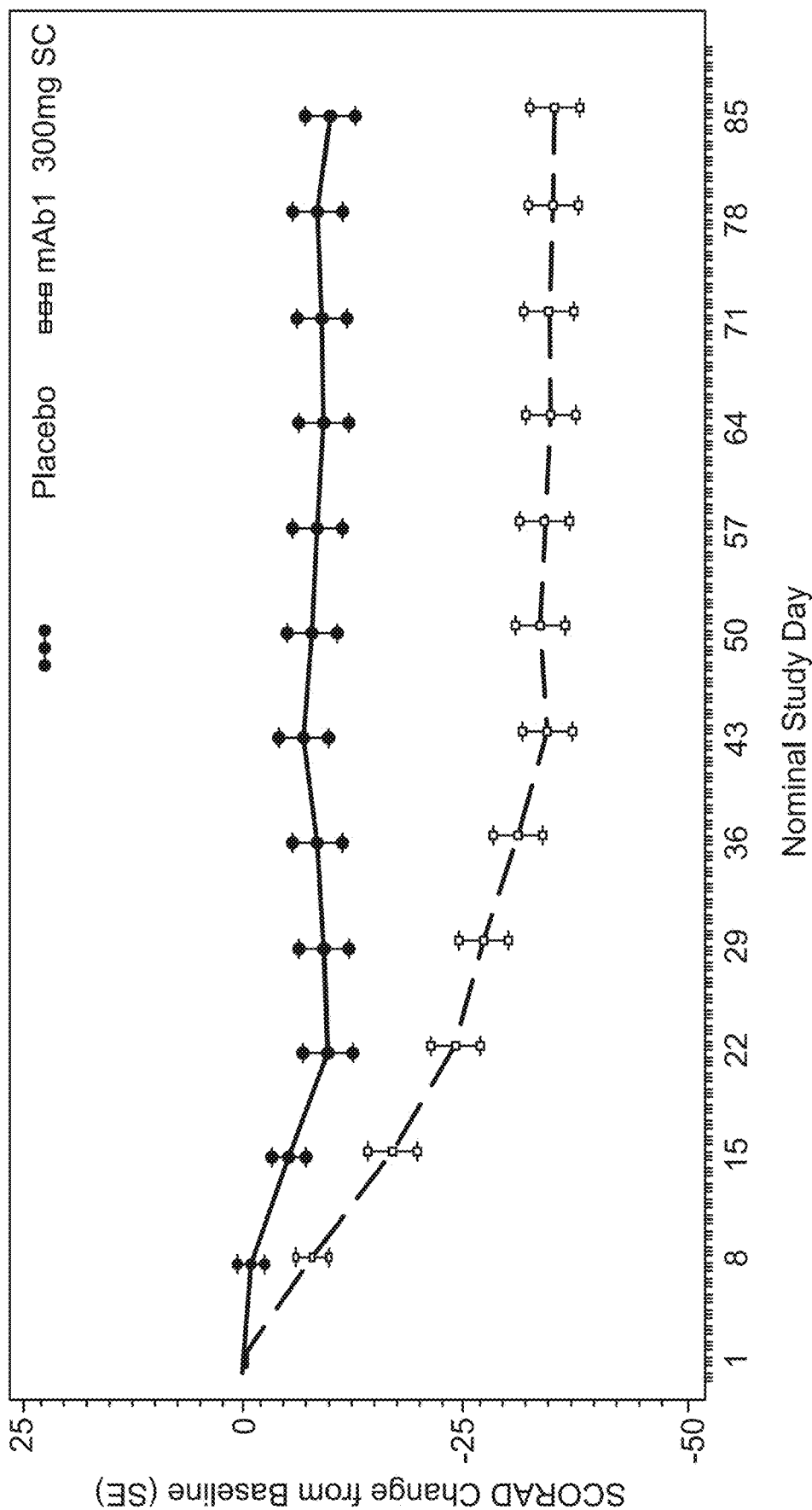
FIG. 19 shows mean SCORAD score change from baseline up to LOCF for the study in Example 2.
Figure 20:
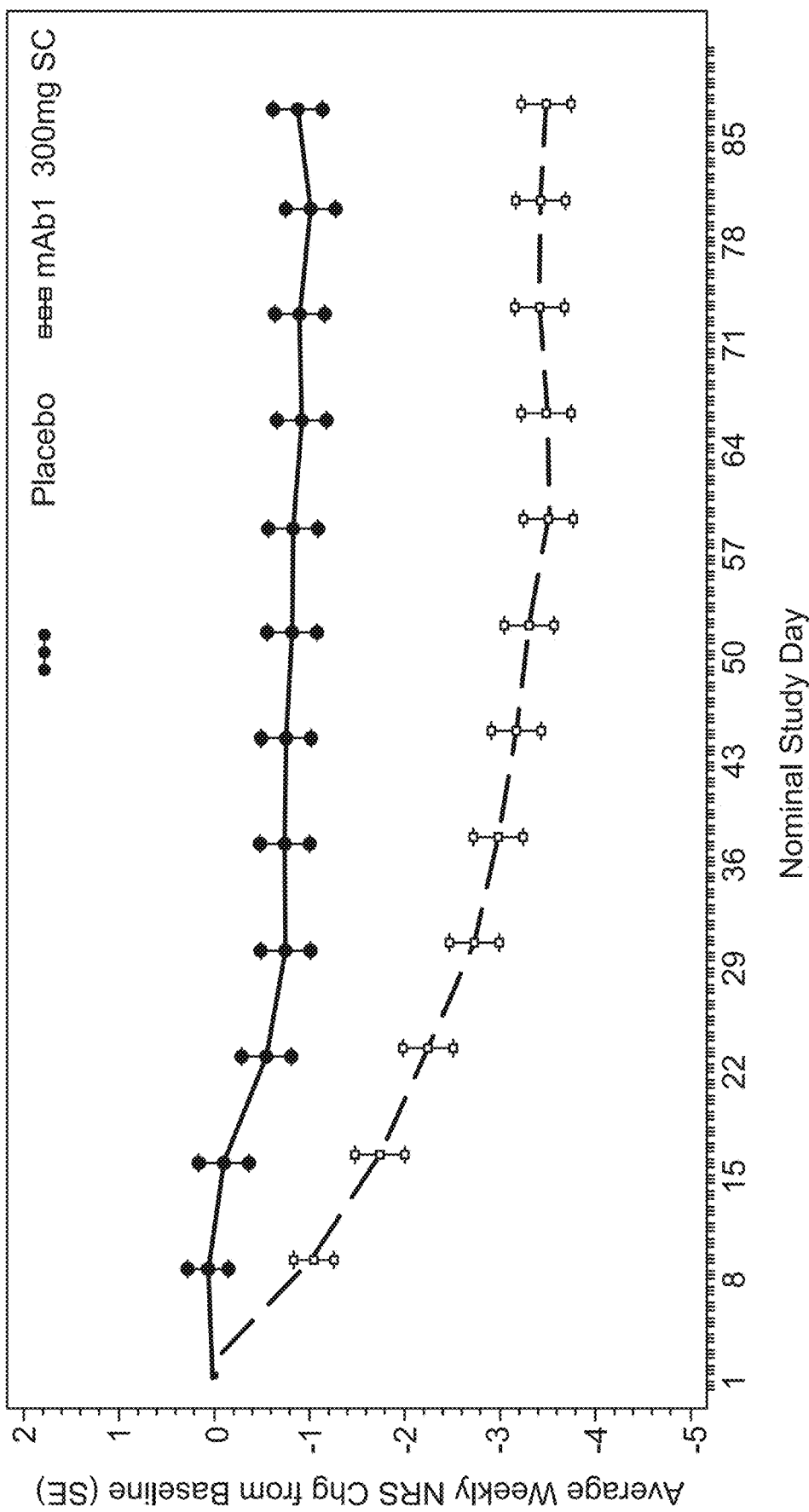
FIG. 20 shows mean NRS score change from baseline up to LOCF for the study in Example 2.
Figure 21:
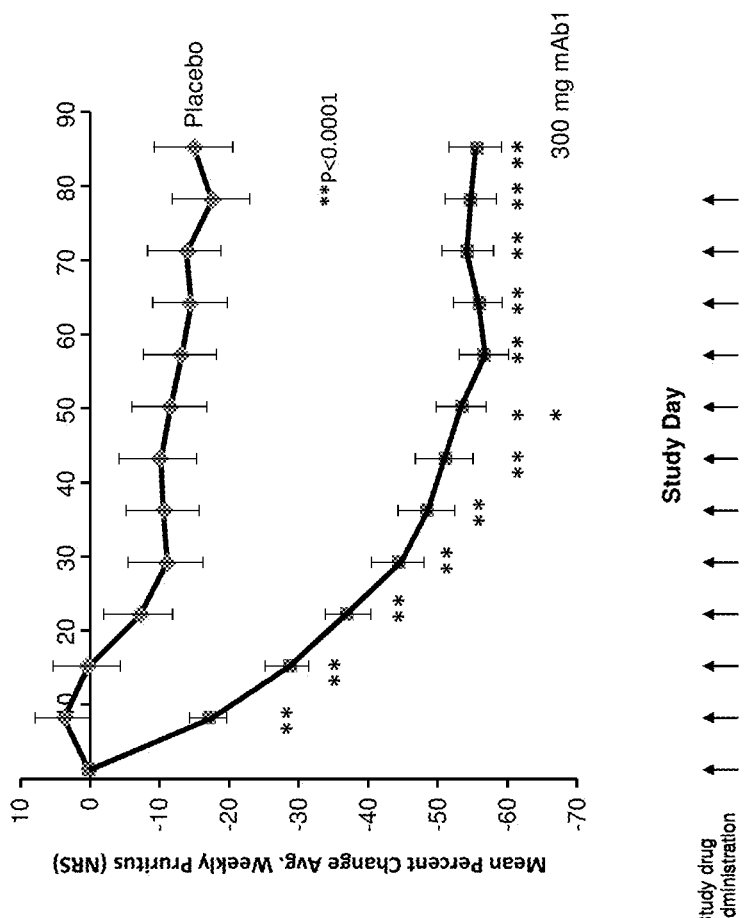
FIG. 21 shows mean percent change in NRS score from baseline for 12 weeks for the study in Example 2.
Figure 22:
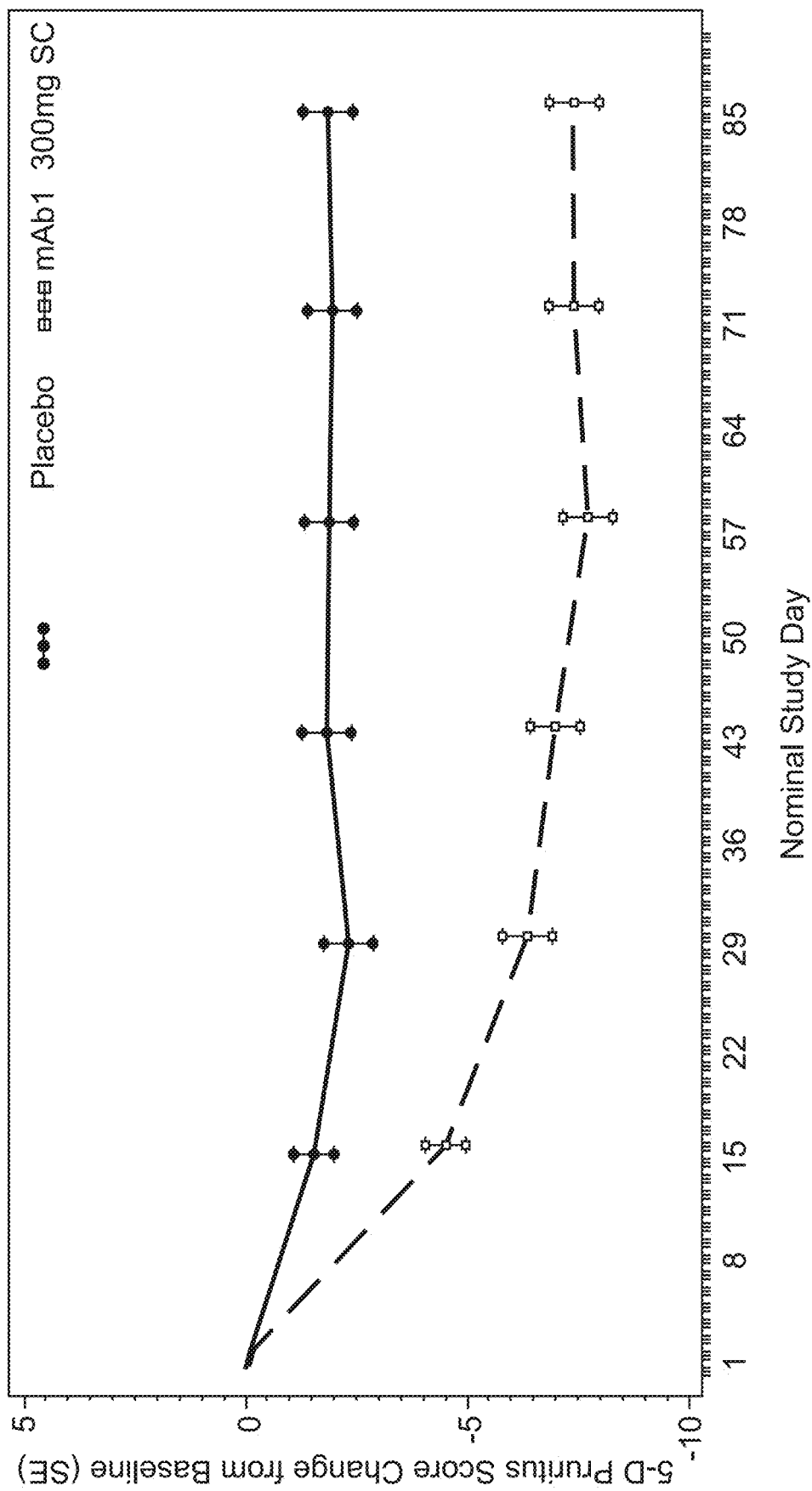
FIG. 22 shows mean 5-D Pruritus score change from baseline up to LOCF for the study in Example 10.
Figure 23:
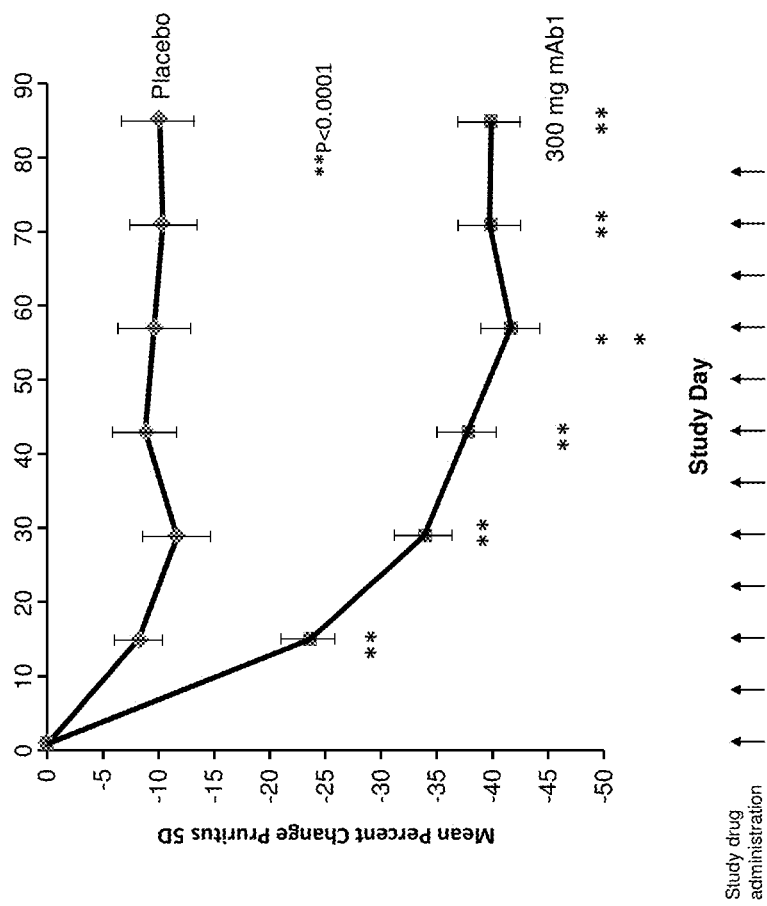
FIG. 23 shows mean percent 5-D Pruritus score change from baseline for 12 weeks for the study in Example 2.
Figure 24:
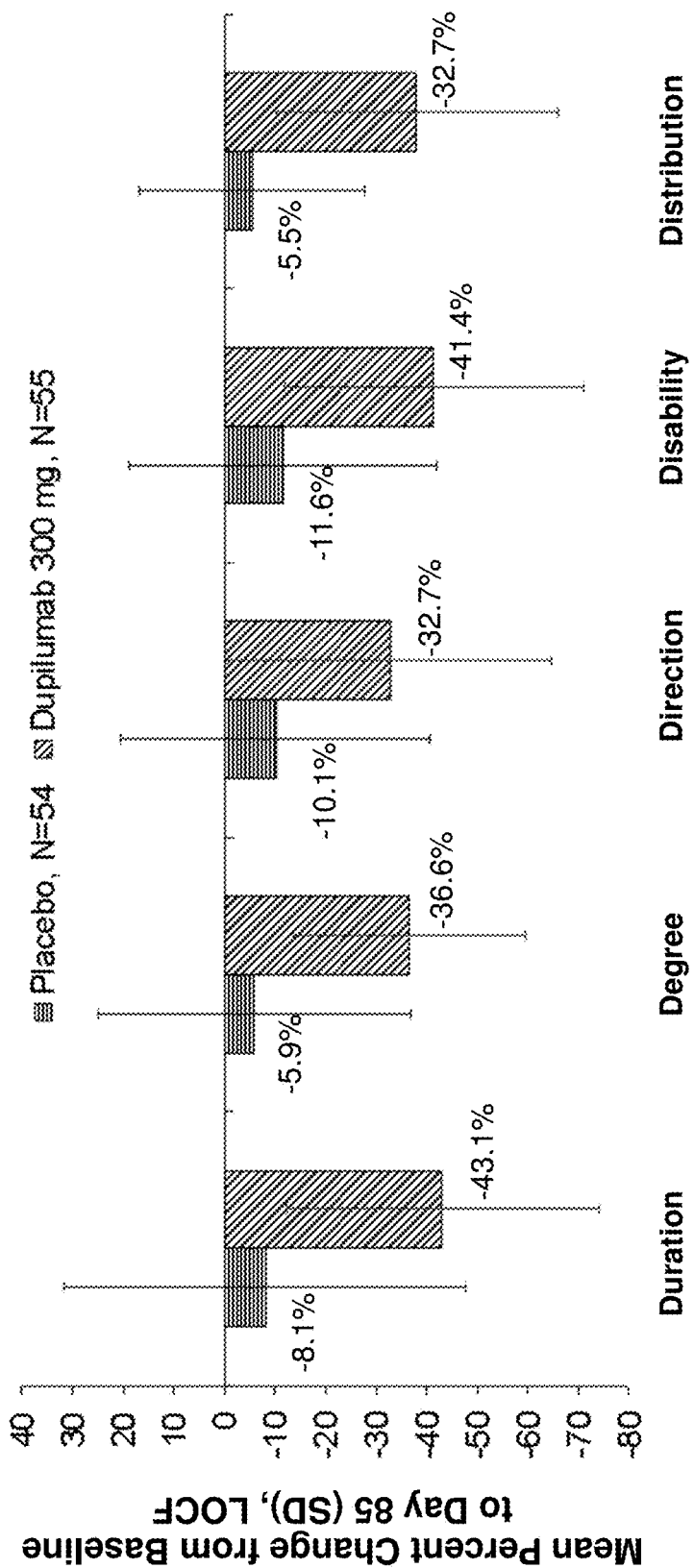
FIG. 24 shows the mean percent change in subcomponents of 5-D-Pruritus score from baseline to day 85 for the study in Example 2.
Figure 25:
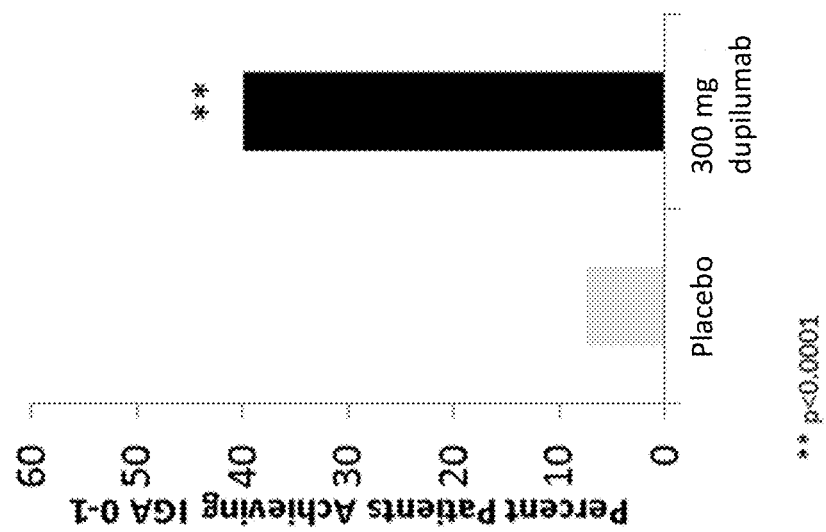
FIG. 25 shows percent patients achieving IGA 0-1 at 12 weeks for the study in Example 2.
Figure 26:
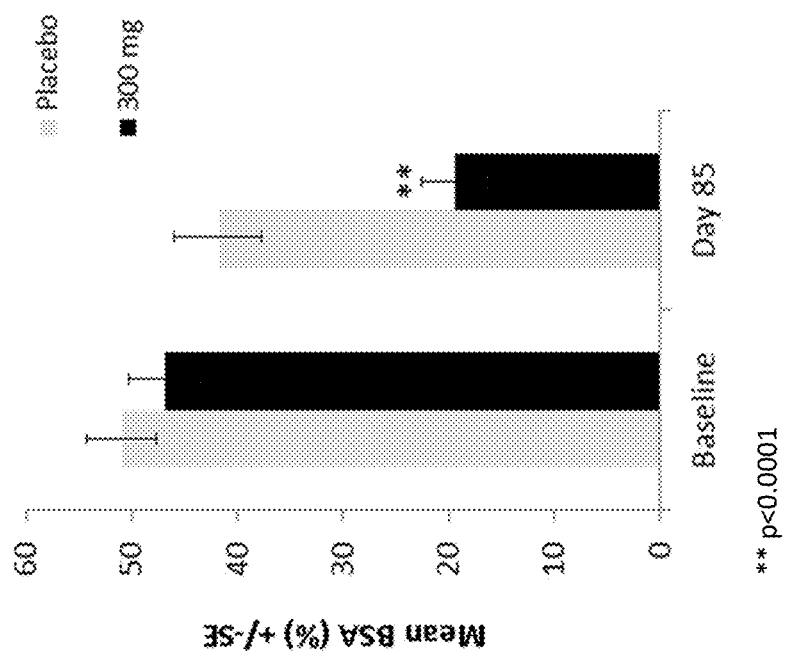
FIG. 26 shows percent patients achieving mean percent BSA at 12 weeks for the study in Example 2.
Figure 27:
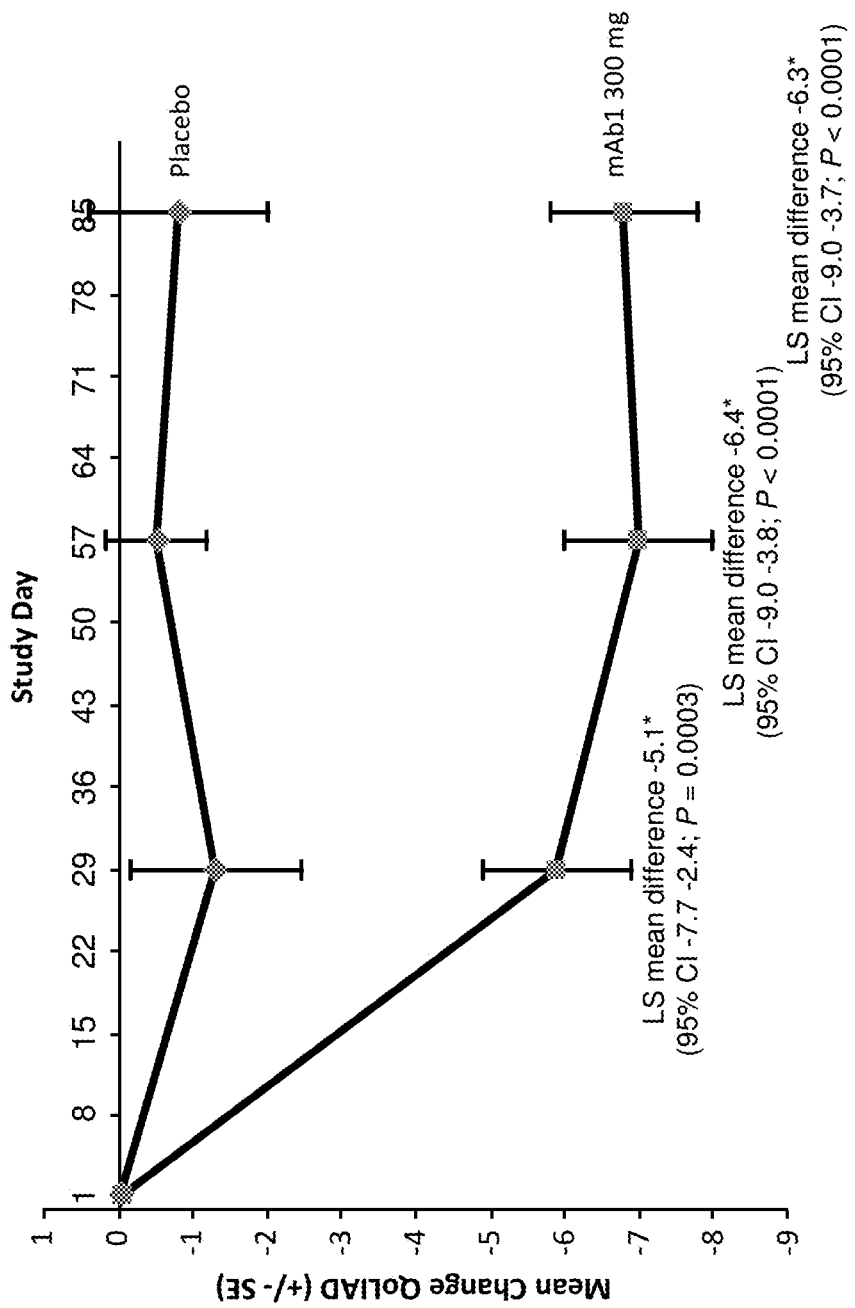
FIG. 27 shows the mean change from baseline to week 12 in QoLIAD for the study in Example 2.
Figure 28:
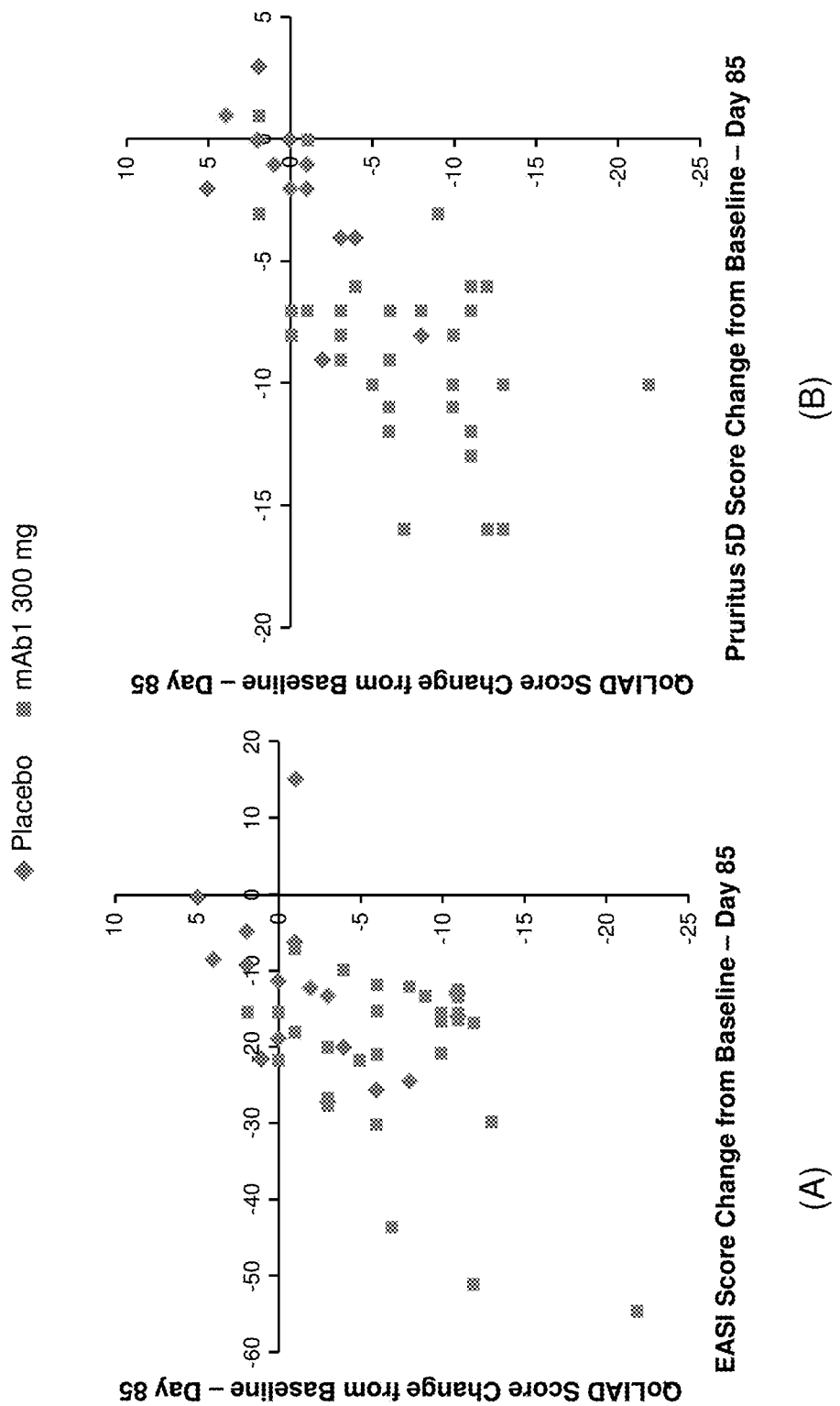
FIG. 28 shows the correlation between change in QoLIAD and change in clinical outcomes EASI (A) and 5-D Pruritus (B) at week 12 for the study in Example 2.

Subcutaneous administration of an anti-IL-4R antibody (mAb1) to adult patients with moderate-to-severe atopic dermatitis was generally safe and well tolerated after 12 weekly doses of 300 mg. Administration of mAb1 at 300 mg resulted in significant improvement in IGA, EASI, BSA, SCORAD and NRS pruritus through day 85 in both mean and absolute and percent change, as compared to baseline (see Tables 14, 16-21). The proportion of patients achieving an IGA score of 0 or 1 at Day 85 for the 300 mg group was 40.0%, while the same number for placebo was 7.4% (Table 22). At Day 85, the proportion of patients who achieved an EASI score percent decrease of 50% ("EASI-50") was 85.5% for the 300 mg group, whereas the EASI-50 for placebo-treated patients at Day 85 was 35.2% (Table 23). The percent change in EASI score from baseline to week 12 of mAb1 was statistically significant from placebo group (−74.0% vs. −23.0%, p-value<0.0001). Treatment with mAb1 significantly reduced all four disease components of EASI compared with placebo: erythema, infiltration/population/edema, excoriation and lichenification (p<0.0001 for all 4 components; FIG. 15). The treatment group was statistically significantly different from placebo group in all of the secondary efficacy endpoints. The following were the p-values for: IGA responder (0 or 1) (<0.0001), EASI responder (<0.0001), EASI absolute change from baseline (<0.0001), absolute change of IGA from baseline (<0.0001), percent change of IGA from baseline (<0.0001), absolute change in BSA (<0.0001), absolute change in SCORAD (<0.0001), absolute change in Pruritus NRS (<0.0001), and absolute change in 5-D pruritus scale from baseline to week 12 (<0.0001) respectively. Treatment with mAb1 significantly reduced all five components of 5-D Pruritus score: duration, degree, direction, disability and distribution (p<0.0001 for duration, degree, disability and distribution, p<0.001 for direction; FIG. 24). Administration of 300 mg mAb1 significantly improved QoL relative to placebo over the 12-week treatment (FIG. 27). Improvement from baseline in QoLIAD was significantly greater with mAb1 relative to placebo at 4 weeks (LS mean difference −5.1; 95% CI −7.7, −2.4; P=0.0003), 12 weeks (LS mean difference −6.4; 95% CI −9.0, −3.8; P<0.0001), and end of study (LS mean difference −6.3; 95% CI −9.0, −3.7; P<0.0001). At 12 weeks, changes in QoLIAD with mAb1 moderately correlated with changes in disease activity and pruritus, with Pearson correlation coefficients of 0.435 for the EASI score, 0.406 for the pruritus numerical rating score, and 0.494 for the 5D Pruritus Scale score (all P<0.05). Further, treatment with 300 mg mAb1 also resulted in fewer skin infections in patients with AD (5.5%) compared with placebo (24.5%), including bacterial, viral and fungal infections. Patients treated with mAb1 showed a reduced susceptibility to microbial infections than those on placebo.

Example 3: Skin Barrier Function Analysis

Skin barrier function analysis was conducted on samples taken from subjects who participated in clinical trials of mAb1.

Study A

In 'Study A', AD subjects were administered either mAb1 (75, 150 or 300 mg) or placebo, on days 1, 8, 15 and 22 of the study (i.e., four weekly doses). Stratum corneum hydration (SCH; corneometry) and transepidermal water loss (TEWL; evaporimetry) (Vergananini et al 2010, J. Dermatol. Treatment 21: 126-129) were measured at baseline, day 29 (end of treatment) and day 85 (end of study) for a subset of patients in the study.

The median baseline measurements for SCH and TEWL are summarized in Table 25.

TABLE 25

Median baseline SCH and TEWL

| Skin type | | Placebo | 75 mg | 150 mg | 300 mg | All doses |
|---|---|---|---|---|---|---|
| SCH (a.u.) | Lesional | 15 | 10 | 22 | 13 | 11 |
| SCH (a.u.) | Non-lesional | 31 | 21 | 31 | 25 | 28 |
| TEWL (g/m²/hr) | Lesional | 15 | 59 | 22 | 32 | 38 |
| TEWL (g/m²/hr) | Non-lesional | 6 | 19 | 7 | 12 | 12 |

For SCH, the higher the capacitance (a.u.), the more hydrated the skin. The median SCH results for both lesional and non-lesional skin were below those reported for "normal" skin (i.e., skin of a person without AD). As expected, the lesional SCH measures were lower than for non-lesional areas (Table 25).

For TEWL, the higher the measurement, the greater the loss of water from the skin.

Median baseline TEWL measures were high (thus, too much water evaporation from the skin) in the lesional areas tested compared to those reported for normal skin. Median lesional measures were higher than those for non-lesional areas. Median non-lesional results for the placebo and 150 mg groups were close to reported normal values.

Figure 29:
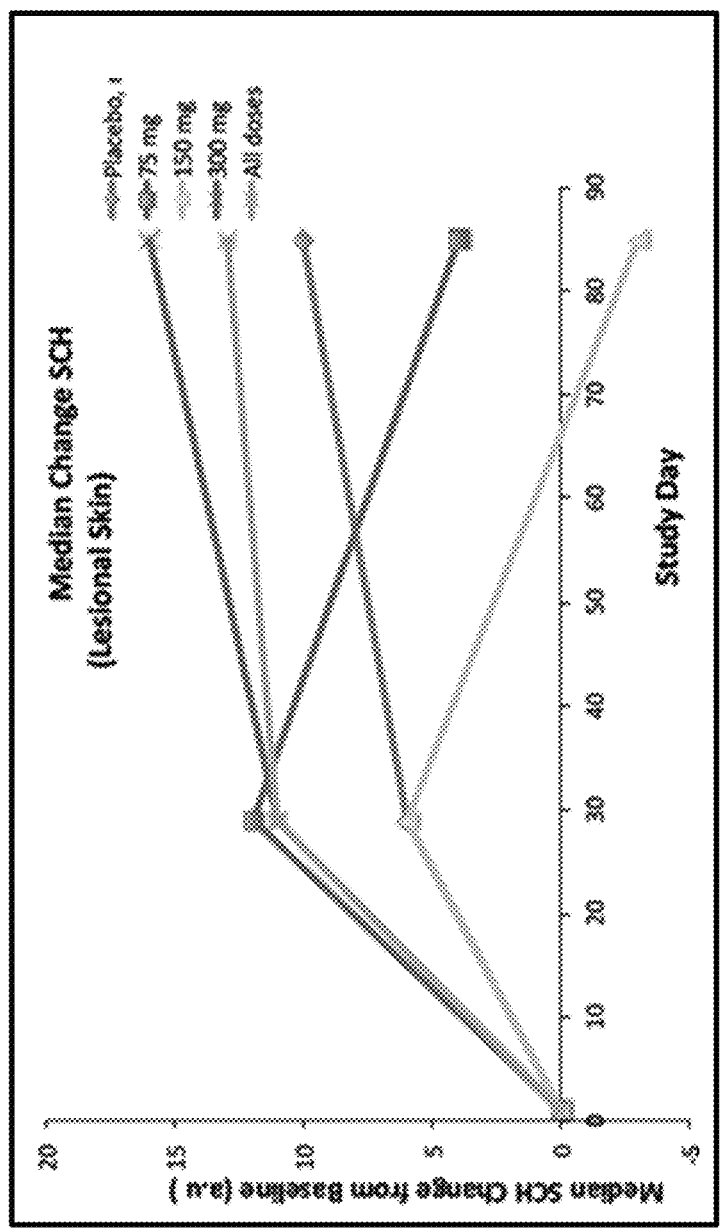
FIG. 29 shows the median change from baseline in SCH in lesional skin for the study in Example 3.
Figure 30:
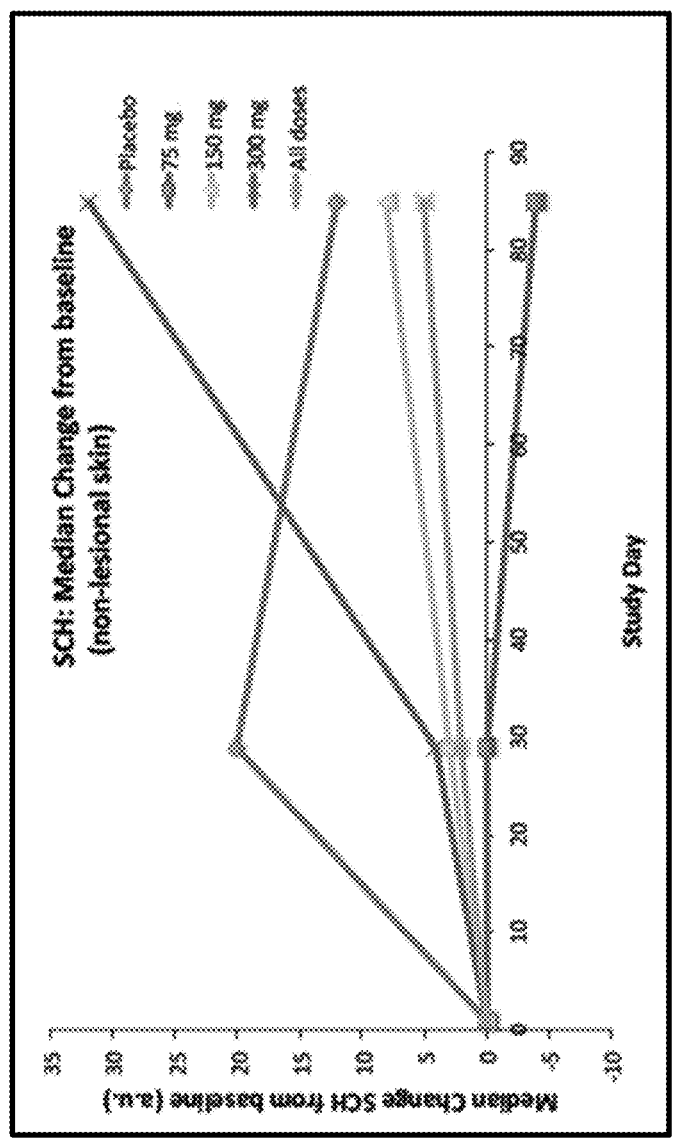
FIG. 30 shows the median change from baseline in SCH in non-lesional skin for the study in Example 3.

Treatment with mAb1 showed increases in SCH of lesional and non-lesional areas in all dose groups. The results show that there is a trend for SCH improvement of lesional areas with mAb1 treatment compared to placebo at day 29 (FIG. 29). Non-lesional areas had better SCH at baseline and the magnitudes of post-treatment changes observed were not as large, in general (FIG. 30).

Figure 31:
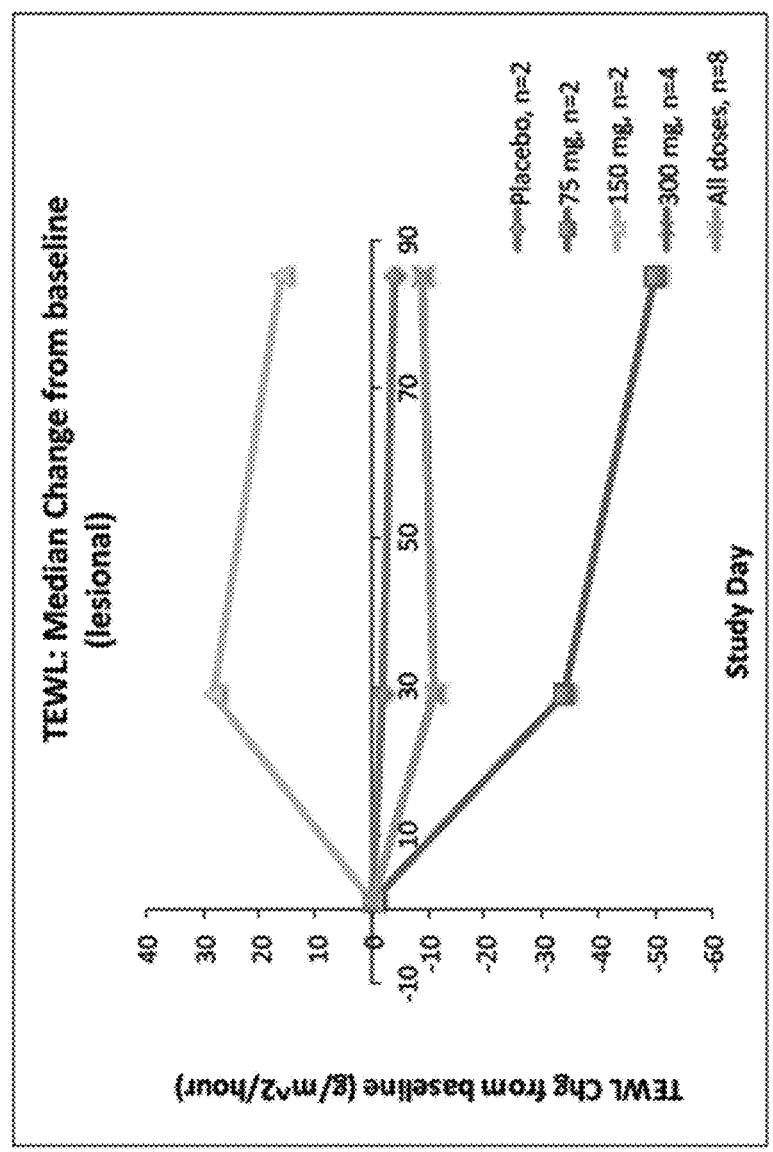
FIG. 31 shows median change from baseline in TEWL in lesional skin for the study in Example 3.
Figure 32:
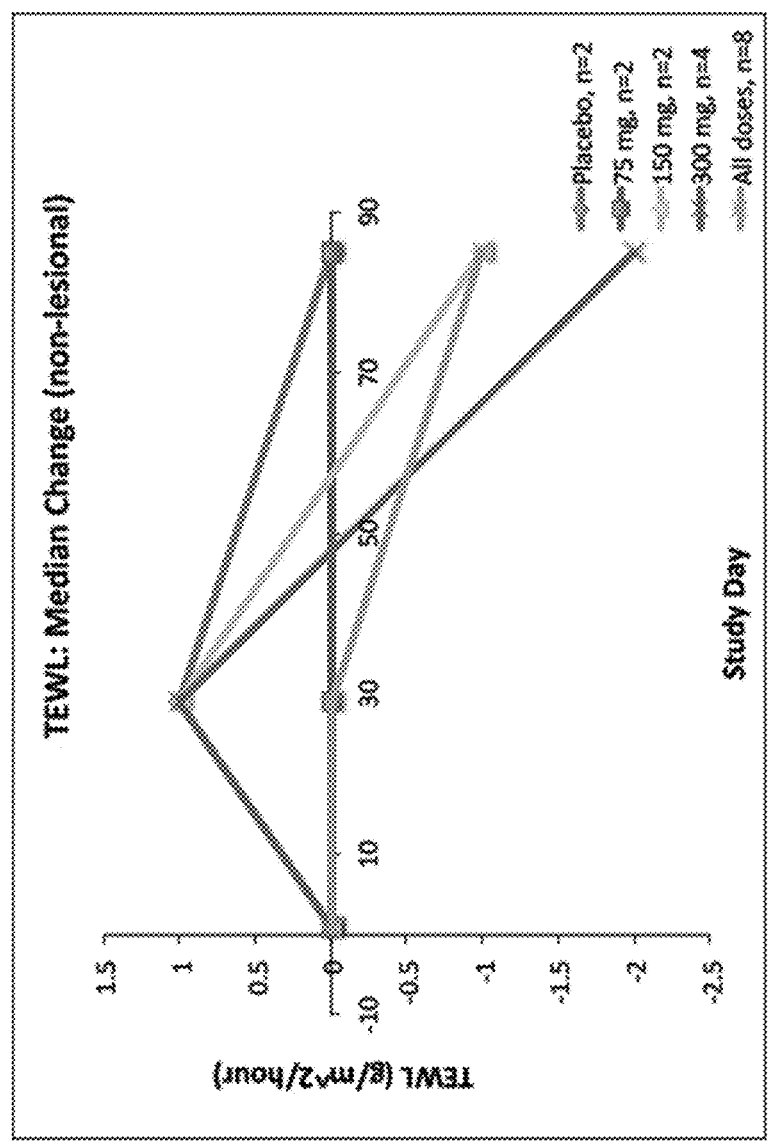
FIG. 32 shows the median change from baseline in TEWL in non-lesional skin for the study in Example 3.

For TEWL, there may be a trend for improvement in the lesional areas, with the exception of the 150 mg group (FIG. 31). A trend for a TEWL improvement was observed with measurements taken from non-lesional skin, however this was mostly observed after day 29, when topical treatments were allowed (FIG. 32).

Study B

Study B was a phase 2b study to assess safety and efficacy of mAb1 in adults with moderate-to-severe AD. The protocol details are disclosed in Example 9 of US Patent Application Publication No. US20140072583, which is incorporated herein in its entirety.

After a loading dose, patients received placebo (PBO) or mAb1 (100 mg q4w, 300 mg q4w, 200 mg q2w, 300 mg q2w or 300 mg qw) for 16 weeks (wks), with an additional 16-wk safety follow-up. The most common TEAEs (PBO vs mAb1) were nasopharyngitis (26.2% vs 28%), headache (3.3% vs 10.7%), and injection site reaction (3.3% vs 6.9%).

A TEWL and stratum corneum hydration (SCH) sub-study was conducted. At baseline lesional areas, mAb1 significantly reduced TEWL at Wk 4 (−27%±4 all mAb1 [n=44] vs+696%±645 PBO [n=7], p<0.0001, mean change±SE) and improved or maintained TEWL through Wk 16 (−42%±5 all mAb1 [n=31] vs+62.3%±33 PBO [n=3], p<0.001). There was no consistent difference in SCH between mAb1- and PBO-treated patients. Improvement in TEWL correlated with thymus and activation-regulated chemokine (TARC) suppression (mean % change, Wk 16, Spearman r=0.32, p<0.01). Mean % changes in the Th2 biomarkers TARC, periostin, or eosinophils were assessed for correlation with mean % changes in other clinical measures. At Wk 16, the strongest correlations were mean % changes in TARC with clinical outcomes (Pruritus 5D, r=0.45; Patient Oriented Eczema Measure (POEM), r=0.40; body surface area, r=0.39; SCORing Atopic Dermatitis (SCORAD), r=0.36; Investigator's Global Assessment (IGA), r=0.35; Eczema Area and Severity Index (EASI), r=0.33; all p<0.0001). These correlations were independent of treatment. IL-4Rα blockade with mAb1 may improve both inflammatory and barrier impairments driving AD pathogenesis.

Example 4: *Staphylococcus aureus* Skin Colonization

Figure 33:
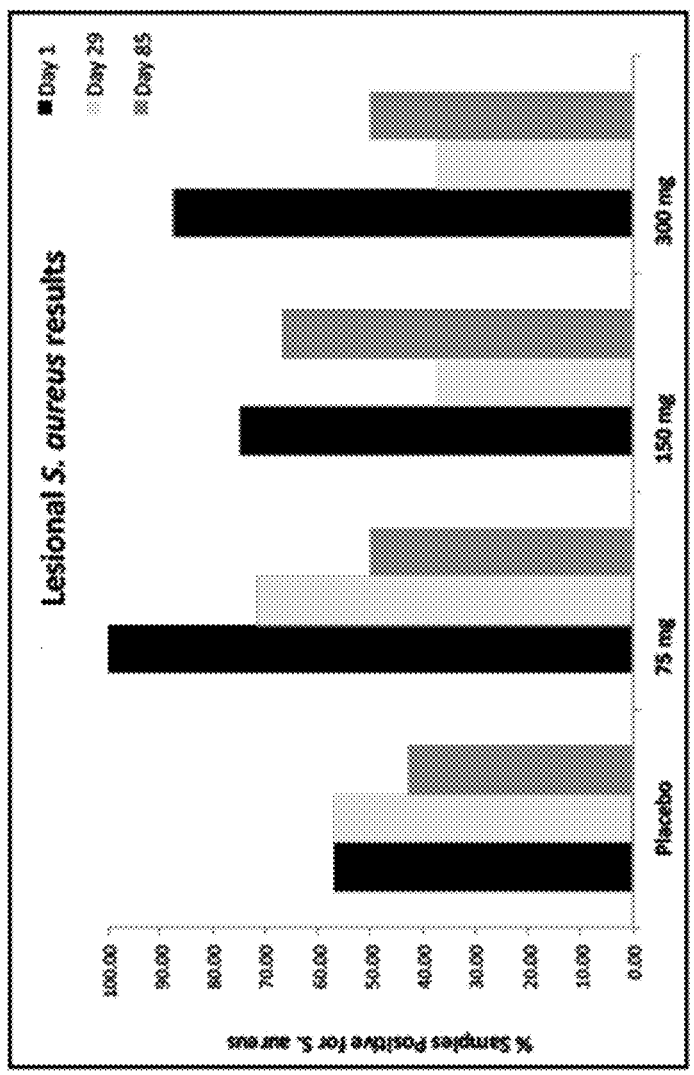
FIG. 33 shows percent samples positive for *S. aureus* in lesional skin for the study in Example 4.
Figure 34:
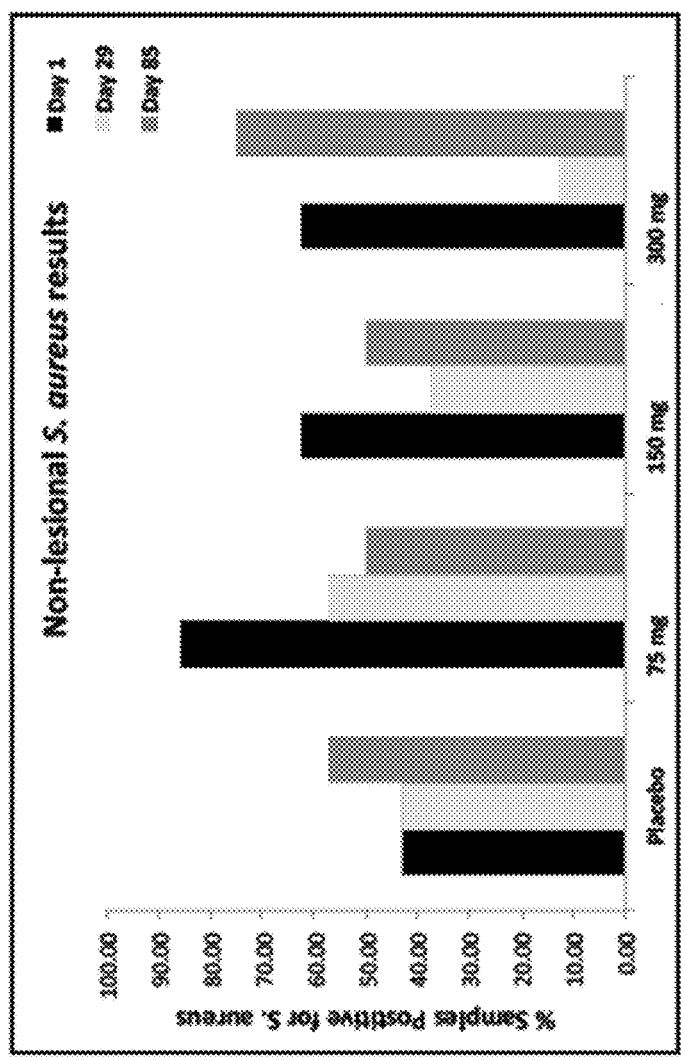
FIG. 34 shows percent sample positive for *S. aureus* in non-lesional skin for the study in Example 4.
Figure 35:
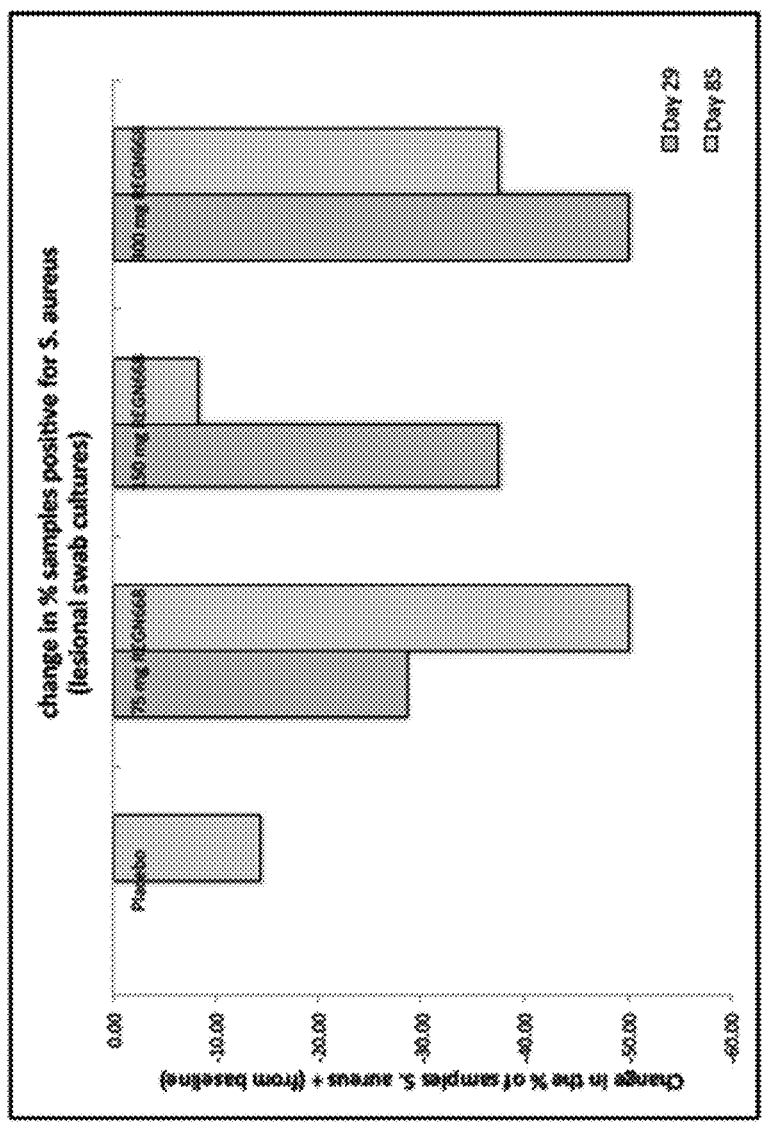
FIG. 35 shows change in percent positive *S. aureus* samples from baseline in lesional skin for the study in Example 4.
Figure 36:
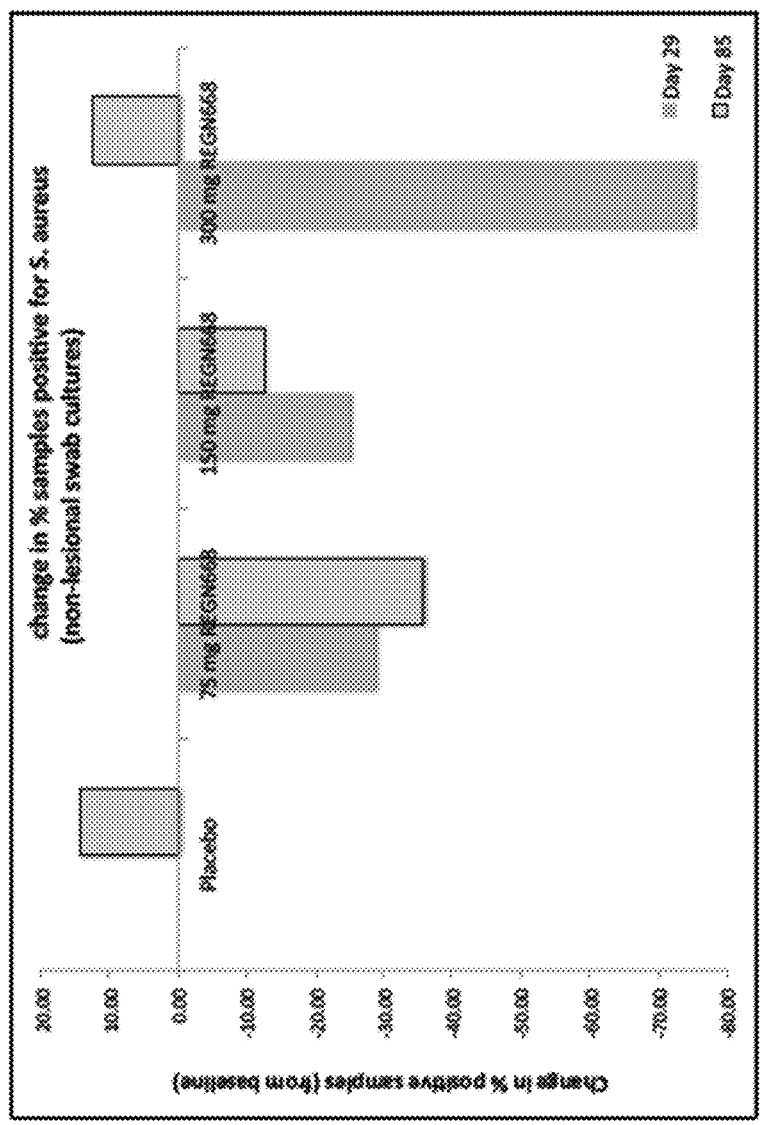
FIG. 36 shows change in percent positive *S. aureus* samples from baseline in non-lesional skin for the study in Example 4.

Skin microbial colonization analysis was conducted on samples taken from subjects who participated in clinical trials of mAb1. In 'Study A', AD subjects were administered either mAb1 (75, 150 or 300 mg) or placebo, on days 1, 8, 15 and 22 of the study (i.e., four weekly doses). Skin swabs were collected and cultured for the presence of *S. aureus*. The percentage of positive samples collected pre- and post-treatment were evaluated. More than 50% of all baseline samples from lesional skin tested positive for *S. aureus* colonization (FIG. 33). In all treatment groups, the percentage of positive samples decreased after treatment at day 29 (end of treatment; FIG. 34). A dose response trend for lower colonization with treatment was observed. Day 85 results were mixed, with continued decrease in the 75 mg and placebo groups, and the other two mAb1 dose groups increasing (but still below baseline). A similar observation was made for the percentage of positive samples from non-lesional skin, however dose dependency was not observed for the percentage decrease (FIGS. 35-36). The *S. aureus* culture results from skin swab samples collected in this study suggest that mAb1 treatment may improve *S. aureus* skin colonization in AD patients.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of reducing susceptibility to a skin infection in a subject with atopic dermatitis, the method comprising:
administering a pharmaceutical composition comprising a therapeutically effective amount of an Interleukin-4 Receptor (IL-4R) antagonist to the subject in need thereof for a period of at least 12 weeks, wherein at the start of treatment a sample of skin from the subject is positive for microbial colonization by a microbe selected from the group consisting of *Staphylococcus aureus, Streptococcus* spp., *Pseudomonas aeruginosa, Bacteroides* spp., Herpes simplex virus, molluscum contagiosum virus, coxsackievirus, vaccinia virus, *Candida albicans, Microsporum* spp., *Trichophyton* spp., *Penicillium* spp., *Cladosporium* spp., *Alternaria* spp., and *Aspergillus* spp.;
wherein the IL-4R antagonist is an antibody or antigen-binding fragment thereof that specifically binds IL-4Rα, wherein the antibody or antigen binding fragment thereof comprises three heavy chain complementarity determining regions (HCDR1, HCDR2 and HCDR3) of a heavy chain variable region (HCVR) comprising SEQ ID NO: 1, and three light chain complementarity determining regions (LCDR1, LCDR2 and LCDR3) of a light chain, variable region (LCVR) comprising SEQ ID NO: 2;
wherein the IL-4R antagonist is administered at an initial dose followed by one or more secondary doses, wherein the initial dose comprises about 50 mg to about 600 mg of the IL-4R antagonist and each secondary dose comprises about 25 mg to about 400 mg of the IL-4R antagonist, and wherein each secondary dose is administered 1 to 4 weeks after the immediately preceding dose.

2. The method of claim 1, wherein at the start of treatment a sample of skin from the subject is positive for microbial colonization by *Staphylococcus aureus*.

3. The method of claim 1, wherein the subject has moderate-to-severe atopic dermatitis.

4. The method of claim 1, wherein HCDR1 comprises SEQ ID NO: 3, HCDR2 comprises SEQ ID NO: 4, HCDR3 comprises SEQ ID NO: 5, LCDR1 comprises SEQ ID NO: 6, LCDR2 comprises SEQ ID NO: 7, and LCDR3 comprises SEQ ID NO: 8.

5. The method of claim 1, wherein the antibody or antigen-binding fragment thereof comprises an HCVR that comprises SEQ ID NO: 1 and an LCVR that comprises SEQ ID NO: 2.

6. The method of claim 1, wherein the anti-IL-4R antibody is dupilumab or a bioequivalent thereof.

7. The method of claim 1, wherein the initial dose comprises about 600 mg of the IL-4R antagonist, and each secondary dose comprises about 300 mg of the IL-4R antagonist.

8. The method of claim 7, wherein each secondary dose is administered one week after the immediately preceding dose.

9. The method of claim 7, wherein each secondary dose is administered 2 weeks after the immediately preceding dose.

10. The method of claim 1, wherein the IL-4R antagonist is administered subcutaneously.

11. The method of claim 1, wherein the IL-4R antagonist is contained in a container selected from the group consisting of a syringe, a glass vial, a pre-filled pen delivery device, and an autoinjector.

12. The method of claim 11, wherein the IL-4R antagonist is contained in a syringe.

13. The method of claim 11, wherein the IL-4R antagonist is contained in a glass vial.

14. The method of claim 11, wherein the IL-4R antagonist is contained in a pre-filled pen delivery device.

15. The method of claim 11, wherein the IL-4R antagonist is contained in an autoinjector.

16. The method of claim 1, wherein a second therapeutic agent is administered to the subject before, after, or concurrent with the pharmaceutical composition.

17. The method of claim 16, wherein the second therapeutic agent is selected from the group consisting of an anti-bacterial agent, an anti-viral agent, an anti-fungal agent, another IL-4R antagonist, an IgE inhibitor, a corticosteroid, a non-steroid anti-inflammatory drug (NSAID), and IFNγ.

* * * * *

SEQUENCE LISTING

<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: synthetic

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: synthetic

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic -continued

```
<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: synthetic

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: synthetic

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: synthetic

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: synthetic

<400> SEQUENCE: 8

Met Gln Ala Leu Gln Thr Pro Tyr Thr
1               5

<210> SEQ ID NO 9
<211> LENGTH: 207
<212> TYPE: PRT
<213> ORGANISM: Human
<220> FEATURE:
<223> OTHER INFORMATION: IL-4Ralpha

<400> SEQUENCE: 9

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
                20                  25                  30

Leu Arg Leu Leu Tyr Gln Leu Val Phe Leu Leu Ser Glu Ala His Thr
            35                  40                  45
```

```
Cys Ile Pro Glu Asn Asn Gly Gly Ala Gly Cys Val Cys His Leu Leu
     50                  55                  60

Met Asp Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
                 85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
        130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
            195                 200                 205

<210> SEQ ID NO 10
<211> LENGTH: 451
<212> TYPE: PRT
<213> ORGANISM: Artificial Sequence
<220> FEATURE:
<223> OTHER INFORMATION: HC
      aa 1-124: HCVR
      aa 125-451: HC constant region

<400> SEQUENCE: 10

Glu Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ser Ser Ile Ser Gly Ser Gly Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly
    450

<210> SEQ ID NO 11
<211> LENGTH: 219
<212> TYPE: PRT
<213> ORGANISM: Artificial Sequence
<220> FEATURE:
<223> OTHER INFORMATION: LC
    aa 1-112: LCVR
    aa 113-219: LC constant region

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Phe Tyr Tyr Cys Met Gln Ala
                85              90                  95

Leu Gln Thr Pro Tyr Thr Phe Gly Gln Gly Thr Lys Leu Glu Ile Lys
            100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```